(12) United States Patent
Rafii et al.

(10) Patent No.: US 11,932,876 B2
(45) Date of Patent: Mar. 19, 2024

(54) STABLE THREE-DIMENSIONAL BLOOD VESSELS AND METHODS FOR FORMING THE SAME

(71) Applicant: CORNELL UNIVERSITY, Ithaca, NY (US)

(72) Inventors: Shahin Rafii, Ithaca, NY (US); Brisa Palikuqi, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 1111 days.

(21) Appl. No.: 16/483,095

(22) PCT Filed: Feb. 2, 2018

(86) PCT No.: PCT/US2018/016640
§ 371 (c)(1),
(2) Date: Aug. 2, 2019

(87) PCT Pub. No.: WO2018/144860
PCT Pub. Date: Aug. 9, 2018

(65) Prior Publication Data
US 2019/0376044 A1 Dec. 12, 2019

Related U.S. Application Data

(60) Provisional application No. 62/454,161, filed on Feb. 3, 2017.

(51) Int. Cl.
*C12N 5/071* (2010.01)
*A61K 35/44* (2015.01)
*A61L 27/38* (2006.01)
*A61L 27/50* (2006.01)

(52) U.S. Cl.
CPC ............ *C12N 5/0691* (2013.01); *A61K 35/44* (2013.01); *A61L 27/3808* (2013.01); *A61L 27/507* (2013.01); *A61L 2430/22* (2013.01); *A61L 2430/40* (2013.01); *C12N 2500/02* (2013.01); *C12N 2510/00* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 8,372,642 B2 | 2/2013 | Rajesh et al. | |
| 8,785,192 B2 | 7/2014 | Yu et al. | |
| 9,242,027 B2 | 1/2016 | Bellan et al. | |
| 9,637,723 B2 | 5/2017 | Rafii et al. | |
| 10,113,149 B2 | 10/2018 | Sandler et al. | |
| 2012/0301443 A1 | 11/2012 | Raffi et al. | |
| 2013/0224161 A1 | 8/2013 | Rafii et al. | |
| 2014/0315753 A1 | 10/2014 | Guye et al. | |
| 2014/0349398 A1 | 11/2014 | Yu et al. | |
| 2015/0253309 A1* | 9/2015 | Marx | C12M 23/16 435/284.1 |
| 2016/0168538 A1 | 6/2016 | Wary et al. | |

FOREIGN PATENT DOCUMENTS

| | | |
|---|---|---|
| CN | 102388130 A | 3/2012 |
| CN | 104520422 A | 4/2015 |
| CN | 106163572 A | 11/2016 |
| JP | 2015109833 A | 6/2015 |
| JP | 2015192681 A | 11/2015 |
| JP | 2016513465 A | 5/2016 |
| WO | 2010/099539 A1 | 9/2010 |
| WO | 2014/113415 A1 | 7/2014 |
| WO | 2016/100869 A1 | 6/2016 |
| WO | 2016/141137 A1 | 9/2016 |
| WO | 2016/141234 A1 | 9/2016 |

OTHER PUBLICATIONS

Baptista et al, Hepatology, 2011, 53(2):604-617. (Year: 2011).*

(Continued)

*Primary Examiner* — Allison M Fox
(74) *Attorney, Agent, or Firm* — Scully, Scott, Murphy & Presser, P.C.

(57) ABSTRACT

The present disclosure provides methods for forming stable three-dimensional vascular structures, such as blood vessels and uses thereof. More specifically, the present disclosure provides methods for culturing differentiated endothelial cells that include an exogenous nucleic acid encoding ETV2 transcription factor on a matrix under conditions that express exogenous ETV2 protein in the endothelial cell to form stable three-dimensional artificial blood vessels without the use of a scaffold, pericytes or perfusion. The present disclosure also provides stable three-dimensional blood vessels that are capable of autonomously forming a functional three-dimensional vascular network, and uses thereof. In addition, the present disclosure includes methods for vascularizing an organoid and a decellularized organ by culturing the organoid or decellularized organ with endothelial cells that include an exogenous nucleic acid encoding ETV2 transcription factor under conditions that express exogenous ETV2 protein in the endothelial cell to vascularize the organoid or decellularized organ.

22 Claims, 22 Drawing Sheets
(22 of 22 Drawing Sheet(s) Filed in Color)
Specification includes a Sequence Listing.

(56) References Cited

OTHER PUBLICATIONS

"Efficacy." Merriam-Webster.com Dictionary, Merriam-Webster, https://www.merriam-webster.com/dictionary/efficacy. Accessed May 17, 2023. (Year: 2023).*
Badylak et al, Acta Biomaterialia, 2015, 23:S17-S26. (Year: 2015).*
Chan et al, Eur Spine J, 2008, 17 (Suppl 4): S467-S479. (Year: 2008).*
Yi et al, Current Stem Cell Research and Therapy, 2017, 12:233-246. (Year: 2017).*
English-language abstract of Japanese Office Action dated Nov. 16, 2021 received in Japanese Application No. 2019-542146, 18 pages.
Palikuqi B. et al., "Adaptable Haemodynamic Endothelial Cells for Organogenesis and Tumorigenesis", Nature 585:426-432 (Sep. 17, 2020).
Chinese Office Action dated Dec. 22, 2021 received in Chinese Application No. 201880022477.6, together with an English-language translation.
Chinese Office Action dated Jun. 2, 2021 received in Chinese Application No. 201880022477.6, together with an English-language translation.
Caralt, M. et al., "Optimization and Critical Evaluation of Decellularization Strategies to Develop Renal Extracellular Matrix Scaffolds as Biological Templates for Organ Engineering and Transplantation", American Journal of Transplantation (Nov. 17, 2014), vol. 15, No. 1, pp. 64-75.
Ginsberg M. et al., "Efficient Direct Reprogramming of Mature Amniotic Cells into Endothelial Cells by ETS Factors and TGFβ Suppression", Cell (Oct. 26, 2012), vol. 151, pp. 559-575.
Hebrok, M., "Generating β Cells from Stem Cells—The Story So Far", Cold Spring Harbor Perspectives in Medicine, 2012, 2(6):a007674, pp. 1-13. Downloaded from http://perspectivesinmedicine.cshlp.org/ on Sep. 10, 2019—Published by Cold Spring Harbor Laboratory Press.
Huh, D. et al., "From Three-Dimensional Cell Culture to Organs-on-Chips", Trends Cell Biol (Dec. 2011), vol. 21, No. 12, pp. 745-754.
James, D. et al., "Expansion and Maintenance of Human Embryonic Stem Cell-Derived Endothelial Cells by TGFβ Inhibition is Id1 Dependent", Nat Biotechnol (Feb. 2010), vol. 28, No. 2, pp. 161-166.
Levenberg, S. et al., "Isolation, Differentiation and Characterization of Vascular Cells Derived from Human Embryonic Stem Cells", Nat Protoc. (Jun. 2010), vol. 5, No. 6, pp. 1115-1126.
Li, Z. et al., "Functional and Transcriptional Characterization of Human Embryonic Stem Cell-Derived Endothelial Cells for Treatment of Myocardial Infarction", PLoS One, (Dec. 2009), vol. 4, No. 12, e8443, 28 pages.
Pashneh-Tala, S. et al., "The Tissue-Engineered Vascular Graft-Past, Present, and Future", Tissue Engineering: Part B (Nov. 1, 2016), vol. 22, No. 1, pp. 68-100.
Prasain, N. et al., "Differentiation of Human Pluripotent Stem Cells to Cells Similar to Cord-Blood Endothelial Colony-Forming Cells", Nat Biotechnol. (Nov. 2014) vol. 32, No. 11, pp. 1151-1157.
Rafii, S. et al., "Angiocrine Functions of Organ-Specific Endothelial Cells", Nature (Jan. 21, 2016), vol. 529, No. 7586, pp. 316-325.
Ramasamy, S.K., "Regulation of Tissue Morphogenesis by Endothelial Cell-Derived Signals", Trends Cell Biol (Mar. 2015), vol. 25, No. 3, pp. 148-157.
Rufaihah A.J. et al., "Endothelial Cells Derived From Human iPSCS Increase Capillary Density and Improve Perfusion in a Mouse Model of Peripheral Arterial Disease", Arterioscler Thromb Vasc Biol. (Nov. 2011), vol. 31, No. 11, pp. e72-e79.
Schachterle, W. et al., "Sox17 Drives Functional Engraftment of Endothelium Converted From Non-Vascular Cells", Nature Communications (Jan. 16, 2017), vol. 8:13963.
Schultheiss, D. et al. "Biological Vascularized Matrix for Bladder Tissue Engineering: Matrix Preparation, Reseeding Technique and Short-Term Implantation in a Porcine Model," The Journal of Urology, (Jan. 31, 2005), vol. 173, No. 1, pp. 276-280.
Wang, Z.Z. et al., "Endothelial Cells Derived from Human Embryonic Stem Cells Form Durable Blood Vessels In Vivo", Nat Biotechnol. (Mar. 2007), vol. 25, No. 3, pp. 317-318.
Zhang, Y. S. et al., "Bioprinting the Cancer Microenvironment", ACS Biomater Sci Eng (Oct. 10, 2016), vol. 2, No. 10, pp. 1710-1721.
International Search Report and the Written Opinion of the International Searching Authority from International Application No. PCT/US2018/016640 dated Jul. 11, 2018.

* cited by examiner

A

B

D

E

F

G

H

I

H

R-VEC 1 WEEK

I

R-VEC 4 WEEKS

J

SEQUENCE LISTING

```
<160> NUMBER OF SEQ ID NOS: 2

<210> SEQ ID NO 1
<211> LENGTH: 3697
<212> TYPE: DNA
<213> ORGANISM: Homo sapiens

<400> SEQUENCE: 1
attacaggcg tgaatcaccg cgcccaacca caagttacag acattataac atttcatctc      60
tgagttcatt ttctaaatga tatctttcct cctgaatacc attatcaaat ctaagaaaag     120
aattctatga tatttcatat tcagttcata ctccagtttc cccaattgtc ctaaactatt     180
acagcgcgga agggcatggg gtctggagaa ggagagcagt gggaggatgc ctgccttacc     240
ttcccccttc atcaaatgag agtatgtatt gtacttgcct catagaagga ttcaatgaag     300
gggtatggca cagttggttt cacacaatga gccctcattt aatgttggcc gttattgcta     360
ctattgttat tgttgaaatt gttgatgtca atattgctat gattggcact cctgggaagc     420
```

-continued

| | |
|---|---|
| agccccagga cgccctccct actgggcctg gtggaggatt gggtgggcct tcactcctgc | 480 |
| tccacgcccc cgcagttact ctgccgattg tgacgtcagc tgacgctggg ggcgggtggg | 540 |
| ggaatctggc cggaaatccc tcttcctgtt gcagataagc ccagcttagc ccagctgacc | 600 |
| ccagaccctc tccctcact cccccatgt cgcaggatcg agaccctgag gcagacagcc | 660 |
| cgttcaccaa gccccccgcc ccgccccat caccccgtaa acttctccca gcctccgccc | 720 |
| tgccctcacc cagcccgctg ttccccaagc ctcgctccaa gcccacgcca ccctgcagc | 780 |
| agggcagccc cagaggccag cacctatccc cgaggctggg gtcgaggctc ggccccgccc | 840 |
| ctgcctctgc aacttgagcc tggctgcgac ccctgctctg acgtctcgga aaattccccc | 900 |
| ttgcccaggc ccttggggga gggggtgcat ggtatgaaat ggggctgaga ccccggctg | 960 |
| ggggcagagg aacccgccag aggtgagcga tgaactgagg actagatgcc tgggtgtctg | 1020 |
| ggttaggaag gacctggggg actagactcc caagaagccg ggggcctgga ctcctgggtc | 1080 |
| taacagagga agagagctgg ggtccctcac tcccaggacc aagatttag gctcctgggg | 1140 |
| aaggagggag cggaggcctg gactcctggc tctgagggaa gctagggctg ggcccagac | 1200 |
| tccagggcct ccaagtgtca ccagctcacc cattgccatc tggacttttc ccgacccaga | 1260 |
| acattcagaa ggccttcatc gcatccatgg acctgtggaa ctgggatgag gcatccccac | 1320 |
| aggaagtgcc tccagggaac aagctggcag ggcttggtag gctgccgagg ctgccacaac | 1380 |
| gtgtgtgggg agggtgtcca ggtggggcct ctgctgaccc taacccctta tcgcctgcag | 1440 |
| aaggagccaa attaggcttc tgtttccctg atctggcact ccaaggggac acgccgacag | 1500 |
| cgacagcaga gacatgctgg aaaggtggct gcgggctggg acccctaagt gctggagaag | 1560 |
| aagcggggag gctgggatcc tagggcaaag ggaggagggg ggcgtgccta ggttcctggg | 1620 |
| actgggtggg gaggggccgc gtgcttgacc cctgagggtg aaggaaaagg gggcgcgggg | 1680 |
| tgctgaaata cgggctgggg ggccataact cccagtccct gacaagtaga gactagagag | 1740 |
| tgggtagttg aggggtctct ttcattgctc acagtcctcc ctaaactcag gtacaagctc | 1800 |
| atccctggca agcttcccac agctggactg gggctccgcg ttactgcacc cagaagttcc | 1860 |
| atggggggcg ggtgagtgtg gggagaggcg gtgggaggtg gggactgggg tcccgaggca | 1920 |
| ccggggctag aggtgtagac tccctgatct ttgaggactg agaacacctg cgccctcaag | 1980 |
| gtggcatgac ctggatccgg gtcagccggg ccccaagtgc cagggttgag agcttagacc | 2040 |
| ctagagtttt tgagggggca cctgggctcc cctcactcgg gatccgttac tcctcacaga | 2100 |
| gcccgactct caggctcttc cgtggtccgg ggactggaca gacatggcgt gcacagcctg | 2160 |
| ggactcttgg agcggcgcct cgcagaccct gggccccgcc cctctcggcc cgggccccat | 2220 |
| ccccgccgcc ggctccgaag gcgccgcggg ccagaactgc gtccccgtgg cgggagaggc | 2280 |
| cacctcgtgg tcgcgcgccc aggccgccgg gagcaacacc agctgggact gttctgtggg | 2340 |
| gcccgacggg gatacctact ggggcagtgg cctgggcggg gagccgcgca cggactgtac | 2400 |
| catttcgtgg ggcgggcccg cgggcccgga ctgtaccacc tcctggaacc cggggctgca | 2460 |
| tgcgggtggc accacctctt tgaagcggta ccagagctca gctctcaccg tttgctccga | 2520 |
| accgagcccg cagtcggacc gtgccagttt ggctcgatgc cccaaaacta accaccgagg | 2580 |
| tgagagggcc gcaaagactg cggggagggc gaagctggag tcctgagccg ggacccaggc | 2640 |
| acctaagggg gcggggcccg ggagactgac agtgaggggg cggggcctta gggaccaggg | 2700 |
| gctcgaagga ggggccggtg gcccgcactc caggtccttg gggaggagag ggctaagaaa | 2760 |

-continued

```
ctggtagtct tatagggacc aaggggatga ggacccaggc tcctggatta tataaaacga    2820
aagcgataaa ggcccagatt cctgggtctc cgagatgggg aggccaaact cctaaatctc    2880
tgagactggg gccctggacg cttgagtctc caaggctgac tgttggatct cagagaaggg    2940
ggggcggatc cccttctcgg gtcctgggtc ccgagttggg aggacccgga cctctagatc    3000
attgaagtgg tgtgatctag ggccgggaag actgagtgtg cccctccctt catcccgcag    3060
gtcccattca gctgtggcag ttcctcctgg agctgctcca cgacgggggcg cgtagcagct    3120 gcatccgttg gactggcaac agccgcgagt tccagctgtg cgaccccaaa gaggtggggc    3180
agctcccctg cccagccaaa tccgcccgt ctcttctagt tcaatttagc tccgcccaag    3240
ggctaggttc aaccgcgtag ccctcggccc cgccgctccc cggcccactc gaggccccgc    3300
ccaacccttc tcaaacccaa tctcccgcct gtactcctgc tcaaccaac ccagtctcca    3360 ccgggctctg cgaggcctcg cccaggtctg cactgcacac cgcccccagg cccggccctc    3420
cccactatcg ccaagccccg cccttccca ctccgaccga gcgggcctct gtcctaggtg    3480
gctcggctgt ggggcgagcg caagagaaag ccgggcatga attacgagaa gctgagccgg    3540
ggccttcgct actactatcg ccgcgacatc gtgcgcaaga gcggggggcg aaagtacacg    3600
taccgcttcg ggggccgcgt gcccagccta gcctatccgg actgtgcggg aggcggacgg    3660
ggagcagaga cacaataaaa attcccggtc aaacctc                             3697
```

<210> SEQ ID NO 2
<211> LENGTH: 342
<212> TYPE: PRT
<213> ORGANISM: Homo sapiens

<400> SEQUENCE: 2

```
Met Asp Leu Trp Asn Trp Asp Glu Ala Ser Pro Gln Glu Val Pro Pro
1               5                  10                  15

Gly Asn Lys Leu Ala Gly Leu Glu Gly Ala Lys Leu Gly Phe Cys Phe
            20                  25                  30

Pro Asp Leu Ala Leu Gln Gly Asp Thr Pro Thr Ala Thr Ala Glu Thr
        35                  40                  45

Cys Trp Lys Gly Thr Ser Ser Leu Ala Ser Phe Pro Gln Leu Asp
    50                  55                  60

Trp Gly Ser Ala Leu Leu His Pro Glu Val Pro Trp Gly Ala Glu Pro
65                  70                  75                  80

Asp Ser Gln Ala Leu Pro Trp Ser Gly Asp Trp Thr Asp Met Ala Cys
                85                  90                  95

Thr Ala Trp Asp Ser Trp Ser Gly Ala Ser Gln Thr Leu Gly Pro Ala
            100                 105                 110

Pro Leu Gly Pro Gly Pro Ile Pro Ala Ala Gly Ser Glu Gly Ala Ala
        115                 120                 125

Gly Gln Asn Cys Val Pro Val Ala Gly Glu Ala Thr Ser Trp Ser Arg
    130                 135                 140

Ala Gln Ala Ala Gly Ser Asn Thr Ser Trp Asp Cys Ser Val Gly Pro
145                 150                 155                 160

Asp Gly Asp Thr Tyr Trp Gly Ser Gly Leu Gly Gly Glu Pro Arg Thr
                165                 170                 175

Asp Cys Thr Ile Ser Trp Gly Gly Pro Ala Gly Pro Asp Cys Thr Thr
            180                 185                 190

Ser Trp Asn Pro Gly Leu His Ala Gly Gly Thr Thr Ser Leu Lys Arg
        195                 200                 205
```

```
Tyr Gln Ser Ser Ala Leu Thr Val Cys Ser Glu Pro Ser Pro Gln Ser
    210                 215                 220

Asp Arg Ala Ser Leu Ala Arg Cys Pro Lys Thr Asn His Arg Gly Pro
225                 230                 235                 240

Ile Gln Leu Trp Gln Phe Leu Leu Glu Leu Leu His Asp Gly Ala Arg
                245                 250                 255

Ser Ser Cys Ile Arg Trp Thr Gly Asn Ser Arg Glu Phe Gln Leu Cys
                260                 265                 270

Asp Pro Lys Glu Val Ala Arg Leu Trp Gly Glu Arg Lys Arg Lys Pro
        275                 280                 285

Gly Met Asn Tyr Glu Lys Leu Ser Arg Gly Leu Arg Tyr Tyr Tyr Arg
        290                 295                 300

Arg Asp Ile Val Arg Lys Ser Gly Gly Arg Lys Tyr Thr Tyr Arg Phe
305                 310                 315                 320

Gly Gly Arg Val Pro Ser Leu Ala Tyr Pro Asp Cys Ala Gly Gly Gly
                325                 330                 335

Arg Gly Ala Glu Thr Gln
                340
```

STABLE THREE-DIMENSIONAL BLOOD VESSELS AND METHODS FOR FORMING THE SAME

CROSS REFERENCE TO RELATED APPLICATION

This application claims the benefit of priority from U.S. Provisional Application No. 62/454,161, filed on Feb. 3, 2017, the entire content of which is incorporated herein by reference.

INCORPORATION BY REFERENCE OF SEQUENCE LISTING

The Sequence Listing in the ASCII text file, named as 34633 7600 03 US Sequence Listing.txt of 9 KB, created on Aug. 1, 2019 and submitted to the United States Patent and Trademark Office via EFS-Web, is incorporated herein by reference.

FIELD OF THE DISCLOSURE

The present disclosure relates generally to methods for forming stable, three-dimensional vascular structures, such as blood vessels. More specifically, the present disclosure is directed to stable three-dimensional artificial blood vessels, scaffold-free methods for forming such vessels and uses thereof.

BACKGROUND OF THE DISCLOSURE

Embryonic organogenesis and tissue regeneration are dependent on vascularization with functional long-lasting blood vessels. Carmeliet, P. & Jain, R. K. *Nature* (2011) 473, 298-307. Blood vessels are critical for sustaining tissue-specific homeostasis, and for supplying paracrine angiocrine factors to guide proper patterning and morphogenesis of developing tissue. See, e.g., Ramasamy, S. K. et al. *Trends Cell Biol* (2015) 25, 148-157; and Rafii, S. et al. *Nature* (2016) 529, 316-325.

Attempts to induce the formation of new blood vessels to repair injured organs, a process known as angiogenesis, have confronted with hurdles. See, Samuel, R. et al. *Sci Transl Med* (2015) 7, 309. To date, injection of angiogenic factors into injured organs to induce vascularization has not been effective in establishing functional durable capillaries for long term use. Further, approaches to generate stable blood vessels in vitro for translation to the clinical setting have been cumbersome and time-consuming. For example, current approaches require the fabrication of scaffolds to form three-dimensional vessels, the use of perivascular pericytes, and enforced perfusion to recreate the hemodynamic microenvironment. See Huh, D. et al. *Trends Cell Biol* (2011) 21, 745-754.

In addition, existing models use clinically incompatible artificial extracellular matrixes, such as Matrigel™ (Corning), which limit the remodeling and patterning of putative capillary networks in culture. While mature adult human endothelial cells form vascular networks in Matrigel™ (Corning) matrices in vitro or in vivo, these vessels are not stable, have limited remodeling potential, and regress within few weeks.

Technologies to generate organ-on-chip models (See Huh, D. et al. *Trends Cell Biol* (2011) 21, 745-754) and three-dimensional bioprinting (See Zhang, Y. S. et al. *ACS Biomater Sci Eng* (2016) 2, 1710-1721) have vastly improved disease modeling and drug screening. However, the ability to incorporate physiologically relevant vascular cells into these approaches has lagged behind. Specifically, in the present approaches direct endothelial cell interaction with tissue-specific epithelial and tumor cells is restricted due to physical constraints introduced by artificial biomaterials. Further, present organ-on-chip or vascular scaffolding approaches require separation by layer(s) of semipermeable artificial biomaterials, which impair requisite physical cell-cell interaction between endothelial and non-vascular cells, thereby limiting adaptive or maladaptive endothelial cell remodeling. See Ginsberg, M. et al. *Cell* (2012) 151, 559-575; Schachterle, W. et al. *Nature communications* (2017) 8, 13963; Israely, E. et al. *Stem Cells* (2013) 1521; and James, D. et al. *Nat Biotechnol* (2010) 28, 161-166.

The need for the use of scaffolds, physical barriers and artificial matrices has limited the in vitro studies of endothelial cell cross-talk with organoid cultures and the translation of tissue-specific artificial vascular structures. Therefore, new approaches to vascularize tumor or tissue-specific organoids or decellularized organs with endothelial cells that can co-mingle and remodel with organotypic stem cells will improve translation to the clinical setting for regeneration, drug screening and tumor targeting.

The stable three-dimensional blood vessels and methods of the present disclosure utilize an unrecognized reprogramming element that dictates the formation of stable three-dimensional artificial blood vessels that are fully functional in vivo for a duration of time that is much longer than present artificial vessels. Further, the compositions and methods disclosed herein generate organ specific blood vessels capable of vascularizing injured tissue, organoids and decellularized organs.

SUMMARY OF THE DISCLOSURE

The present disclosure reveals that ETS-transcription factor variant 2, ETV2 (ER71, ETSRP71), directs endothelial cell development and that transient ETV2 expression plays an essential role in reprogramming differentiated endothelial cells to primitive-like endothelial cells that are more plastic, malleable, and responsive to environmental stimuli, as well as accommodating to other non-vascular cell types, including normal epithelial cells and tumor cells. More specifically, the methods and compositions of the present disclosure identify that exogenous expression of ETV2 transcription factor in endothelial cells cultured on matrices containing extracellular matrix components results in the formation of stable and functional three-dimensional artificial blood vessels in vitro and in vivo without the use of pericytes, perfusion and cumbersome scaffolds. As such the present disclosure is directed to the discovery that reprogrammed endothelial cells cultured on matrices, such as matrices, including laminin, entactin, and/or collagen IV form long-lasting, functional three-dimensional artificial blood vessels in vitro, as well as in vivo.

Therefore, a first aspect of the present disclosure is directed to methods for forming stable three-dimensional vascular structures, such as lumenized blood vessel tubules. A significant advantage of the methods described herein is that they do not utilize a three-dimensional scaffold, thereby advantageously eliminating costly and time-consuming elements presently required for forming artificial three-dimensional blood vessels. A further advantage of the present methods is the identification and use of a biocompatible matrix, which results in remodeling and patterning of stable vascular networks. Hence, the present methods eliminate many of the present short comings marring existing methods for forming blood vessels.

In one embodiment of the present disclosure, a method for forming stable three-dimensional blood vessels is provided that includes culturing an endothelial cell including an exogenous nucleic acid encoding the ETV2 transcription factor on a matrix such that the endothelial cell expresses the ETV2 transcription factor protein for at least 3 weeks.

Exogenous expression of the ETV2 transcription factor protein in differentiated endothelial cells reprograms differentiated endothelial cells, providing them with the ability to self-assemble into stable, functional, three-dimensional vascular structures, such as lumenized blood vessels, which can then be isolated and used for any number purposes such as, for example vascularization of injured tissue, vascularization of an organoid, or revascularization of a decellularized organ. Therefore, in some embodiments, the endothelial cell(s) for use in the present methods are differentiated endothelial cell(s). In certain embodiments, the differentiated endothelial cell is a human endothelial cell. In specific embodiments, the differentiated human endothelial cell is a human umbilical vein derived endothelial cell (HUVEC), a human adipose derived endothelial cell, or a tissue/organ specific human endothelial cell. In some embodiments of the present methods the differentiated endothelial cells are organ-specific endothelial cells including, but not limited to, endothelial cells of the heart, kidney, testis, ovary, retina, liver, pancreas, brain, lungs, spleen, large or small intestine. In other embodiments, the differentiated endothelial cells are tissue specific endothelial cells from muscle, lymph tissue, olfactory tissue, osteogenic tissue, oral (dental) tissue, or glandular tissue (e.g., endocrine, thymic).

In certain embodiments of the present methods, an exogenous ETV2 encoding nucleic acid is present in an endothelial cell. In one embodiment, the exogenous ETV2 encoding nucleic acid corresponds to the human ETV2 gene nucleotide sequence set forth in SEQ ID NO: 1, which encodes the human ETV2 transcription factor protein having an amino acid sequence as set forth in SEQ ID NO: 2. In other embodiments, the exogenous ETV2 encoding nucleic acid is an ETV2 ribosomal nucleic acid (RNA) transcript that encodes the ETV2 transcription factor protein.

In certain embodiments, the exogenous ETV2 nucleic acid is provided to an endothelial cell by transfection or transduction. In a specific embodiment, the nucleic acid encoding ETV2 is transduced into an endothelial cell using a viral vector, such as lentiviral vector. In one embodiment, the exogenous ETV2 transcription factor encoding nucleic acid is provided to a differentiated endothelial cell using an inducible expression system such as, for example, the reverse tet-transactivator (rtTA)-doxycycline inducible expression system.

In some embodiments, the present methods include culturing an endothelial cell including the exogenous ETV2 encoding nucleic acid under conditions that express the ETV2 transcription factor protein. The ETV2 protein can be expressed constitutively or transiently. In certain instances, the exogenous ETV2 transcription factor is expressed in a differentiated endothelial cell for at least 3 weeks, at least 4 weeks, at least 5 weeks, at least six weeks, at least 7 weeks, at least 8 weeks or more to reprogram the differentiated endothelial cell and induce lumenized blood vessels formation. In a specific embodiment, exogenous ETV2 protein is expressed for at least 3-4 weeks to induce blood vessel formation.

In other embodiments, the present methods include culturing an endothelial cell having an exogenous ETV2 encoding nucleic acid under conditions that express the ETV2 transcription factor protein, followed by a further culturing period under conditions where the endothelial cell does not express exogenous ETV2. Here, the endothelial cell can first be cultured under conditions that express exogenous ETV2 transcription factor for a first period of time, then undergo a second culturing under conditions that do not express exogenous ETV2 such as in the absence of a substance capable of activating an inducible promoter (e.g., doxycycline, tetracycline). In some instances, the present methods include culturing an endothelial cell having an exogenous ETV2 encoding nucleic acid under conditions that transiently express the ETV2 transcription factor protein (e.g., in the presence of doxycycline) for a period of at least 3 weeks, at least 4 weeks, at least 5 weeks, at least six weeks, at least 7 weeks, at least 8 weeks or more, followed by a second culture under conditions that do not express exogenous ETV2, such as in the absence of doxycycline for a period of days, weeks or months.

In some embodiments of the present methods, the endothelial cells including an exogenous ETV2 encoding nucleic acid are cultured on a matrix. In certain embodiments, the matrix in composed of defined extracellular matrix components, such as laminin, entactin and collagen. In specific embodiments, the matrix used in the present methods is composed of a combination of laminin, entactin and collagen IV (L.E.C.). In one embodiment, a matrix can include laminin and entactin at a combined concentration of at least 5 mg/mL. In an exemplary embodiment, ETV2 expressing endothelial cells are cultured on a matrix including laminin and entactin at a combined concentration of 5 mg/mL. Since laminin and entactin can bind to each other and form a complex, a matrix can include a complex of laminin and entactin. For example, the matrix can include at least 5 mg/mL of a complex of laminin and entactin. For example, the endothelial cells can be cultured on a matrix containing a complex of laminin and entactin at a concentration of at least 5 mg/mL, and at least 0.2 mg/mL collagen IV to form long-lasting, functional three-dimensional artificial blood vessels. In a specific embodiment, the endothelial cells are cultured on a matrix composed of laminin and entactin at a combined concentration of 5.25 mg/mL and 0.2 mg/mL collagen IV. In other embodiments, the matrix is Matrigel™ (Corning).

In one embodiment of the present methods, the endothelial cells including an exogenous ETV2 encoding nucleic acid are cultured in serum free media. In some embodiments, the present methods include culturing the endothelial cells in serum free media for at least 7 days, at least 10 days, at least 2 weeks, at least 3 weeks, at least 4 weeks, at least 5 weeks, at least 6 weeks, at least 7 weeks, at least 8 weeks or more. In other embodiments, the present methods include culturing the endothelial cells including an exogenous ETV2 encoding nucleic acid in serum free media at low oxygen tension, i.e., less than atmospheric oxygen tension (20% oxygen tension). In specific embodiments, the cells are cultured in serum free media at an oxygen tension from between 4% and 15%, 5% and 10%, 4% and 8%, or 4% and 6%. In one embodiment, the cells are cultured in serum free media at an oxygen tension of 5% for at least 7 days.

In some embodiments, the present methods include culturing an endothelial cell including an exogenous ETV2 encoding nucleic acid on a matrix under conditions that express an ETV2 transcription factor to induce the formation of a lumenized, stable three-dimensional blood vessel and isolating the stable three-dimensional blood vessel.

The present disclosure also reveals that exogenous expression of ETV2 protein in differentiated endothelial cells leads to the autonomous self-assembly of stable, functional, three-dimensional blood vessels that have the capacity to form functional vascular networks in vitro and in vivo in the absence of pericytes, perfusion, and a scaffold.

As such, in another aspect of the present disclosure a stable, three-dimensional blood vessel capable of autonomously forming a three-dimensional vascular network is provided.

In certain embodiments, the stable three-dimensional blood vessel of the present disclosure includes a tubular structure, such as a lumenized vessel composed of at least one contiguous layer of reprogrammed endothelial cells. In some embodiments, the reprogrammed endothelial cells contain an exogenous ETV2 transcription factor encoding nucleic acid.

In certain embodiments the endothelial cells of the stable three-dimensional blood vessel express the exogenous ETV2 transcription factor encoding nucleic acid. In one embodiment the expression of ETV2 transcription factor is transient, i.e., for a finite period of time, such as for a period of days, weeks or months. In specific embodiments, transient expression of the ETV2 transcription factor is modulated by an inducible expression system such as, for example, the reverse tet-transactivator (rtTA)-doxycycline inducible expression system. In other embodiments, the stable three-dimensional blood vessel of the present disclosure contains endothelial cells that constitutively (i.e., permanently) express exogenous ETV2 transcription factor. In other embodiments, the stable three-dimensional blood vessel is composed of a combination of endothelial cells that express exogenous ETV2 transcription factor and endothelial cells that do not express exogenous ETV2. In yet another embodiment, the stable three-dimensional blood vessel is composed of reprogrammed endothelial cells that do not express exogenous ETV2 transcription factor.

In some embodiments, the stable three-dimensional blood vessel of the present disclosure is isolated. Here, the blood vessel is removed, in-whole or in-part, from the environment from which it has been formed. In certain embodiments, an isolated stable three-dimensional blood vessel is free of culture media, culture media components and additives, and any matrix on which it has been formed, e.g., Matrigel™ or L.E.C matrix. In other embodiments the isolated stable, three-dimensional blood vessel of the present disclosure has been removed from the culture media, culture media components and additives, but includes at least a portion of matrix, such as, for example, a Matrigel™ or L.E.C matrix.

In one embodiment of the present disclosure the stable three-dimensional blood vessel is functional. In specific embodiments, the functional, stable three-dimensional blood vessel is capable of passing fluid (perfusing) through the vessel. In other embodiments, the functional stable three-dimensional blood vessel is capable of passing blood through the vessel. In yet another embodiment, the functional, stable three-dimensional blood vessel is capable of forming a three-dimensional vascular network. In one embodiment, the stable three-dimensional blood vessel forms a functional three-dimensional vascular network that includes at least one capillary, at least one arteriole, at least one venule, at least one lymphatic blood vessel or a combination thereof that is capable of transporting blood to a tissue (vascularizing tissue).

In some embodiments, the functional stable three-dimensional blood vessel of the present disclosure is functional for at least one month, at least 2 months, at least 3 months, at least 4 months, at least 5 months or more. In specific embodiments, the stable three-dimensional blood vessels of the present disclosure are stable for 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks or more post vessel formation.

Since the present disclosure shows that endothelial cells including exogenous ETV2 autonomously organize into patterned, stable artificial blood vessels capable of vascularizing in vivo the present disclosure also provides a method for promoting vascularization. Hence, in another aspect, a method for promoting vascularization in a subject is provided that includes administering to the subject a stable three-dimensional blood vessel. In some embodiments, the subject has injured tissue, such as an organ in need of vascularizing. In specific embodiments, the subject has injured heart tissue, injured liver tissue, injured lymphatic tissue, injured renal tissue, injured testicular tissue, injured ovarian tissue, an injured retina, injured pancreatic tissue, injured brain tissue, injured lung tissue, injured intestinal tissue, injured glandular tissue, injured muscle tissue or a combination thereof.

In one embodiment, the present methods include administering a stable three-dimensional blood vessel to the subject by surgical implantation to an injured tissue of the subject that is in need of vascularization. In specific embodiments, the stable three-dimensional blood vessel is implanted directly on an injured organ or tissue thereof. In other embodiments, the present methods include administering the stable three-dimensional blood vessel to a subject by injection such as, for example, injection directly to the injured tissue. In certain embodiments, a stable three-dimensional blood vessel is administered to the subject by intravenous injection, intraperitoneal injection, intramuscular injection, subcutaneous injection, or a combination thereof.

In some embodiments, the method of promoting vascularization in a subject includes administering to the subject at least one stable three-dimensional blood vessel that has been formed in vitro. In other embodiments, the method includes administration of 2 or more stable three-dimensional blood vessels of the present disclosure that have been formed in vitro. In a specific embodiment, the present methods include administration of a plurality of stable three-dimensional blood vessels on a matrix composed of laminin, entactin and collagen IV directly to a tissue in need of vascularization, such as an injured tissue.

Once a stable three-dimensional blood vessel has been administered to a subject the functional stable three-dimensional blood vessel establishes a three-dimensional vascular network, capable of vascularizing endogenous tissue. In some embodiments, the stable three-dimensional blood vessel forms a three-dimensional vascular network that includes at least one capillary, at least one arteriole, at least one venule, at least one lymphatic blood vessel or a combination thereof that is capable of transporting blood to a tissue.

In another aspect of the present disclosure, a method for vascularizing an organoid is provided. Here, the method for vascularizing an organoid includes culturing an organoid with an endothelial cell including an exogenous nucleic acid encoding ETV2 transcription factor on a matrix under conditions that express exogenous ETV2 protein in the endothelial cell to form a stable, three-dimensional vascular network on the organoid.

In some embodiments, the method for vascularizing an organoid includes culturing the organoid with endothelial cells on a matrix. In certain embodiments, the matrix in composed of defined extracellular matrix components, such as laminin, entactin and collagen. In specific embodiments, the matrix used in the present methods is composed of a combination of laminin, entactin and collagen IV (L.E.C.). In one embodiment, a matrix can include laminin and entactin at a combined concentration of at least 5 mg/mL. In an exemplary embodiment, the organoid is cultured with endothelial cells on a matrix including laminin and entactin at a combined concentration of 5 mg/mL. Since laminin and entactin can bind to each other and form a complex, a matrix can include a complex of laminin and entactin. For example, the matrix can include at least 5 mg/mL of a complex of laminin and entactin. For example, the endothelial cells can be cultured on a matrix containing a complex of laminin and entactin at a concentration of at least 5 mg/mL, and at least 0.2 mg/mL collagen IV vascularize the organoid. In a specific embodiment, the matrix is composed of laminin and entactin at a combined concentration of 5.25 mg/mL and 0.2 mg/mL collagen IV. In other embodiments, the matrix is Matrigel™ (Corning).

In one embodiment, the method for vascularizing an organoid includes culturing the organoid with endothelial cells on a matrix in culture media that includes fibroblast growth factor (FGF). In a specific embodiment, the culture media includes basic fibroblast growth factor (FGF2). In some embodiments, the culture media includes heparin. In a specific embodiment, the method for vascularizing an organoid includes culturing the organoid with endothelial cells on a matrix in a culture media including FGF2 and heparin.

The organoids and endothelial cell including an exogenous nucleic acid encoding ETV2 transcription factor can be cultured on a matrix under conditions that express exogenous ETV2 protein in the endothelial cell for any period of time necessary to induce the formation of a functional three-dimensional vascular network on the organoid, i.e., vascularize the organoid. For example, in certain embodiments, the organoid and differentiated endothelial cell(s) are cultured for at least a week (7 days), at least 10 days, at least 2 weeks, at least 3 weeks, at least 4 weeks, at least 5 weeks, at least 6 weeks, at least 7 weeks, at least 8 weeks or more to reprogram the endothelial cells and induce the formation of patterned, long-lasting artificial vessels on the organoid. In some embodiments, the vascularized organoid has a three-dimensional vascular network that includes at least one capillary, at least one arteriole, at least one venule, at least one lymphatic blood vessel or a combination thereof that is capable of transporting blood throughout the organoid.

The present methods for vascularizing an organoid can be applied to any type of organoid. For example, an organoid for use in the present methods can be a small intestine organoid, colon organoid, kidney organoid, heart organoid or a tumor organoid. In some embodiments, the methods can be used to vascularize a tumor organoid, whereby the tumor organoid can be tissue specific such as a breast cancer organoid, a colon cancer organoid, a renal cancer organoid, or an intestinal cancer organoid.

The vascularized organoids of the present disclosure can be used by one of ordinary skill in the art for any number of purposes. As such, in some embodiments, the present methods for vascularizing an organoid includes isolating the vascularized organoid.

Once a vascularized organoid is obtained, the vascularized organoid can be administered to a subject, such as a human or an animal (e.g., mouse, rat, dog, monkey). In specific embodiments, the vascularized organoid can be administered to a mouse by surgical implantation.

In other embodiments, the isolated vascularized organoid can be used to determine the efficacy of a therapeutic agent. Here, the vascularized organoid is contacted with a therapeutic agent and cultured for a period of time in the presence of the therapeutic agent. During culture, organoid function, cellular growth and health can then be analyzed to determine the efficacy of the therapeutic agent.

The present disclosure also reveals that culturing a decellularized organ with endothelial cells including an exogenous nucleic acid encoding ETV2 transcription factor under conditions that express exogenous ETV2 protein in the endothelial cells results in the development of functional vascular structures on the decellularized organ. As such, one aspect of the present disclosure provides a method for revascularizing a decellularized organ.

In some embodiments, the method for revascularizing a decellularized organ includes culturing the decellularized organ with reprogrammed endothelial cells on a matrix. In specific embodiments, the matrix used in the present methods is composed of a combination of laminin, entactin and collagen IV (L.E.C.). In certain embodiments, the matrix in composed of defined extracellular matrix components, such as laminin, entactin and collagen. In one embodiment, a matrix can include laminin and entactin at a combined concentration of at least 5 mg/mL. In an exemplary embodiment, the organ is cultured with endothelial cells on a matrix including laminin and entactin at a combined concentration of 5 mg/mL. The matrix can include at least 5 mg/mL of a complex of laminin and entactin. For example, the endothelial cells can be cultured on a matrix containing a complex of laminin and entactin at a concentration of at least 5 mg/mL, and at least 0.2 mg/mL collagen IV vascularize the organ. In a specific embodiment, the matrix is composed of laminin and entactin at a combined concentration of 5.25 mg/mL and 0.2 mg/mL collagen IV. In other embodiments, the matrix is Matrigel™ (Corning).

In some embodiments, the method for revascularizing a decellularized organ includes culturing the decellularized organ in a bioreactor with endothelial cells on a matrix under conditions that express exogenous ETV2 transcription factor protein.

In one embodiment, the method for revascularizing a decellularized organ includes culturing the decellularized organ with endothelial cells on a matrix under conditions that express exogenous ETV2 protein in the endothelial cells for any period of time necessary to induce the formation of a functional three-dimensional vascular network on the decellularized organ, i.e., revascularize the organ. For example, in certain embodiments, the decellularized organ and reprogrammed endothelial cell(s) are cultured for at least a week (7 days), at least 10 days, at least 2 weeks, at least 3 weeks, at least 4 weeks, at least 5 weeks, at least 6 weeks, at least 7 weeks, at least 8 weeks or more to induce the endothelial cells to organize into lumenized, long-lasting vessels on the decellularized organ. In other embodiments, the endothelial cells form a functional three-dimensional vascular network on the decellularized organ that includes at least one capillary, at least one arteriole, at least one venule, at least one lymphatic blood vessel or a combination thereof that is capable of transporting blood throughout the organ.

The present methods can be applied to any type of decellularized organ. For example, an endothelial cell can be cultured under conditions that express exogenous ETV2 protein in the endothelial cells on a decellularized organ, such a decellularized heart, kidney, testis, ovary, retina, bone, endocrine gland, thyroid gland, trachea, lymph node, liver, pancreas, brain, lung, spleen, large intestine or small intestine.

The revascularized organs of the present disclosure can be used by one of ordinary skill in the art for any number of purposes. As such, in some embodiments, the present methods for revascularizing decellularized organs includes isolating the revascularized organ. In an exemplary embodiment, the revascularized organ can be isolated and then administered to a subject, such as a human or an animal (e.g., mouse, rat, dog, monkey). In specific embodiments, the revascularized decellularized organ is isolated and be administered to a human subject by surgical implantation.

In other embodiments, the isolated revascularized decellularized organ can be used to determine the efficacy of a therapeutic agent. Here, the revascularized decellularized organ is contacted with a therapeutic agent and cultured for a period of time in the presence of the therapeutic agent. During culture, the organs function, cellular growth and health can then be analyzed to determine the efficacy of the therapeutic agent.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE DISCLOSURE

Figures 1A, 1B, 1C:
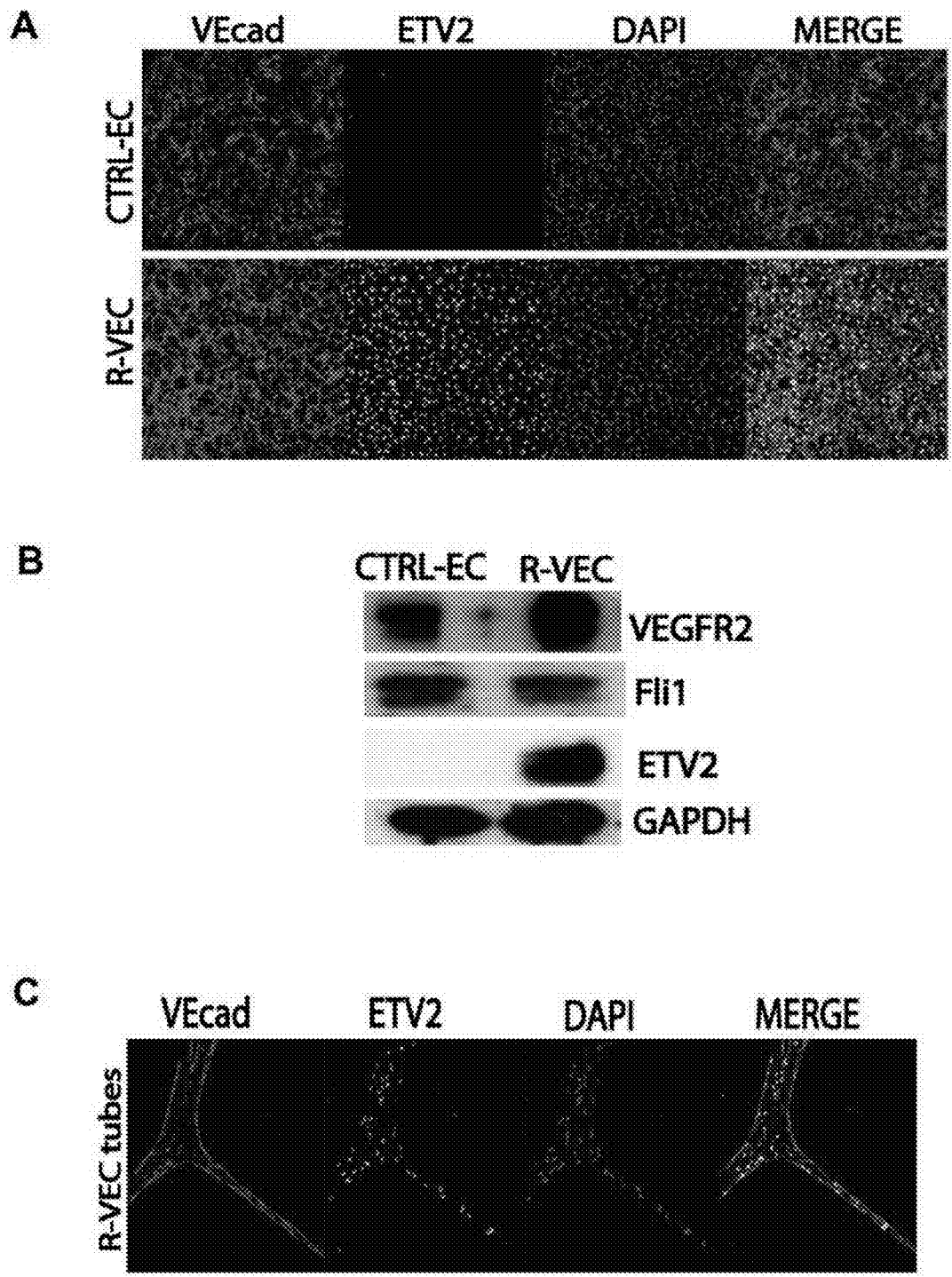
FIGS. 1A-1M. Reprogrammed endothelial cells including exogenous ETV2 self-assemble into stable, three-dimensional, functional and lumenized artificial blood vessels in vitro. A. Monolayers of Control-HUVEC (CTRL-EC) or lenti-ETV2 transduced HUVECs were stained for VECAD, ETV2 and DAPI (R-VEC). B. Western Blot analysis of control-ECs or R-VECs for ETV2, VEGFR2 and the transcription factor Fli1. GAPDH was used as a loading control. C. Immunostaining for VECAD and ETV2 on 12 week tubes formed by endothelial cells that express exogenous ETV2 (R-VEC). D. Images of a time course of tube formation from 24 hours to 8 weeks for both CTRL-EC and R-VEC. E. An overview of a whole well of R-VEC vessels at week 16, demonstrating presence of organized vascular plexus. F. Quantification of vessel density at various time points through 12 weeks of culture. G. Quantification of vessel formation when using R-VEC or ETS1 or myrAKT transduced endothelial cells. H. Representative image for ETS1 or myrAKT1 transduced HUVECs in a vessel formation assay on Matrigel. I. Immunostaining of artificial vessels formed by endothelial cells that express exogenous ETV2 (R-VEC) for proper lumen polarity with podocalyxin (apical, in red) and laminin (basal, in green). J. Electron microscopy showing the presence of intact lumen artificial vessels formed by endothelial cells that express exogenous ETV2 at 8/12-week time points. K. Quantification of a screen of different mixtures of extra cellular matrix proteins at 1 week and 4 weeks for both CTRL-EC and R-VEC. L. Long-term vessel quantification of vessel formation on Matrigel™ (corning) or a laminin/entactin/collagenIV (L.E.C.) matrix using R-VEC through an 8 week time point. M. A lumen is present in artificial vessels formed by endothelial cells that express exogenous ETV2 (R-VEC) when both Matrigel™ as well as L.E.C. matrices are used, as shown by electron microscopy. ns=not significant, *P<0.05, P<0.01, *P<0.001.

It has been recognized herein that exogenous expression of ETS-transcription factor variant 2, ETV2 (ER71, ETSRP71) in endothelial cells (ECs) plays an essential role in reprogramming differentiated endothelial cells to more primitive endothelial cells that are capable of autonomously forming functional, stable three-dimensional blood vessels and vascular networks. Accordingly, this disclosure provides methods for forming stable three-dimensional blood vessels by exogenously expressing ETV2 in endothelial cells in the absence of pericytes, forced perfusion and artificial scaffolding, the stable and functional three-dimensional artificial vessels produced by these methods, and methods for using the same.

Method for Forming Stable Three-Dimensional Blood Vessels.

A first aspect of the present disclosure is directed to methods for forming stable three-dimensional vascular structures, such as artificial blood vessels. Without being bound to any particular theory, it is believed that ETV2 expression in endothelial cells for an appropriate time can reprogram endothelial cells in culture to form long-lasting, functional three-dimensional blood vessels in vitro, as well as in vivo. Expression of exogenous ETV2 transcription factor in differentiated endothelial cells when culturing on a defined matrix results in autonomous formation of functional, stable, three-dimensional blood vessels. Since the present method does not utilize a three-dimensional scaffold, the methods provided herein advantageously eliminate costly and time-consuming elements presently required for forming three-dimensional vessels.

Generally, the instant method for forming stable three-dimensional blood vessels includes culturing an endothelial cell including an exogenous nucleic acid encoding the ETV2 transcription factor on a biocompatible matrix under conditions that express exogenous ETV2 transcription factor for at least 3 weeks. Exogenous expression of the ETV2 transcription factor protein in differentiated endothelial cells reprograms the differentiated endothelial cells, conferring the cells with the ability to self-assemble into stable, functional three-dimensional vascular structures, such as lumenized blood vessels, which can then be isolated and used for any number purposes such as, for example vascularization of injured tissue, vascularization of an organoid, or revascularization of a decellularized organ.

In one embodiment, the endothelial cell for use in the present methods is a differentiated endothelial cell (EC). The term "differentiated" or "differentiated endothelial cell" as used herein refers to a developmental process whereby an endothelial cell becomes specialized for a particular function, for example, where cells acquire one or more morphological characteristics and/or functions different from that of the initial cell type. The term "differentiation" includes both lineage commitment and development of a cell into a mature, fully differentiated adult endothelial cell. Differentiation may be assessed, for example, by monitoring the presence or absence of lineage markers, using immunohistochemistry or other procedures known to one skilled in the art.

Endothelial cells can be obtained by methods known in the art. For example, endothelial cells can be isolated from tissue using a collagenase-based digestion approach as described in Ginsberg, M. et al. Cell (2012) 151, 559-575 and U.S. Pat. No. 6,899,822 to Ferrara et al. Endothelial lineage can be verified by staining with, for example, an anti-CD31 antibody, VE-cadherin or anti-von Willebrand factor antibody. Isolation of ECs can be achieved using antibodies specific for EC surface markers, such as VE-cadherin, CD31 or VEGFR2, attached to magnetic beads or fluorophores for use in Magnetic or Fluorescence Activated Cell Sorting (MACS or FACS).

In the alternative, endothelial cells may be obtained from commercial sources. Endothelial cells can be cultured and maintained (expanded) under conditions that maintain their differentiated lineage and the ability to replicate. Such conditions have been well documented in the art. For example, isolated endothelial cells can be cultured in coated tissue culture dishes in complete media including endothelial cell growth supplement. The endothelial cells can then be split and passaged until used.

In some embodiments, the differentiated endothelial cell is a human endothelial cell. In certain embodiments, the differentiated human endothelial cell is a human umbilical vein derived endothelial cell (HUVEC), a human adipose derived endothelial cell, or a tissue/organ specific human endothelial cell. In some embodiments of the present methods the differentiated endothelial cells are organ-specific endothelial cells including, but not limited to, endothelial cells of the heart, kidney, testis, ovary, retina, liver, pancreas, brain, lungs, spleen, large or small intestine. In other embodiments, the differentiated endothelial cells are tissue specific endothelial cells from muscle, lymph tissue, olfactory tissue, osteogenic tissue, oral (dental) tissue, or glandular tissue (e.g., endocrine, thymic).

A differentiated endothelial cell can be cultured to initiate the formation of stable three-dimensional blood vessels. Cells can be cultured in any culture medium capable of sustaining growth of endothelial cells such as, but not limited to, DMEM (high or low glucose), advanced DMEM, DMEM/MCDB 201, Eagle's basal medium, Ham's F10 medium (F10), Ham's F-12 medium (F12), Hayflick's Medium, Iscove's modified Dulbecco's medium, Mesenchymal Stem Cell Growth Medium (MSCGM), DMEM/F12, RPMI 1640, and CELL-GRO-FREE (Corning cellgro, Corning, NY). The culture medium can be supplemented with one or more components including, for example fetal bovine serum, preferably about 2-15% (v/v); equine serum; human serum; fetal calf serum; beta-mercaptoethanol, preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G, streptomycin sulfate, amphotericin B, gentamicin, and nystatin, either alone or in combination.

The endothelial cell can be cultured to expand the cell numbers, prior to reprogramming. Sufficient numbers of endothelial cells may be isolated from an initial sample; however, even if an acceptable number of differentiated endothelial cells are present in the initial sample, expansion of the cells in culture can provide an even greater supply of endothelial cells for reprogramming. Methods of culturing and expanding cells are known in the art. See, for example, Helgason et al., Basic Cell Culture Protocols, 4th Edition, Human Press Publishing, 2013; and Mitry et al, Human Cell Culture Protocols, 3rd Edition, Human Press Publishing, 2012.

The differentiated endothelial cells can be "reprogrammed" by the incorporation and expression of an exogenous ETV2 encoding nucleic acid by the differentiated endothelial cell.

An endothelial cell is "reprogrammed" (directed to de-differentiate into a more plastic state) according to the methods disclosed herein by expressing an exogenous ETV2 transcription factor protein, which alters the endothelial cell's ability to form tubular (lumenized) vessels and other vascular structures.

The term "ETV2" or "ETV2 transcription factor" are used interchangeably herein to refer to the human ETS-transcription factor variant 2, ETV2 (ER71, ETSRP71) set forth in RefSeq Gene ID 2116, NCBI Reference Sequence No. NC_000019.10, which encodes a DNA binding transcription factor protein having an amino acid sequence set forth in NP_055024. An ETV2 nucleic acid of the present disclosure can include the ETV2 DNA sequence or a portion thereof, as well as an RNA transcript thereof such as that set forth in Accession Nos: NM_001300974.1, NM_014209.3 and NM_001304549.1. Functional derivatives and homologs of ETV2 are further contemplated for use in the disclosed methods. As used herein, a "functional derivative" is a molecule that possesses the capacity to perform the biological function of ETV2. For example, a functional derivative of ETV2 as disclosed herein is a molecule that is able to bind DNA as the ETV2 transcription factor is and reprogram differentiated endothelial cells. Functional derivatives include fragments, variants, parts, portions, equivalents, analogs, mutants, mimetics from natural, synthetic or recombinant sources including fusion proteins. A "homolog" is a protein related to the ETV2 transcription factor by descent from a common ancestral nucleic acid sequence. Homologs contemplated herein include, but are not limited to, ETV2 proteins derived from different species, such as, for example, mouse, rat, and monkey.

In a specific embodiment of the present methods, the exogenous ETV2 encoding nucleic acid present in an endothelial cell is human ETV2 as set forth in SEQ ID NO: 1, which encodes the human ETV2 transcription factor protein set forth in SEQ ID NO: 2. In another embodiment, the exogenous ETV2 encoding nucleic acid present in an endothelial cell is a human ETV2 ribosomal nucleic acid (RNA) transcript, which encodes the human ETV2 transcription factor protein. In other embodiments, the exogenous ETV2 encoding nucleic acid provided to a differentiated endothelial cell is a modified synthetic RNA. Modified synthetic RNA molecules can be produced by methods known by one of ordinary skill in the art, such as those set forth in Machnicka, M A, et al. Nucleic Acids Res. (2013) 41 pp. D262-D267. Exemplary modified synthetic molecules for use in the present invention include chemical modifications to the RNA polynucleotide that modulate the stability (alter nuclease resistance) or cellular uptake (e.g., conjugation of the RNA polynucleotide to a cholesterol, linker, lipid, polymer, peptide or apamer).

The nucleic acid encoding ETV2 transcription factor can be provided to a cell by methods well known to those of ordinary skill in the art. For example, the ETV2 encoding nucleic acid can integrate the ETV2 nucleic acid sequence into the endothelial cell genome, or non-integrative, meaning the ETV2 gene is expressed from an extrachromosomal location. In some embodiments, the ETV2 encoding nucleic acid sequence is provided by a vector into which the nucleic acid sequence is cloned by techniques known in the art. The vector can be introduced by any suitable method, such as by transfection or by viral-mediated transduction.

Vectors for use in expressing the ETV2 transcription factor include, for example, retrovirus, lentivirus, adenovirus, adeno-associated virus, and other vectors that, once introduced into a cell, integrate into a chromosomal location within the genome of the subject and provide stable, long-term expression of ETV2. Other vectors include episomal vectors, as well as engineered lentivirus vector variants that are non-integrative. Here, the ETV2 nucleotide sequence can be cloned into the vector sequence; the vector is grown in differentiated endothelial cells, and used to reprogram the endothelial cells using the methods described herein.

In one embodiment, the ETV2 nucleic acid is included in a lentiviral vector and provided to an endothelial cell by lentivirus-mediated transduction. In a specific embodiment, the nucleic acid encoding ETV2 of SEQ ID NO: 1 is transduced into a differentiated endothelial cell using a lentiviral vector. In one embodiment, the lentiviral vector is lenti pgk-vector. In specific embodiments the exogenous ETV2 encoding nucleic acid of SEQ ID NO: 1 is provided to an endothelial cell by transduction with an inducible expression system such as, for example, the reverse tet-transactivator (rtTA)-doxycycline inducible expression system.

In other embodiments, the ETV2 nucleic acid is an RNA transcript that is delivered to an endothelial cell. In certain specific embodiments, the ETV2 RNA delivered to a cell is a modified synthetic RNA molecule. Methods for introducing RNA molecules to a cell are well known by those of ordinary skill in the art, and such methods can be used here. For example, an ETV2 RNA transcript such as an mRNA transcript can be delivered to an endothelial cell by transfections. In another non-limiting example, an ETV2 RNA transcript is delivered to a cell by electroporation.

The present methods include culturing a differentiated endothelial cell including the exogenous ETV2 encoding nucleic acid under conditions that express the ETV2 transcription factor protein. In certain embodiments, the ETV2 protein is expressed constitutively. In other embodiments, the ETV2 protein is expressed transiently, such as under the control of an inducible promoter. In certain embodiments, the exogenous ETV2 transcription factor is expressed in an endothelial cell for at least 3 weeks, at least 4 weeks, at least 5 weeks, at least six weeks, at least 7 weeks, at least 8 weeks, at least 9 weeks, at least 10 weeks, at least 11 weeks, at least 12 weeks or more to induce the endothelial cell(s) to form lumenized blood vessels. In a specific embodiment, exogenous ETV2 protein is expressed for at least 4 weeks to induce blood vessel formation. In another embodiment, the exogenous ETV2 protein is expressed for at least 3 to 4 weeks to induce lumen formation.

In other embodiments, the present methods include culturing an endothelial cell having an exogenous ETV2 encoding nucleic acid under conditions that express the ETV2 transcription factor protein, followed by a further culturing period under conditions where the endothelial cell(s) do not express exogenous ETV2. Here, the endothelial cell can first be cultured under conditions that express exogenous ETV2 transcription factor for a first period of time, then undergo a second culturing under conditions that do not express exogenous ETV2 such as in the absence of a substance capable of activating an inducible promoter (e.g., doxycycline, tetracycline). In one embodiment, the exogenous ETV2 encoding nucleic acid is a modified synthetic RNA molecule, which results in transient ETV2 transcription factor expression during culture.

In some embodiments, the present methods include culturing an endothelial cell having an exogenous ETV2 encoding nucleic acid under conditions that express the ETV2 transcription factor protein for a period of at least 3 weeks, at least 4 weeks, at least 5 weeks, at least six weeks, at least 7 weeks, at least 8 weeks, at least 9 weeks, at least 10 weeks, at least 11 weeks, at least 12 weeks or more, followed by a second culture under conditions that do not express exogenous ETV2, such as in the absence of doxycycline for a period of days, weeks or months. In a specific embodiment, the endothelial cell is cultured under conditions that express an exogenous ETV2 transcription factor protein for a period of at least 3 to 4 weeks, then the endothelial cell is cultured under conditions that do not express the ETV2 transcription factor for a period of time ranging from 7 days to 6 months, from 7 days to 5 months, from 7 days to 4 months, from 7 days to 3 months, from 7 days to 2 months, or from 7 days to 1 month. Regardless of the amount of time that reprogrammed endothelial cells are cultured under conditions that express ETV2 protein, the endothelial cells will continue to develop stable, functional three-dimensional vascular structures such as blood vessels as shown in FIGS. 4A-4H.

The present methods include culturing the endothelial cells containing an exogenous ETV2 encoding nucleic acid on a matrix. In fact, the present disclosure identifies essential extracellular matrix components, i.e., laminin, entactin and collagen IV, which when used to culture reprogrammed endothelial cells results in the formation of stable and functional three-dimensional artificial vessels in vitro and in vivo without the use of periocytes, perfusion and cumbersome scaffolds. Therefore, in certain embodiments, the matrix is composed of extracellular matrix components, such as laminin, entactin and/or collagen.

In one embodiment, a matrix for use in the present methods can include laminin and entactin at a combined concentration of at least 5 mg/mL. As laminin and entactin can bind to each other and form a complex, a matrix for use in the present methods can include a complex of laminin and entactin. For example, the matrix can include at least 5 mg/mL of a complex of laminin and entactin. In an exemplary embodiment, ETV2 expressing endothelial cells are cultured on a matrix including laminin and entactin at a combined concentration of 5 mg/mL. In specific embodiments, the matrix used in the present methods is composed of a combination of laminin, entactin and collagen IV (L.E.C.). For example, the endothelial cells can be cultured on a matrix containing at least 5 mg/mL of laminin and entactin, and at least 0.2 mg/mL collagen IV to form long-lasting, functional three-dimensional artificial blood vessels. In a specific embodiment, the endothelial cells are cultured on a matrix composed of laminin and entactin at a combined concentration of 5.25 mg/mL and 0.2 mg/mL collagen IV. In other embodiments, the matrix is Matrigel™ (Corning).

Methods for determining the concentration of substances (e.g., molecules and proteins, or complexes thereof) in a solution or material are known by those of skill in the art. For example, spectrophotometry can be used to determine the concentration of a substance in a sample.

In one embodiment of the present methods, the endothelial cells including an exogenous ETV2 encoding nucleic acid are cultured in serum free media for a period of time.

In some embodiments, the present methods include culturing the endothelial cells in serum free media for at least 7 days, at least 10 days, at least 2 weeks, at least 3 weeks, at least 4 weeks, at least 5 weeks, at least 6 weeks, at least 7 weeks, at least 8 weeks or more.

In other embodiments, the present methods include culturing the endothelial cells including an exogenous ETV2 encoding nucleic acid are cultured in serum free media at low oxygen tension. In some embodiments, the endothelial cells are cultured in serum free media at less than atmospheric oxygen tension, i.e, 20%. In specific embodiments, the cells are cultured in serum free media at an oxygen tension from between 4% and 15%, 5% and 10%, 4% and 8% or 4% and 6%. In one embodiment, the cells are cultured in serum free media at an oxygen tension of 5%. In a specific embodiment, the present method includes culturing the endothelial cells including an exogenous ETV2 encoding vector in serum free media at an oxygen tension of 5% for 7 days.

Regardless of the duration or specific culture conditions, the present methods include culturing an endothelial cell including an exogenous ETV2 encoding nucleic acid on a matrix under conditions that express an ETV2 transcription factor to induce the formation of a lumenized, stable, functional, three-dimensional blood vessel and isolating the same.

By "stable" it is meant that the three-dimensional vessel maintains its structure and function for an extended period of time, e.g., at least one month, at least 2 months, at least 3 months, at least 4 months, at least 5 months, at least 6 months or more. A stable three dimensional blood vessel means a tubular structure of endothelial cells having an intact lumen, display proper apical-basal polarity, and maintain a tubular (lumenized) structure for at least one month without collapsing, puncturing or dissociating, and without the use of a scaffold, enforced perfusion or perivascular support.

The term "functional" as used herein means that a stable three-dimensional blood vessel can carry out the processes typically conducted by natural (endogenous) blood vessels. For example, a functional blood vessel of the present disclosure can perfuse fluid such as blood, anastomose to other vessels (e.g., capillaries, veins, arteries, arteriole, venule or lymphatic vessel) or tissue, autonomously form an integrated patterned (branched) network of blood vessels on a tissue, such that blood and/or fluid can be supplied to the tissue ("vascularize") without the use of a scaffold, enforced perfusion or a perivascular support.

Figures 1D, 1E, 1F:
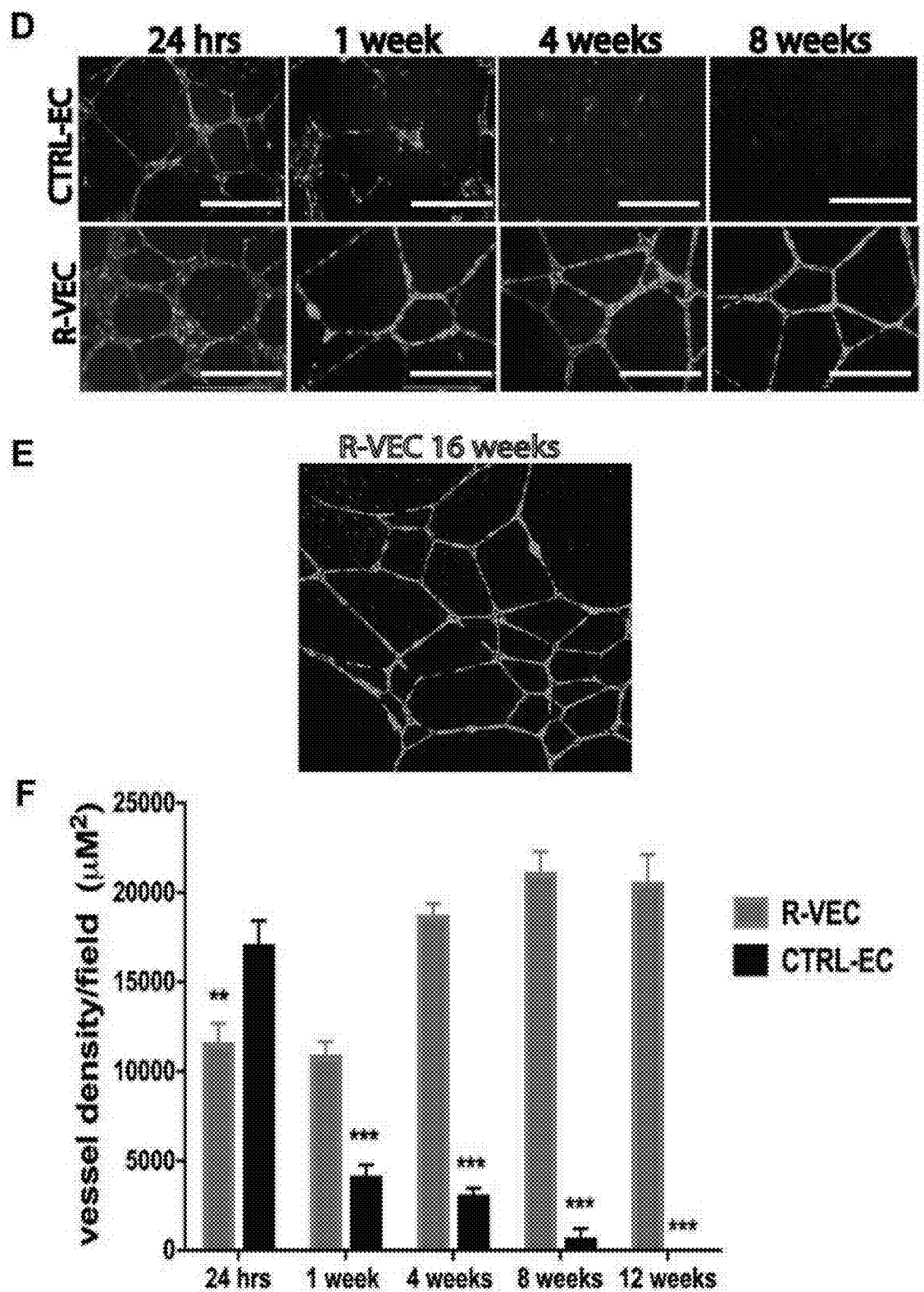
Figure 2A:
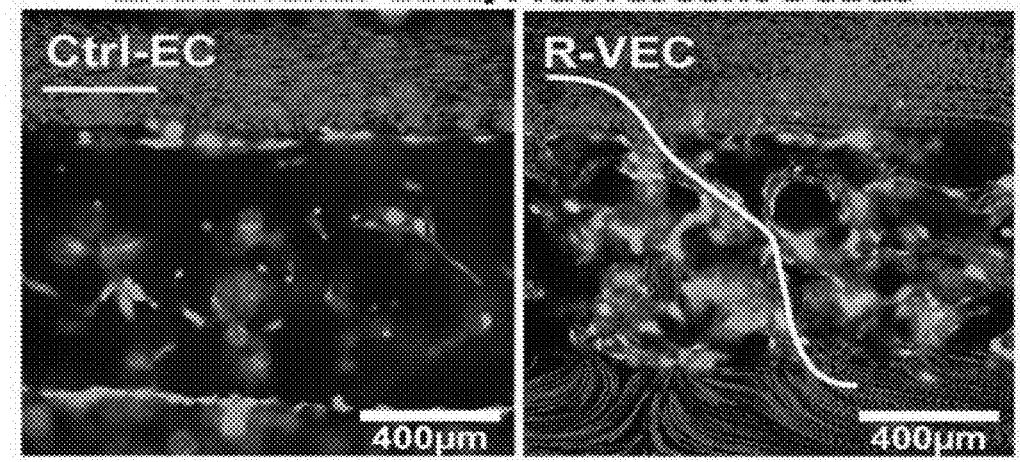
FIGS. 2A-2B. Stable, three-dimensional blood vessels are functional in vitro. A. Vessel durability and functionality was shown by perfusion with red fluorescent labeled beads. B. Quantification of vessel density at day 6 post culturing in a microfluidic device. *P<0.05.
Figure 2B:
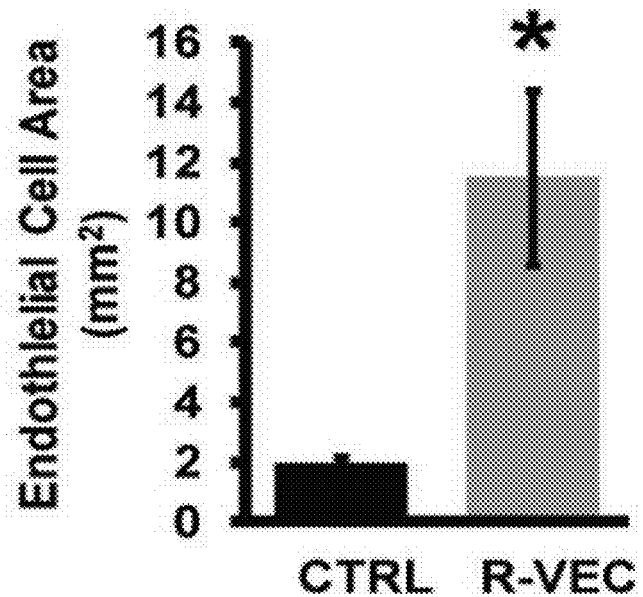
Figures 3A, 3B, 3C:
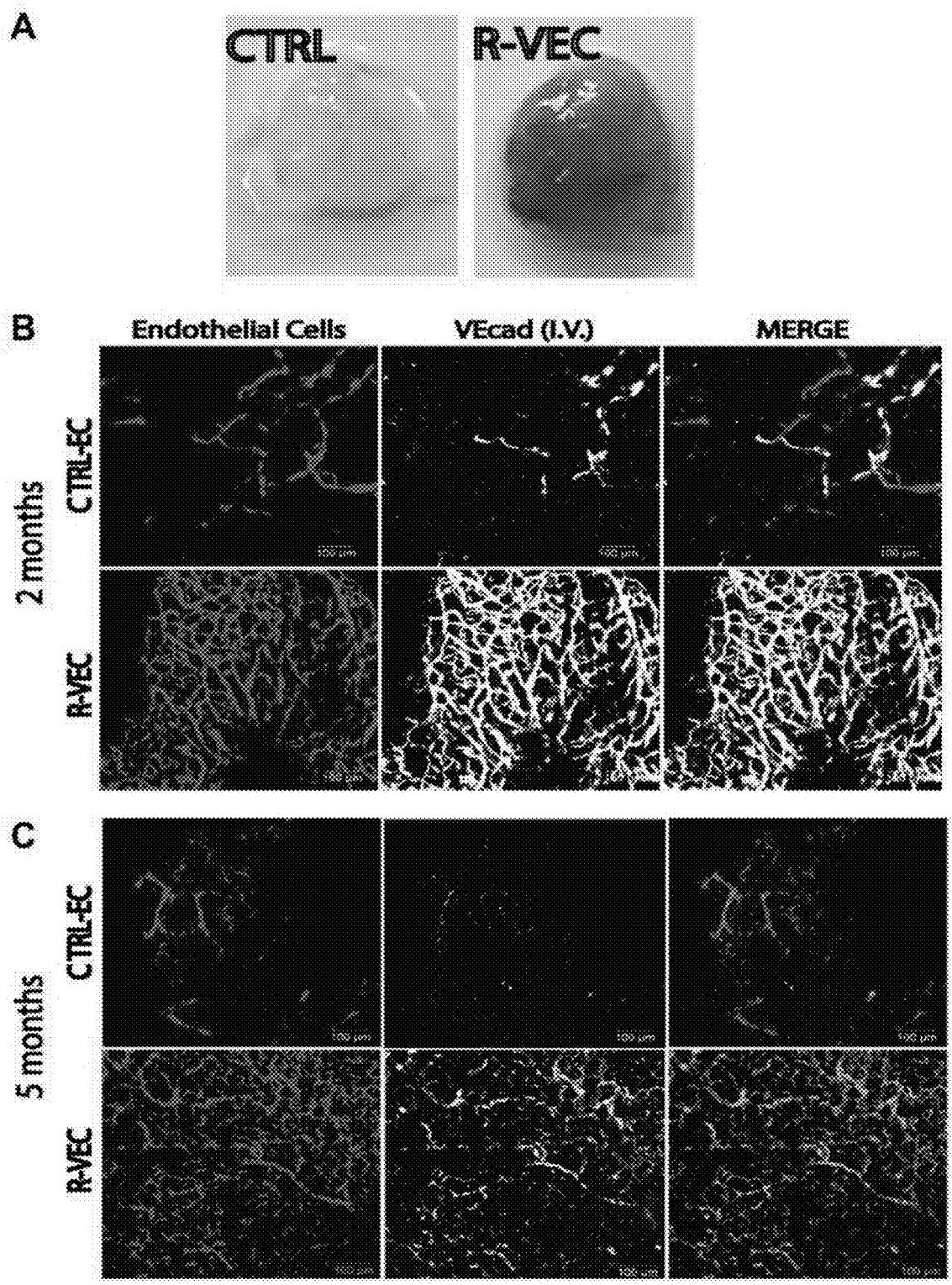
FIGS. 3A-3M. Endothelial cells including exogenous ETV2 organize into patterned, long-lasting blood vessels capable of vascularizing in vivo. A. Images of plugs containing CTRL-EC and reprogrammed endothelial cells expressing ETV2 (R-VEC) at 2 months. B-C. Whole mount confocal images of plugs including Laminin/Entactin/Collagen IV (L.E.C) matrix and endothelial cells were isolated at a 2 month time point and a 5 month time point and R-VEC plugs were compared to CTRL-EC containing plugs. Monoclonal VECAD antibody specific to human endothelial cells and conjugated to Alexa647 (white) was injected retroorbitally (intravital injection) in mice before sacrifice. D. Quantification of vessel density measured as percent fluorescence intensity in sections at one and two months. E. Whole mount images of plugs at 1 week, 1 month and 2 months. F. Quantification of vessels formed in R-VEC and CTRL-EC plugs at 1 week, 1 month and 2 month time points. G. H&E staining of sections of plugs at two months. H. Immunofluorescent staining of sections (20 μm) of plugs at two months. Vessels formed in a plug stained for mouse PDGFRβ. I. Images of Matrigel™ plugs at a 1 month time point obtained from plugs with R-VEC, ETS1-expressing endothelial cells (ETS1-VEC) or myrAKT1-expressing endothelial cells (myrAKT1-EC) and CTRL-EC. J. Whole mount microscopy at 1 month of R-VEC, ETS1-VEC or myrAKT1-EC and CTRL-EC. K. H&E staining of R-VEC, ETS1-VEC or myrAKT1-EC and CTRL-EC at 1 month. Only reprogrammed endothelial cells (R-VEC plugs) formed perfused and patterned vessels as indicated by the presence of red blood cells. L. Stained sections of implanted vessels (human VECAD, blue) mouse pericytes (mouse PDGFRβ, green). Images of smaller capillaries and arteriole like structures. M. Implanted R-VEC vessels, which are wrapped by mouse PDGFRβ positive pericytic cells in vivo. Panels (i and ii) zoomed in images from FIG. 3L. Panel (iii) 3D reconstruction of implanted R-VEC vessels. ns=not significant, *P<0.05, P<0.01, *P<0.001.
Figure 3D:
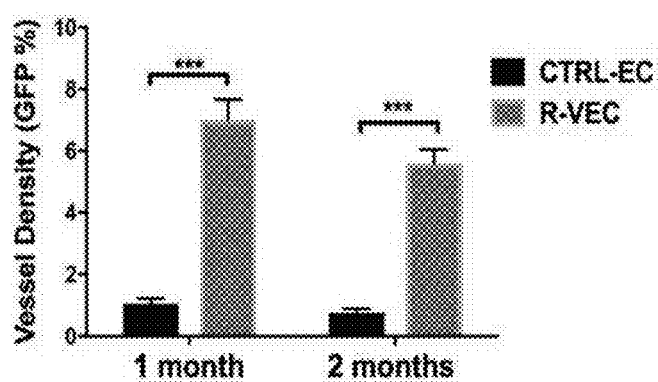
Figure 3E:
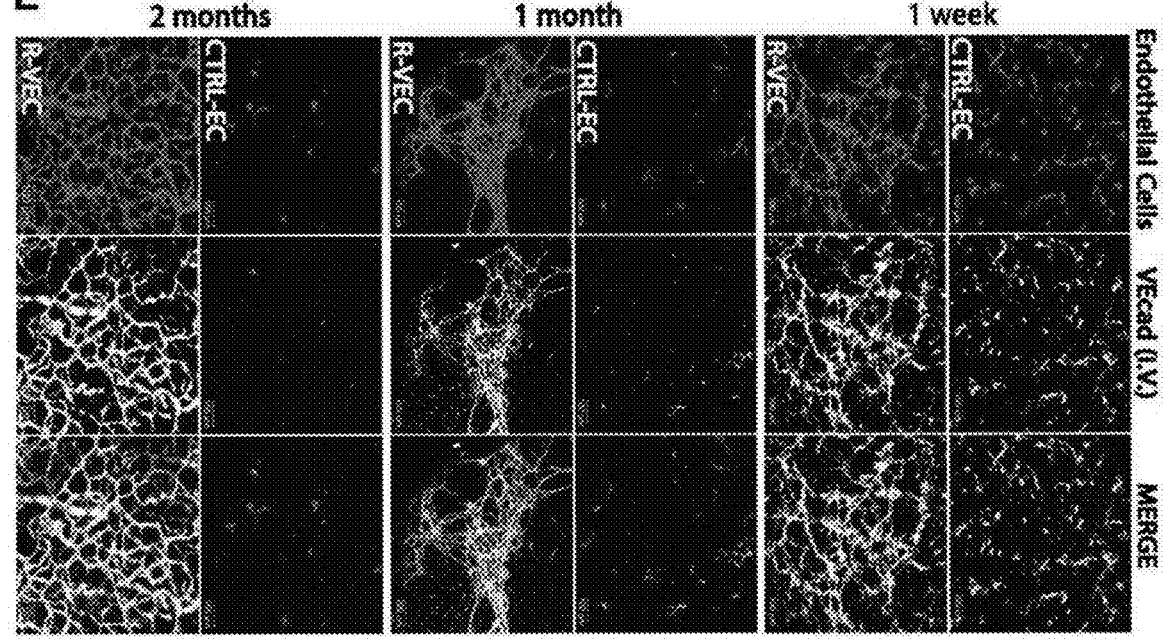
Figure 3F:
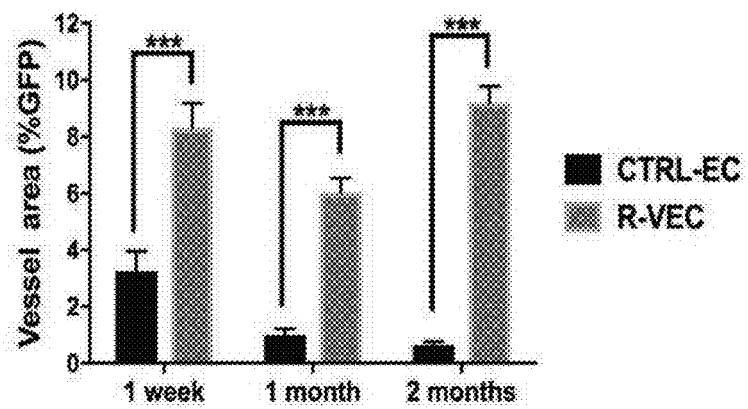
Figure 3G:
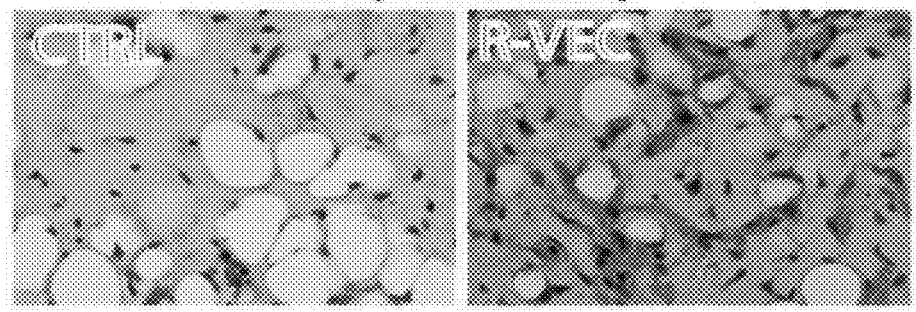
Figure 3H:
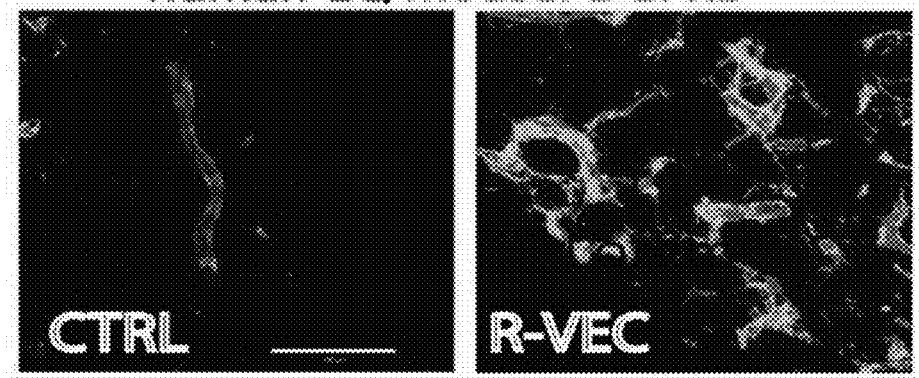
Figure 3I:
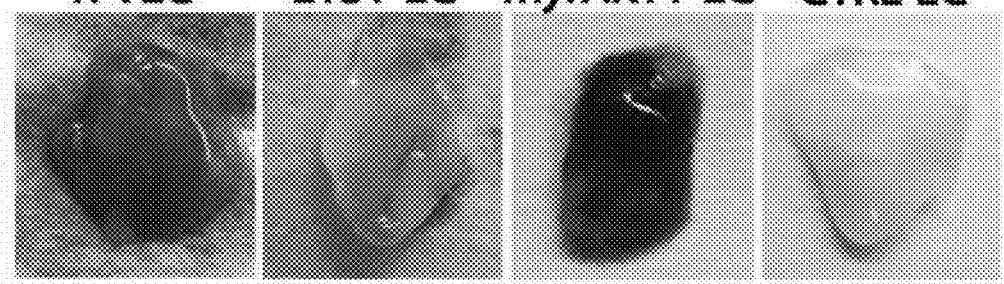
Figure 3J:
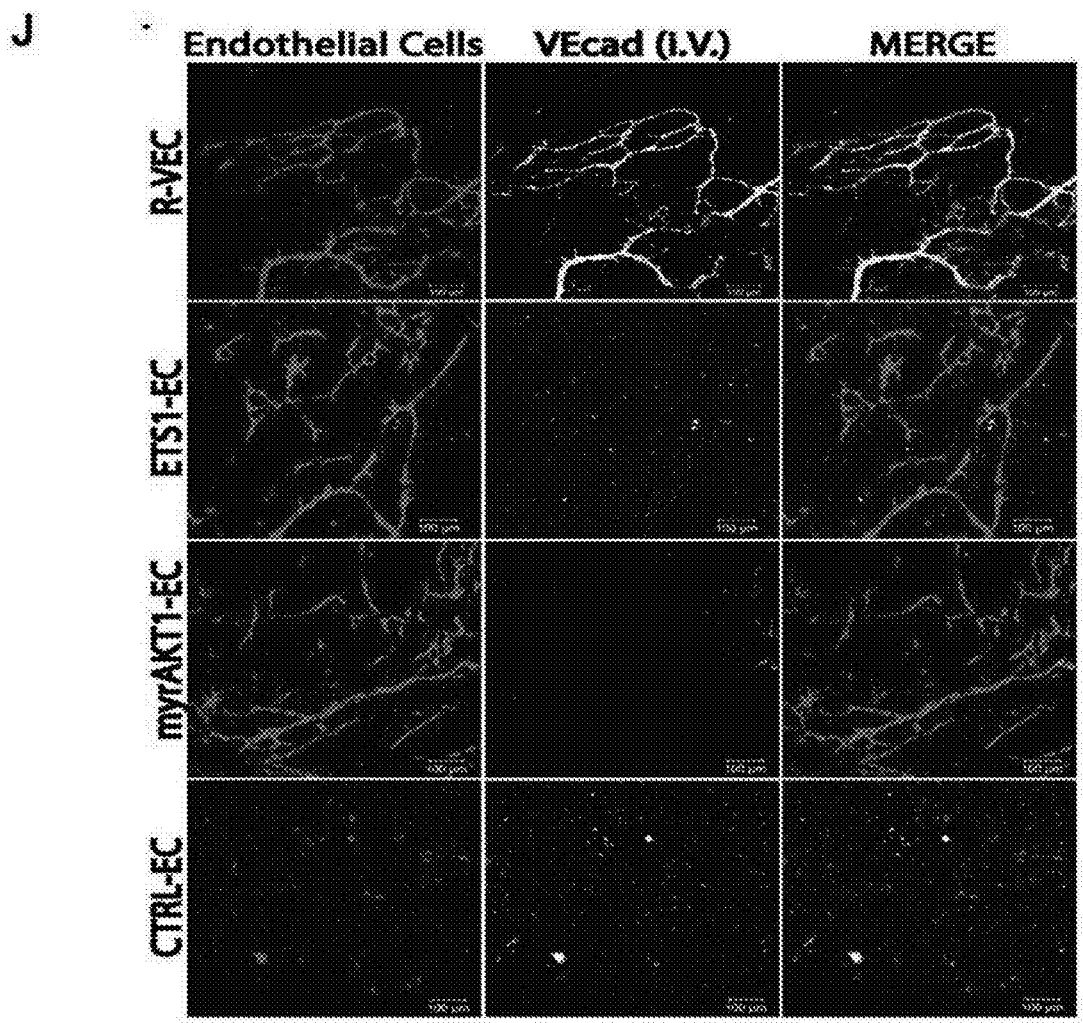
Figure 3K:
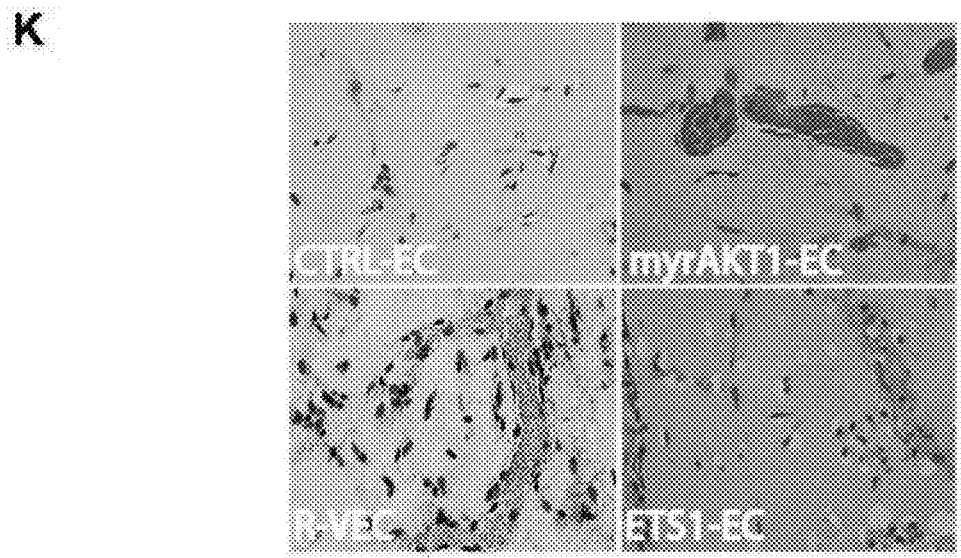
Figure 3L:
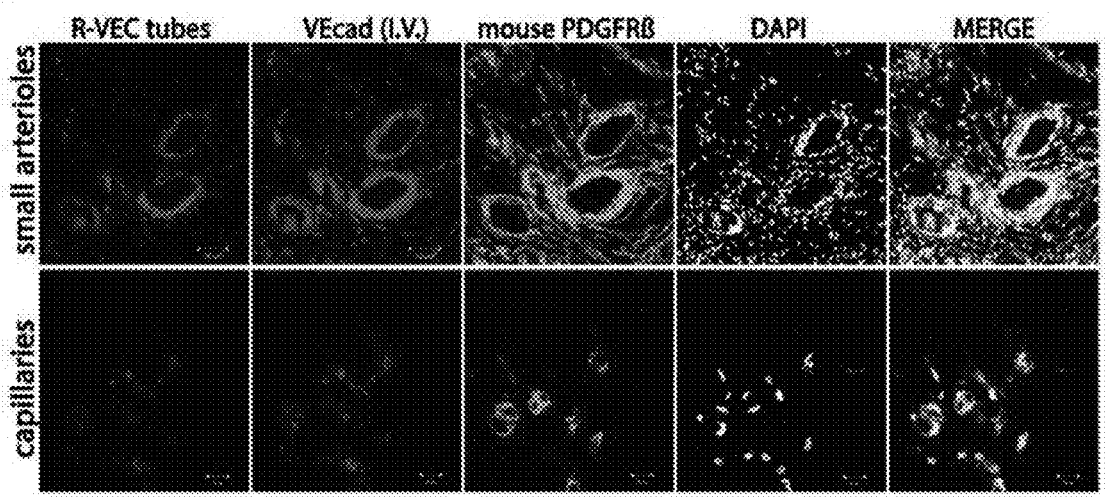
Figure 3M:
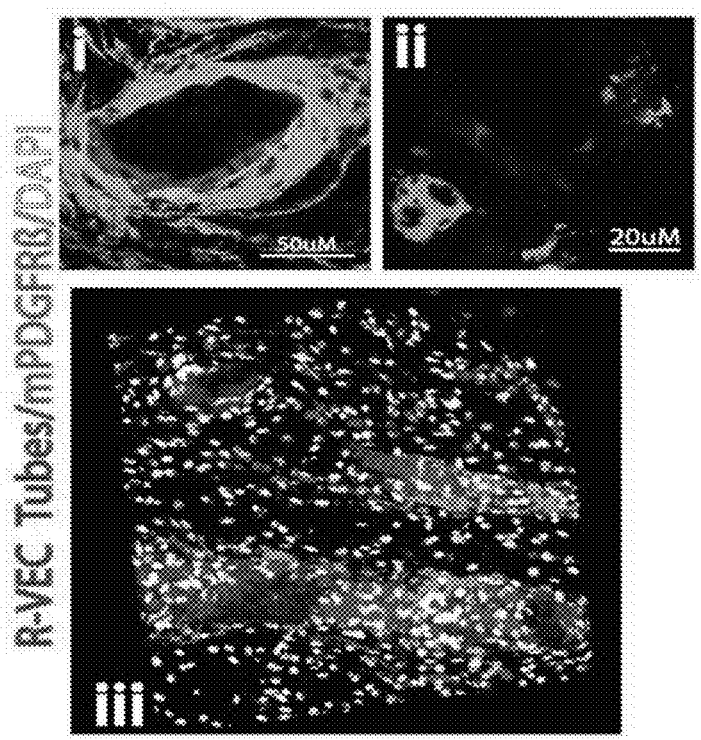

As shown in FIGS. 2A-2B and 3A-3M, the stable three-dimensional blood vessels produced by the present methods, can form functional blood vessels that perfuse fluid (FIG. 2A) and can form three-dimensional vascular networks including capillaries and arteriole structures when isolated and implanted in a subject (FIGS. 3L-3M). Further, as shown in FIG. 3M implanted stable three-dimensional blood vessels anastomosed to surrounding tissue by integrating endogenous pericytic cells to the lumenized vessel. In addition, and as shown in FIG. 1E, the stable three-dimensional blood vessels of the present disclosure remain stable and functional for over 4 months (16 weeks).

Therefore, in some embodiments, the stable three-dimensional blood vessels of the present disclosure are stable and functional for at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 13 weeks, at least 14 weeks, at least 16 weeks, at least 17 weeks, at least 18 weeks, at least 19 weeks, at least 20 weeks or more. In a specific embodiment, the three-dimensional blood vessels formed by the present methods are stable and functional for at least one month, or at least 2 months. In other embodiments, the three-dimensional blood vessels formed by the present methods are stable and functional for at least 3 months, at least 4 months, at least 5 months, at least 6 months or more. In one embodiment, the three-dimensional blood vessels formed by the present methods are stable and functional for 4 months.

Stable Three-Dimensional Blood Vessel Compositions and Therapeutic Methods of Use.

The culture method disclosed herein permits reproducible production of stable three-dimensional blood vessels, which are useful for several purposes such as vascularization of an organoid and therapeutic vascularization of injured tissue (tissue regeneration). The present disclosure also reveals that exogenous expression of ETV2 protein in differentiated endothelial cells leads to the autonomous self-assembly of stable, functional, three-dimensional blood vessels that have the capacity to form functional vascular networks in vitro and in vivo in the absence of pericytes, perfusion, and a scaffold.

As such, in a further aspect, the instant disclosure provides a composition containing a stable, three-dimensional blood vessel capable of autonomously forming a three-dimensional vascular network.

In certain embodiments, the stable three-dimensional blood vessel of the present disclosure includes a tubular structure (lumen), such as a vessel composed of at least one contiguous layer of reprogrammed endothelial cells. In other embodiments, the stable three-dimensional blood vessel includes a lumen composed of at least 2 layers of reprogrammed endothelial cells. In yet another embodiment, the stable three-dimensional blood vessel has a lumen composed of at least one layer of reprogrammed endothelial cells and at least one other layer of cells, e.g., differentiated vascular endothelial cells or non-vascular cells. In other embodiments, the stable three-dimensional blood vessel is composed of a combination of reprogrammed endothelial cells that express exogenous ETV2 transcription factor and endothelial cells that do not express exogenous ETV2.

In certain embodiments, the endothelial cells of the stable three-dimensional blood vessel express the exogenous ETV2 transcription factor encoding nucleic acid. In one embodiment, the expression of ETV2 transcription factor is transient, i.e., for a finite period of time, such as for a period of days, weeks or months). In specific embodiments, transient expression of the ETV2 transcription factor is modulated by an inducible expression system such as, for example, the reverse tet-transactivator (rtTA)-doxycycline inducible expression system. In other embodiments, the transient expression of the ETV2 transcription factor is modulated by the introduction of a modified synthetic RNA molecule encoding ETV2 protein. In other embodiments, the stable three-dimensional blood vessel of the present disclosure contains endothelial cells that constitutively (i.e., permanently) express exogenous ETV2 transcription factor. In other embodiments, the stable three-dimensional blood vessel is composed of a combination of endothelial cells that express exogenous ETV2 transcription factor and endothelial cells that do not express exogenous ETV2. In yet another embodiment, the stable three-dimensional blood vessel is composed of reprogrammed endothelial cells that do not express exogenous ETV2 transcription factor.

In some embodiments, the stable three-dimensional blood vessel of the present disclosure is an isolated blood vessel.

The term "isolated", when used in reference to a stable three-dimensional blood vessel or reprogrammed endothelial cell means that the vessel or cell has been removed from its naturally occurring environment or the environment from which it was formed and is substantially free of other molecules or culture medium. By "substantially free", it is meant that isolated three-dimensional blood vessels or isolated cell(s) account for at least 60%, 70%, 80%, 90%, or 95% (by dry weight or volume) of a composition or preparation. For example, an isolated stable three-dimensional blood vessel can be substantially free of culture medium, i.e., culture medium represents less than about 20% of the volume of the preparation, less than about 10% of the volume of the preparation or less than about 5% of the volume of the preparation. The level of purification can be based on the intended use. In certain non-limiting examples, the isolated stable three-dimensional blood vessel of the present disclosure can be removed from cell culture media used to form the stable three-dimensional blood vessel as well as any molecules added to the cell culture media, e.g., cytokines, growth factors, or amino acids. In another example, reprogrammed endothelial cells can be isolated by removing the cells from the cell culture media used to form the reprogrammed endothelial cells, as well as any cell culture additives, but at least a portion of a matrix remains with the isolated cells.

In some embodiments, an isolated stable three-dimensional blood vessel is removed, in-whole or in-part, from the environment from which it has been formed, e.g., cell culture, bioreactor, or subject. In certain embodiments, an isolated stable three-dimensional blood vessel is free of culture media, culture media components and additives, and any matrix on which it has been formed, e.g., Matrigel™ or L.E.C matrix. In other embodiments the isolated stable, three-dimensional blood vessel of the present disclosure has been removed from the culture media, culture media components and additives, but includes at least a portion of matrix, such as, for example, a Matrigel™ or L.E.C matrix. In one embodiment of the present disclosure, the stable three-dimensional blood vessel is functional. In specific embodiments, the functional stable three-dimensional blood vessel is capable of passing fluid (perfusing) through the lumenized blood vessel. In one embodiment, the functional stable three-dimensional blood vessel is capable of passing blood through the vessel. In yet another embodiment, the functional stable three-dimensional blood vessel is capable of forming a three-dimensional vascular network. In some embodiments, the three-dimensional vascular network includes an integrated patterned network of blood vessels on a tissue, such that blood and/or fluid can be supplied to the tissue ("vascularize") without the use of a scaffold, enforced perfusion or perivascular support. In specific embodiments, three-dimensional vascular network is autonomously formed by the stable three-dimensional blood vessel and at least one capillary, at least one arteriole, at least one venule, at least one lymphatic blood vessel or a combination thereof.

In some embodiments, the functional stable three-dimensional blood vessel of the present disclosure is functional for at least 1 month, at least 2 months, at least 3 months, at least 4 months, at least 5 months or more. In specific embodiments, the stable three-dimensional blood vessels of the present disclosure are stable and functional for 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks or more. In one embodiment, the three-dimensional blood vessel of the present disclosure is stable for at least 4 months (16 weeks), as shown in FIG. 1E.

Methods for Promoting Vascularization.

Since FIGS. 3L and 3M of the present disclosure show that stable three-dimensional blood vessels formed by culturing endothelial cells including exogenous ETV2 autonomously organize into patterned, long-lasting vascular networks capable of vascularizing endogenous tissue after implantation, the stable three-dimensional blood vessels of the present disclosure may also be used to facilitate vascularization of injured tissue in a subject.

Hence, in another aspect, a method for promoting vascularization in a subject is provided that includes administering to the subject a stable three-dimensional blood vessel. For example, the instant three-dimensional blood vessels can be used therapeutically for the repair of ischemic tissues, formation of blood vessels and heart valves, repair of damaged vessels, and inducing the formation of blood vessels in engineered tissues (e.g., prior to transplantation). In some embodiments, the subject has injured tissue, such as an organ in need of vascularizing.

This method involves administering to a human subject in need of such treatment, a composition containing a three-dimensional blood vessel of the present disclosure to promote vascularization in such tissue. Promoting vascularization (angiogenesis) in a tissue can be beneficial to subjects who have or are at risk to develop a condition including an ischemic condition, e.g., myocardial infarction, congestive heart failure, and peripheral vascular obstructive disease, stroke, reperfusion injury, limb ischemia; neuropathy (e.g., peripheral neuropathy, or diabetic neuropathy), organ failure (e.g., liver failure, kidney failure, and the like), diabetes, rheumatoid arthritis, and osteoporosis.

The tissue in need of vascularization can be a cardiac tissue, liver tissue, pancreatic tissue, renal tissue, muscle tissue, neural tissue, bone tissue, among others, which can be a tissue damaged and characterized by excess cell death, a tissue at risk for damage, or an artificially engineered tissue. In specific embodiments, the subject has injured heart tissue, injured liver tissue, injured lymphatic tissue, injured renal tissue, injured testicular tissue, injured ovarian tissue, an injured retina, injured pancreatic tissue, injured brain tissue, injured lung tissue, injured intestinal tissue, injured glandular tissue, injured muscle tissue or a combination thereof.

The present methods include administering the stable three-dimensional blood vessel to a subject in a manner that results in delivery of the blood vessel to or near the issue in need of repair or vascularization. In some instances, the stable three-dimensional blood vessel is locally administered, e.g., delivered directly (by injection, implantation or any suitable means) into the tissue or nearby tissue which is in need of vascularization. In one embodiment, the stable three-dimensional blood vessel is administered by surgical implantation to an injured tissue of the subject that is in need of vascularization. In specific embodiments, the stable three-dimensional blood vessel is implanted directly on an injured organ or tissue thereof. In other embodiments, the present methods include administering the stable three-dimensional blood vessel to a subject by injection such as, for example, injection directly to the injured tissue. In certain embodiments, a stable three-dimensional blood vessel is administered to the subject by intravenous injection, intraperitoneal injection, intramuscular injection, subcutaneous injection, or a combination thereof.

In one embodiment, stable three-dimensional blood vessel(s) are administered along with a matrix, such as in a suspension of extracellular matrix components. In specific embodiments, the stable three-dimensional vessel is administered on a matrix including a combination of laminin, entactin and collagen IV (L.E.C.). In one embodiment, a matrix can include laminin and entactin at a combined concentration of at least 5 mg/mL. In an exemplary embodiment, the blood vessel is administered along with a matrix including laminin and entactin at a combined concentration of 5 mg/mL. Since laminin and entactin can bind to each other and form a complex, a matrix can include a complex of laminin and entactin. For example, the matrix can include at least 5 mg/mL of a complex of laminin and entactin. For example, the blood vessel is administered along with a matrix containing a complex of laminin and entactin at a concentration of least 5 mg/mL, and at least 0.2 mg/mL collagen IV. In a specific embodiment, the matrix is composed of laminin and entactin at a combined concentration of 5.25 mg/mL and 0.2 mg/mL collagen IV. In other embodiments, the matrix is Matrigel™ (Corning).

In some embodiments, the method of promoting vascularization in a subject includes administering to the subject at least one stable three-dimensional blood vessel that has been formed in vitro. In other embodiments, the method includes administration of 2 or more stable three-dimensional blood vessels of the present disclosure that have been formed in vitro.

Regardless of the route of administration, once the stable three-dimensional blood vessel has been administered to the subject, the functional stable three-dimensional blood vessel establishes a three-dimensional vascular network, capable of vascularizing injured tissue. For example, the stable three-dimensional blood vessel can form a three-dimensional vascular network that includes at least one capillary, at least one arteriole, at least one venule, at least one lymphatic blood vessel or a combination thereof that is capable of transporting blood to an injured tissue.

The present disclosure also reveals that differentiated endothelial cells expressing an exogenous ETV2 transcription factor can autonomously form stable three-dimensional blood vessels when injected in a subject with certain extracellular matrix components.

Therefore, a further aspect of the present disclosure provides methods for promoting vascularization by administering a plurality of reprogrammed endothelial cells on a matrix to a tissue or organ. For example, the present methods include administration of a plurality of reprogrammed endothelial cells that include an exogenous ETV2 transcription factor encoding nucleic acid on a matrix set forth herein.

In some embodiments, the reprogrammed endothelial cells and matrix can be administered directly to a subject in need of vascularization. Here, the reprogrammed endothelial cells and matrix can be delivered directly to an injured tissue by intraperitoneal injection, intramuscular injection, subcutaneous injection, surgical implantation or a combination thereof.

Methods for Vascularizing an Organoid or Decellularized Organ.

In another aspect of the present disclosure a method for vascularizing an organoid is provided. Here, the method includes culturing an organoid with an endothelial cell including an exogenous nucleic acid encoding ETV2 transcription factor on a matrix under conditions that express exogenous ETV2 protein in the endothelial cell to form a stable, three-dimensional vascular network on the organoid.

In some embodiments, the method for vascularizing an organoid includes culturing the organoid with reprogrammed endothelial cells on a matrix. A matrix for use in the present methods can include laminin and entactin at a combined concentration of at least 5 mg/mL. As laminin and entactin can bind to each other and form a complex, a matrix for use in the present methods can include a complex of laminin and entactin. For example, the matrix can include at least 5 mg/mL of a complex of laminin and entactin. In an exemplary embodiment, reprogrammed endothelial cells are cultured on a matrix including laminin and entactin at a combined concentration of 5 mg/mL. In specific embodiments, the matrix used in the present methods is composed of a combination of laminin, entactin and collagen IV (L.E.C.). For example, the endothelial cells and organoid can be cultured on a matrix containing at least 5 mg/mL of laminin and entactin, and at least 0.2 mg/mL collagen IV to form long-lasting, functional three-dimensional artificial blood vessels on the organoid. In a specific embodiment, the matrix is composed of laminin and entactin at a combined concentration of 5.25 mg/mL and 0.2 mg/mL collagen IV. In other embodiments, the matrix is Matrigel™ (Corning).

The endothelial cells and organoids can be cultured in any culture medium capable of sustaining growth and development of endothelial cells such as, but not limited to, DMEM (high or low glucose), advanced DMEM, DMEM/MCDB 201, Eagle's basal medium, Ham's F10 medium (F10), Ham's F-12 medium (F12), Hayflick's Medium, Iscove's modified Dulbecco's medium, Mesenchymal Stem Cell Growth Medium (MSCGM), DMEM/F12, RPMI 1640, and CELL-GRO-FREE (Corning cellgro, Corning, NY). The culture medium can be supplemented with one or more components including, for example fetal bovine serum, preferably about 2-15% (v/v); equine serum; human serum; fetal calf serum; beta-mercaptoethanol, preferably about 0.001% (v/v); one or more growth factors, for example, platelet-derived growth factor (PDGF), epidermal growth factor (EGF), fibroblast growth factor (FGF), vascular endothelial growth factor (VEGF), insulin-like growth factor-1 (IGF-1), leukocyte inhibitory factor (LIF) and erythropoietin; amino acids, including L-valine; and one or more antibiotic and/or antimycotic agents to control microbial contamination, such as, for example, penicillin G, streptomycin sulfate, amphotericin B, gentamicin, and nystatin, either alone or in combination.

In one embodiment, the method for vascularizing an organoid includes culturing the organoid with endothelial cells on a matrix in culture media that includes fibroblast growth factor (FGF). In a specific embodiment, the culture media includes basic fibroblast growth factor (FGF2). In some embodiments, the culture media includes heparin. In a specific embodiment, the method for vascularizing an organoid includes culturing the organoid with endothelial cells on a matrix in a culture media including FGF2 and heparin.

The organoids and endothelial cell(s) including an exogenous nucleic acid encoding ETV2 transcription factor can be cultured on a matrix under conditions that express exogenous ETV2 protein in the endothelial cell for any period of time necessary to induce the formation of a functional, lumenized three-dimensional vascular network on the organoid, i.e., vascularize the organoid. During culturing of the organoid with reprogrammed endothelial cells a functional vascular network will form that includes at least one capillary, at least one arteriole, at least one venule, at least one lymphatic blood vessel, or a combination thereof that is capable of transporting blood throughout the organoid. For example, in certain embodiments, the organoid and endothelial cell(s) are cultured for at least a week (7 days), at least 10 days, at least 2 weeks, at least 3 weeks, at least 4 weeks, at least 5 weeks, at least 6 weeks, at least 7 weeks, at least 8 weeks or more to induce the endothelial cells to organize into patterned, long-lasting blood vessels on the organoid.

The present methods for vascularizing an organoid can be applied to any type of organoid. For example, an organoid for use in the present methods can be a small intestine organoid, colon organoid, kidney organoid, heart organoid or a tumor organoid. In some embodiments, the methods can be used to vascularize a tumor organoid, whereby the tumor organoid can be tissue specific such as a breast cancer organoid, a colon cancer organoid, a renal cancer organoid, or an intestinal cancer organoid.

The vascularized organoids of the present disclosure can be used by one of ordinary skill in the art for any number of purposes. As such, in some embodiments, the present methods for vascularizing an organoid include isolating the vascularized organoid.

Once the vascularized organoid is obtained, the vascularized organoid can be administered to a subject, such as a human or an animal (e.g., mouse, rat, dog, monkey). In specific embodiments, the vascularized organoid can be administered to a human subject by surgical implantation.

In other embodiments, the isolated vascularized organoid can be used to determine the efficacy of a therapeutic agent. Here, the vascularized organoid is contacted with a therapeutic agent and cultured for a period of time in the presence of the therapeutic agent. The organoid function, cellular growth and health can then be analyzed to determine the efficacy of the therapeutic agent.

Examples of therapeutic agents that can utilized in the present methods include, but are not limited to, anti-inflammatory drugs, anti-angiogenic molecules, antibodies, cytotoxic drugs, other toxins, radionuclides, immune cell regulators, small molecule, exosomes and gene expression products. For example, a chemotherapeutic agent may be administered to the vascularized organoid (i.e., tumor organoid) to determine the anti-tumor activity (efficacy) of the chemotherapeutic agent.

The present disclosure also reveals that culturing a decellularized organ with endothelial cells including an exogenous nucleic acid encoding ETV2 transcription factor under conditions that express exogenous ETV2 protein in the cells results in the development of functional vascular structures on the decellularized organ.

As such, another aspect of the present disclosure provides a method for revascularizing a decellularized organ. The method for revascularizing a decellularized organ includes culturing the devascularized organ with endothelial cells on a matrix for a period of time sufficient to form a functional three-dimensional vascular network on the decellularized organ. During culturing of the decellularized organ with reprogrammed endothelial cells a functional vascular network will form that includes at least one capillary, at least one arteriole, at least one venule, at least one lymphatic blood vessel, or a combination thereof that is capable of transporting blood throughout the organoid. For example, in certain embodiments, the decellularized organ and endothelial cell(s) are cultured for at least a week (7 days), at least 10 days, at least 2 weeks, at least 3 weeks, at least 4 weeks, at least 5 weeks, at least 6 weeks, at least 7 weeks, at least 8 weeks or more to induce the endothelial cells to organize into patterned, long-lasting blood vessels on the decellularized organ and subsequently form a functional vascular network that revascularizes the decellularized organ.

In some embodiments, the method for revascularizing a decellularized organ includes culturing the decellularized organ with endothelial cells on a matrix under conditions that express exogenous ETV2 protein in a bioreactor. A matrix for use in the present methods can include laminin and entactin at a combined concentration of at least 5 mg/mL. For example, the matrix can include at least 5 mg/mL of a complex of laminin and entactin. In an exemplary embodiment, the matrix includes laminin and entactin at a combined concentration of 5 mg/mL. In specific embodiments, the matrix used in the present methods is composed of a combination of laminin, entactin and collagen IV (L.E.C.). For example, the methods include culturing on a matrix containing at least 5 mg/mL of laminin and entactin, and at least 0.2 mg/mL collagen IV to form long-lasting, functional three-dimensional artificial blood vessels. In a specific embodiment, the matrix contains laminin and entactin at a combined concentration of 5.25 mg/mL and 0.2 mg/mL collagen IV. In other embodiments, the matrix is Matrigel™ (Corning).

The present methods can be applied to any type of decellularized organ. For example, an endothelial cell can be cultured under conditions that express exogenous ETV2 protein on a decellularized organ, such a decellularized heart, kidney, testis, ovary, retina, bone, endocrine gland, thyroid gland, trachea, lymph node, liver, pancreas, brain, lung, spleen, large intestine or small intestine.

The revascularized organs of the present disclosure can be used by one of ordinary skill in the art for any number of purposes. As such, in some embodiments, the present methods for revascularizing decellularized organ include isolating the revascularized organ.

In an exemplary embodiment, the revascularized organ can be obtained and then administered to a subject, such as a human or an animal (e.g., mouse, rat, dog, monkey). In specific embodiments, the revascularized organoid is isolated and be administered to a subject by surgical implantation.

In other embodiments, the isolated revascularized organ can be used to determine the efficacy of a therapeutic agent. Here, the revascularized organ is contacted with a therapeutic agent and cultured for a period of time in the presence of the therapeutic agent. Then revascularized organ function, cellular growth and organ health can then be analyzed to determine the efficacy of the therapeutic agent.

EXAMPLES

The present description is further illustrated by the following examples, which should not be construed as limiting in any way. The contents of all cited references (including literature references, issued patents, and published patent applications as cited throughout this application) are hereby expressly incorporated by reference.

Example 1: Materials and Methods

Cell culture. Human umbilical vein endothelial cells (HUVEC) and human adipose tissue endothelial cells were isolated in lab using a collagenase-based digestion approach as set forth in Ginsberg, M. et al. *Cell* (2012) 151, 559-575, the entire contents of which is incorporated herein by reference. The isolated endothelial cells were then grown in tissue culture dishes coated with 0.2% gelatin grown in complete media (400 ml of M199, 100 ml heat inactivated FBS, 7.5 ml Hepes, 5 ml antibiotics, 5 ml glutamax, 5 ml of lipid mixture, and ½ bottle of endothelial cell growth supplement (Alpha Aesar). The cells were transduced with lenti pgk-ETV2 or an empty lentivector after passage. As necessary, the cells were also labeled by using pgk-mCherry or pgk-GFP lentivirus. The cells were split 1:2 using accutase and passaged on gelatinized plates. As necessary, cells were frozen down to be used in future experiments. Overall, more than 10 batches of different HUVECs were used for the experiments. Endothelial cells used for tube formation assays were of passage 5-10.

Human adipose derived endothelial cells were isolated by mechanical fragmentation followed by collagenase digestion for 30 minutes. After plating the crude population of cells on the plastic dish and expansion for 5 to 7 days the cells were then sorted to purify VE-cadherin$^+$ CD31$^+$ endothelial cells and expanded as described above.

Tube Formation Assays.

24 well plates were coated with 250-3000 of Matrigel™ (Corning) for 30 min in an incubator. Meanwhile, cells with or without ETV2 were accutased and counted. Cells were then resuspended in StemSpan (Stem Cell Technologies) supplemented with knock out serum and cytokines (10 ng/mlFGF-2, 10 ng/ml IGF1, 20 ng/ml EGF, 20 ng/ml SCF, 10 ng/ml IL6) (Peprotech). 100,000 cells either with or without ETV2 were then dispersed in each well. Plates were incubated at 5% oxygen for the remainder of the experiments. For Laminin/Entactin/CollagenIV (L.E.C)-based experiments a high concentration (i.e., 15 mg/ml) of laminin and entactin (Corning) was mixed with different amounts of CollagenIV (Corning) in phosphate buffer solution (PBS). The most effective concentration of L.E.C. for lumen formation included 200 µl of (15 mg/ml) laminin/entactin complex and 100 µl of collagen IV for a final matrix composed of 5.25 mg/mL laminin/entactin complex with 2.0 mg/mL of Collagen IV. Vessel density was measured over a course of 24 hours to 16 weeks. EVOS® inverted microscope was used to capture images in four different randomized zones in each well for each condition and time point with 4× magnification. All the images were then analyzed for vessel density using tracing through ImageJ. The same procedure was used for cells transduced with ETS1 or myrAKT1.

Staining of Tubes In Vitro.

At 8 to 12 weeks all media was removed from the wells. The tubes were washed once with phosphate buffered saline (PBS), and then fixed for 30 minutes at room temperature, washed again with PBS and put in blocking buffer for 1 hour and room temperature. The tubes were then stained with VECAD (R&D), Laminin (abcam), Collagen IV (abcam) and/or podocylaxin (R&D). The next day, the tubes were washed again in PBS, incubated for 3 hours in secondary antibodies, and counterstained with DAPI. All images were obtained through Zeiss 710 confocal microscopy.

Electron Microscopy.

Tissues were washed with serum-free media or phosphate-buffered saline (PBS) then fixed with a modified Karmovsky's fix of 2.5% glutaraldehyde, 4% parafomaldehyde and 0.02% picric acid in 0.1M sodium cacodylate buffer at pH 7.2. Following a secondary fixation in 1% osmium tetroxide, 1.5% potassium ferricyanide samples were dehydrated through a graded ethanol series, and embedded in an Epon analog resin. Ultrathin sections were cut using a Diatome diamond knife (Diatome, USA, Hatfield, PA) on a Leica Ultracut S ultramicrotome (Leica, Vienna, Austria). Sections were collected on copper grids and further contrasted with lead and viewed on a JEM 1400 electron microscope (JEOL, USA, Inc., Peabody, MA) operated at 100 kV. Images were recorded with a Veleta 2K×2K digital camera (Olympus-SIS, Germany).

Bead Flow for Assessing Perfusion Capacity of Three-Dimensional Blood Vessels.

Each device was formed of two layers of polydimethylsiloxane (PDMS; Sylgard 184; Dow-Corning), which were cast from silicon wafer masters. The devices were plasma-treated with plasma etcher (PlasmaEtch) and subsequently treated with trimethoxysilane (Sigma) overnight. Prior to usage, the devices were washed with MiliQ $H_2O$ overnight. A mixture of 3 million reprogrammed endothelial cells (R-VEC) or control non-transduced endothelial cells (CTRL-EC) in 2.5 mg/ml bovine fibrinogen (Sigma) and 3 U/ml bovine thrombin (Sigma) was injected into the devices with two 400 µm acupuncture needles (Hwato). After the cell and gel mixture polymerized, the needles were pulled out forming two hollow channels. ETV2 transduced (reprogrammed endothelial cells) and non-transduced (control) endothelial cells were separately seeded into the hollow channels to form two parent vessels on the next day. Cells were cultured in endothelial cell growth medium 2 (Promocell) and refreshed daily until day 6. On day 6, the devices were connected to a syringe pump (Harvard Apparatus) and 4 µm red fluorescent microspheres (Invitrogen) were injected into one of the parent vessels in each device at 50 µL/min. Timelapse of fluorescent beads flowing in the devices was captured at 50 ms interval with Nikon Eclipse TiE (Nikon) equipped with an Andor Zyla sCMOS 5.5 MP camera (Andor). Timelapse images of fluorescent beads were stacked together and overlaid with HUVECs vessels using ImageJ software.

In Vivo Assessment of Exemplary Blood Vessels.

Human umbilical vein derived endothelial cells (HU-VECs) and human adipose derived human endothelial cells that were transduced with a lentiviral empty vector or lenti-ETV2 vector, and labeled with GFP or mCherry fluorescent markers (2 million cells/plug) were injected subcutaneously in male or female 8-12 week old SCID-beige mice (Taconic). The cells were first resuspended in PBS (50 µl) and then mixed with Matrigel™ or L.E.C. matrix s as described above (350 µl). The cellular/matrix suspensions also included FGF-2 (10 ng/ml), VEGF-A (20 ng/ml), and heparin (100 ng/ml). Each mouse received two plugs one for control cells and one for cells expressing with ETV2. At 1 week, 1 month, 2 months or 5 months the mice were injected with VECAD (clone BV9-Biolegend) conjugated to Alexa-647 (25 µg in 100 µlof PBS) that detect only human endothelial cells, to assess the perfusion and anastomosis potential of the ETV2-expressing (reprogrammed, R-VEC) and non-ETV2-expressing (control) human endothelial cells. Whole mount images were taken directly on a Zeiss 710 confocal microscope using a well containing a coverslip bottom. The plugs were fixed in 4% PFA overnight and then dehydrated in ethanol or put in sucrose for further immunostaining. The dehydrated plugs were sectioned and stained with H&E. The sections were processed for immunostaining as described below. The same procedure was followed when ETS1—and/or myrAKT1-expressing cells were implanted for 1 month.

Immunostaining of Tissue Sections.

Frozen sections (20 µM), previously fixed in 4% PFA and treated in sucrose, were washed once with PBS. Then the slides were incubated in blocking buffer for 30 minutes at room temperature and overnight in primary antibody (1:500) at 4° C. The next day, the slides were washed 3 times for 10 minutes at room temperature and then incubated for three hours in fluorescent conjugated secondary antibody. Finally, the slides were washed 3 times for 10 minutes and counter stained with DAPI. The sections were mounted with coverslips and further used to take images using confocal microscopy. For stroma staining, a PDGFRβ antibody (1:500, Biolegend) detecting mouse peri-vascular cells was used. Several images were taken from sections from different parts of each plug. At least 12 images from different slides were obtained for each condition and time point. Images were processed using ImageJ and the percentage of vessel area over the area of each image field was quantified by using the threshold feature in ImageJ software.

Transplantation of Pre-Formed Stable Three-Dimensional Artificial Blood Vessels.

8-12 week old artificial blood vessels formed as described above on either Matrigel™ or L.E.C. matrix, were isolated by removing the culture media and overlaid with 200 µl of Matrigel™ or L.E.C. Within 30 minutes, the gelled plugs were subcutaneously administered to SCID-Beige mice. The whole plugs were surgically inserted into a pocket formed through a subcutaneous incision and sutured closed. After two weeks, the mice were injected with intravital antibody to human VECAD in order to detect the formation of anastomosed perfused blood vessels.

Intestinal tissue harvesting and organ decellularization. Intestines were harvested from Sprague Dawley rats ranging from 250 g to 350 g in weight. Briefly, under aseptic conditions a midline laparotomy was performed and the intestine exposed. A 5 cm long segment of intestine was isolated, preserving the mesenteric artery and the mesenteric vein that perfuse the isolated segment. Both vessels were cannulated with a 26 G cannula, intestinal lumen was cannulated using one-quarter inch barbed connectors. The isolated intestinal segments were decellularized by perfusing the vasculature and lumen at 1 ml/min using a peristaltic pump (iPump). The decellularization process consisted of perfusing milliQ water for 24 hours, sodium deoxycholate (Sigma) for 4 hours and Dnase I (Sigma) for 3 hours. Decellularized intestines were sterilized with gamma radiation before use.

Bioreactor Culture.

Decellularized intestines were seeded either with 5 million GFP$^+$ETV2$^+$ human endothelial cells (reprogrammed ECs expressing exogenous ETV2) or with 5 million GFP$^+$ control-endothelial cells (CTRL-ECs). Cells were seeded through the mesenteric artery and mesenteric vein. Seeded intestines were mounted inside bioreactor under sterile conditions. After 24 hours, perfusion was started through the mesenteric artery at 1 ml/min using a peristaltic pump (iPump). Cells were grown in M199/EBSS (HyClone) supplemented with 20% heat inactivated FBS, 1% Pen-Strep, 1.5% HEPES (Corning), 1% Glutamax™ (Gibco), 1% 1 pid mixture (Gibco), 1% heparin (Sigma) and 15 µg/ml endothelial cell growth supplement (Merck) for the first 5 days, then cells were grown for 2 days in StemSpan (Stemcell Technologies) supplemented with 1.1% knock-out serum (Thermo), 1% Pen-Strep, 1% Glutamax, 10 ng/ml FGF (Peprotech), 20 ng/ml EGF (Invitrogen), 10 ng/ml IGF2 (Peprotech), 20 ng/ml SCF (Peprotech) and 10 ng/ml IL6 (Peprotech). After 7 days, re-endothelialized intestines were harvested under sterile conditions and segments 5×7 mm were excised for implantation. Remaining intestinal tissue was then fixed in 4% paraformaldehyde, mounted and prepared for imaging by fluorescent microscopy. To assess patency of the vessels, some re-endothelialized intestines were intravitaly perfused with fluorescently-labeled LDL or antibodies to human PECAM (CD31).

Heterotopic Graft Implantation.

Immunocompromised NOD-SCID-gamma (NSG) mice, aged between 8 and 12 weeks, were anaesthetized with a 2-5% isoflurane-oxygen gas mix. Buprenorphine 0.1 mg/Kg was administered at the induction for analgesia. Under aseptic conditions a midline laparotomy was performed. The stomach was externalized from the incision and the omentum stretched from the great curvature. A segment of the engineered intestine was then enveloped in the omentum, using 8/0 suture to secure the closure of the omental wrap. The stomach and the omentum were placed back in the abdomen and the laparotomy closed using 6/0 suture. Animals were allowed to normally eat and drink immediately after surgery and no further medications were administered during the post-operative periods. After 1 week or 4 weeks mice were intravenously injected with fluorescently-labeled anti-VECAD or fluorescently-labeled isolectin and euthanized. Grafts were retrieved together with the omental envelope and fixed in 4% paraformaldehyde, mounted and prepared for imaging by fluorescent microscopy.

Analysis of Functional Vascular Perfusion, Anastomosis, Size, Shape and Density.

Quantification of in vitro endothelial revascularization was performed on an area of 5×5 10× fields of view. Images were processed using ImageJ software by setting a threshold and quantifying the area covered by CD31 signal with respect to the intestine area. In vivo quantification of cells positive for GFP and VE-Cadherin was performed on images acquired with a confocal microscope (Zeiss LSM710) evaluating an area of 3×3 20× fields of view. Evaluation of vascular parameter was performed using Angiotool software (National Cancer Institute).

Organoid Isolation and Culture.

Mouse small intestinal organoids were isolated and maintained as previously described in O'Rourke, K. P., et al. Bio Protoc. (2016) 6, the entire contents of which is hereby incorporated by reference. Isolation of human colonic crypts and adenomas; culture and maintenance of organoid cultures were preformed as previously described in Sugimoto, S. & Sato, T. Methods Mol Biol (2017) 1612, 97-105, the entire contents of which is hereby incorporated herein by reference. Normal and adenoma tissues were collected. Briefly, cultures were grown in serum free medium containing Wnt3a, R-spondin-3 and Noggin with 10 mM nicotinamide (Sigma-Aldrich) and propagated in Matrigel™ (Corning). Organoids were passaged every 7 days by digesting in TrypLE Select (Thermofisher) supplemented with 10 µM Y27632 (Tocris Bioscience).

Organoid Co-Cultures with Reprogrammed Human Endothelial Cells.

MCherry ETV2 or control (CTRL) ECs (at a final concentration of 4 million cells/ml) were mixed with mouse small intestine organoids, normal human colon or patient derived tumor organoids in a 750 Matrigel™ bubble in 24 wells plates or 40 µl Matrigel™ bubble in chamber slides (normal organoids were passaged 1:2 and tumor organoids passaged at 1:3) and cultured in organoid media with the addition of FGF-2 (10 ng/ml) and heparin (100 ng/ml). Images were taken from live cultures at 24 hrs, days 4, 5 and 7. At day 8 the co-cultures were fixed and whole mount stained with keratin 20 (KRT20), EdU and/or EpCam.

RNA Library Preparation and Sequence Data Processing. At least 100 ng of total RNA was isolated (phenol-chloroform separation of TRIzol LS) for each sample and purified using Qiagen's RNeasy Mini Kit. RNA quality was verified using an Agilent Technologies 2100 Bioanalyzer. RNA library preps were prepared and multiplexed using Illumina TruSeq RNA Library Preparation Kit v2 (non-stranded and poly-A selection) and 10 nM of cDNA was used as input for high-throughput sequencing via Illumina's HiSeq 2500 producing 51 base paired-end reads. Sequencing reads were de-multiplexed (bcl2fastq) and high quality reads were mapped (TopHat2; Bowtie2) to the transcriptome sequence reference of the UCSC hg19 genome built for HUVEC samples and UCSC mm10 genome build for mouse ECs. For gene abundance measures (FPKM values), mapped reads were assembled into transcripts and quantified (Cufflinks). Genes with FPKM <1 were filtered out and base-2 log-transformed FPKM values were used for plotting MDS, volcano, and heatmap plots. Gene ontology analysis was performed using DAVID Bioinformatics Resource Tools. P-values displayed within Venn diagrams were calculated based on the cumulative distribution function (CDF) of the hypergeometric distribution curve.

ChIP and Antibodies.

ChIP assays were performed with approximately $1\times10^7$ cells per experiment. Briefly, cells were crosslinked in 1% paraformaldehyde (PFA) for 10 minutes at 37° C., then quenched by 0.125M glycine. Chromatin was sheared using a Bioruptor (Diagenode) to create fragments of 200-400 base pairs, incubated with 2-5 µg of antibody bound to 75 µl Dynabeads M-280 (Invitrogen) and incubated overnight at 4° C. Magnetic beads were washed and chromatin was eluted. The ChIP DNA was reverse-crosslinked and column-purified. ChIP was performed using the following antibodies: Flag (Sigma F1804); H3K4me3 (Abcam ab8580); and H3K27ac (Abcam ab4729). RNA was isolated using QIAGEN RNeasy kit. RNA-seq libraries were prepared with the Illumina TruSeq RNA Sample Preparation Kit. ChIP-seq libraries were prepared with the Illumina TruSeq DNA Sample Preparation Kit. Both RNA-seq and ChIP-seq libraries were sequenced with Illumina HiSeq 4000 system.

ChIP-seq reads were aligned to the reference human genome (hg19, Genome Reference Consortium GRCh37) using the BWA alignment software (version 0.5.9). Unique reads that mapped to a single best-matching location with no more than 4% of the read length of mismatches were kept for peak identification and profile generation. Sequence data were visualized with IGV by normalizing to 1 million reads. The software MACS2 was applied to the ChIP-seq data with sequencing data from input DNA as control to identify genomic enrichment (peak) of ETV2 or specific histone modifications. The resulting peaks were filtered by p-value<0.05 for ETV2 and p-value<0.01 for K4me3 or K27ac modification. Read counts were computed in individual promoters by HOMER. Each identified peak was annotated to promoters (±2 kb from transcription start site), gene body, or intergenic region by HOMER.

Example 2. Transient Expression of Exogenous ETV2 in Endothelial Cells Forms Long-Lasting and Stable Three-Dimensional Artificial Blood Vessels In Vitro The present studies show that transient induction of ETV2 in differentiated endothelial cells will reprogram endothelial cells to acquire enhanced cellular affinity for non-vascular cells as well as develop durability and patterning plasticity to form stable, three dimensional artificial vessels in vitro and in vivo. To determine whether ETV2 transcription factor expression altered vessel formation, endothelial cells transduced with ETV2 were single cell FACS sorted and clonally grown out. Exogenous ETV2 expression in endothelial cells consistently resulted in the formation of branched sprouting vascular networks with organized durable geometric patterns of artificial blood vessels that often localized to the surface of the extracellular matrix.

Dosing of ETV2 by a lentivirus vector was assessed in both flat endothelial cells forming typical planar monolayer cobblestones and three dimensional (3D) tubes by immunostaining and western blot analyses. See FIGS. 1A-1C. Over 7 days of culture, under serum free condition in 5% oxygen tension (normoxia), human umbilical vein endothelial cells or adult adipose derived endothelial cells, expressing exogenous ETV2 (R-VECs) were significantly better at forming functional 3D artificial vessels, exhibiting a greater than 50-fold increase in vessel formation compared to control endothelial cells that do not include exogenous ETV2 as shown in FIGS. 1D-1F. Remarkably, the three dimensional artificial vessels formed were able to be maintained in vitro for over 16 weeks, as shown in FIG. 1E.

To determine whether ability of differentiated endothelial cells to self-assemble into lumenized, stable 3D artificial blood vessels is an attribute of other ETS-family of transcription factors tubes, differentiated endothelial cells were transduced with another ETS transcription factor, ETS1. Further, to examine whether ETV2 confers angiogenic function to endothelial cells by increasing the cell survival, endothelial cells were transduced with constitutively active myristoylated-AKT1 (myrAKT1). As shown, in FIG. 1G, neither ETS1, nor myrAKT1 expression enabled differentiated endothelial cells to form stable 3D artificial blood vessels as ETV2 did. Thus, it has been shown that exogenous ETV2 expression in differentiated human endothelial cells reprograms the cells and provide the ECs with capacity to self-assemble into stable 3D blood vessels without the constraints of artificial scaffolds, pericyte coverage, enforced perfusion or shear stress required by existing methods for forming artificial blood vessels.

Figures 1G, 1H, 1I, 1J:
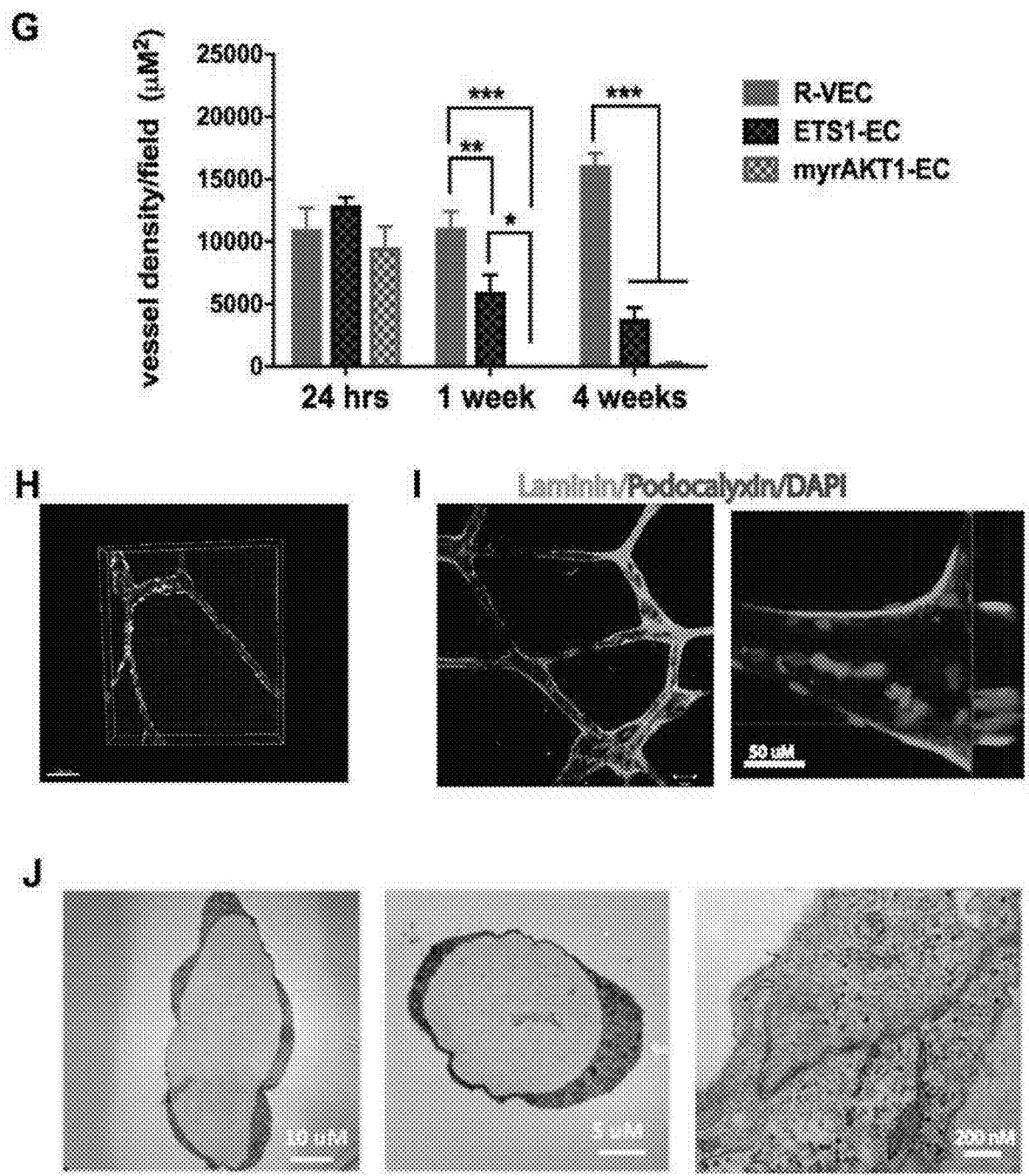

Proper lumen formation is required for artificial 3D blood vessel function. As shown in FIG. 1H, confocal microscopy reveals the presence of continuous uninterrupted lumen in the stable 3D artificial blood vessels of the present disclosure. The vessels manifested proper polarization with podocalyxin expressed on the apical side and laminin on the basal side (FIG. 1I). Further, as shown in FIG. 1J, at weeks 8-12 post vessel formation, artificial 3D blood vessels autonomously form branching patterned vessels with patent lumens and tight junctions. Therefore, the stable three-dimensional blood vessels of the present disclosure are lumenized and display proper apical-basal polarity.

Figure 1K:
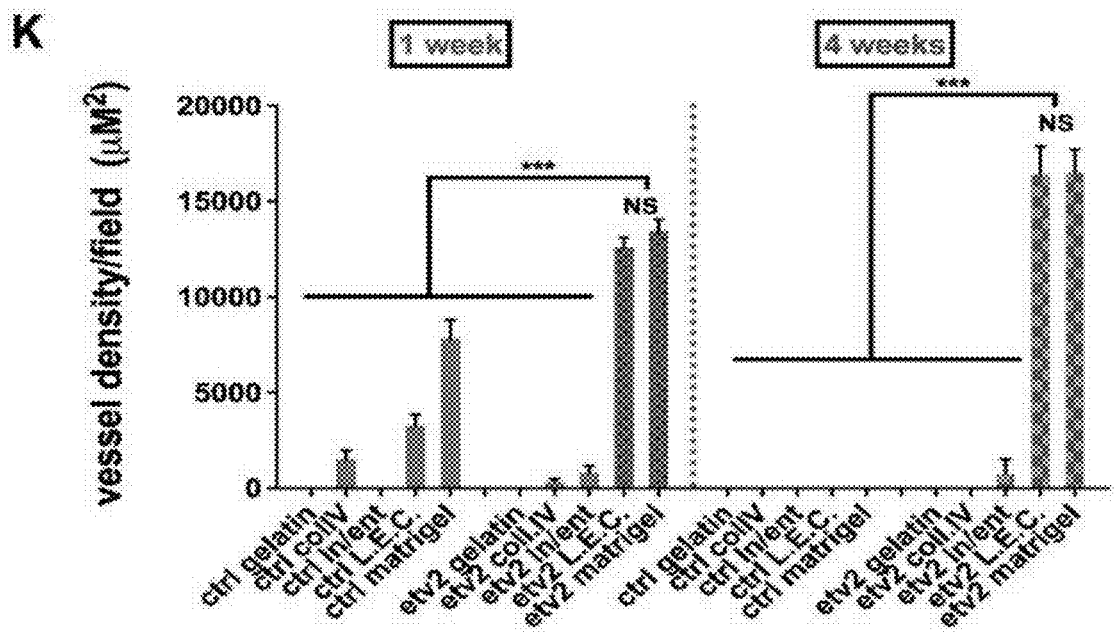
Figure 1L:
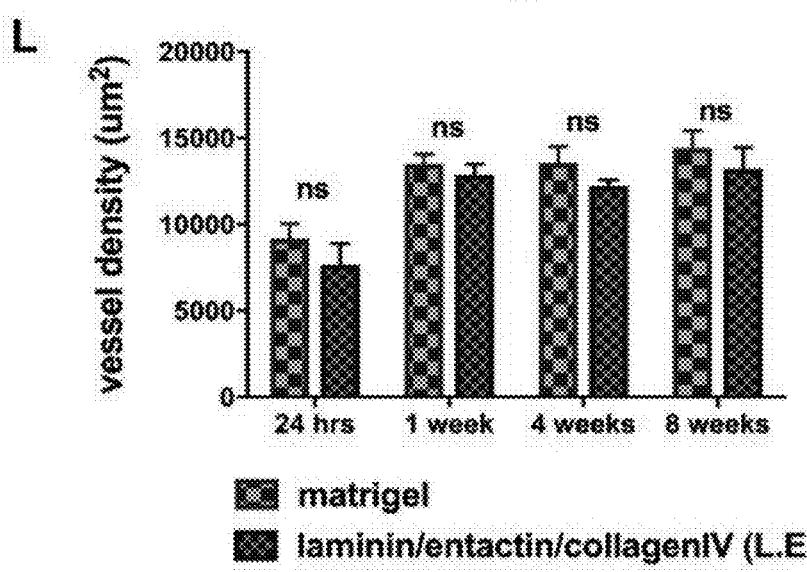
Figure 1M:
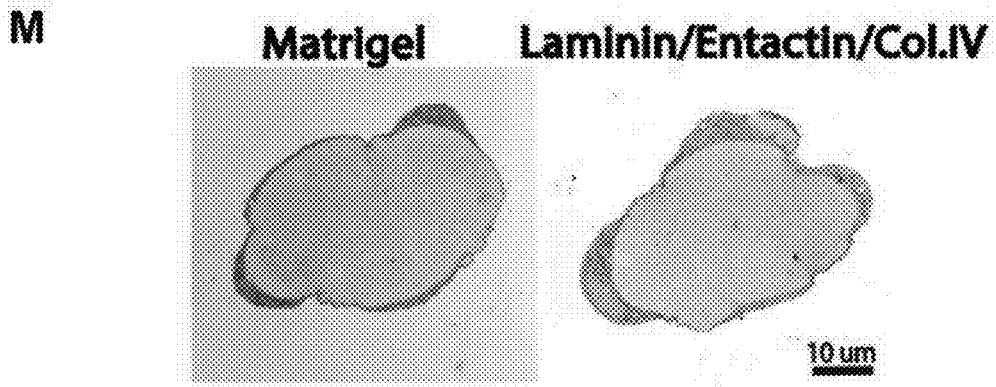

Current approaches for in vitro vascular patterning and organoid formation require the use of a crude preparation of extracellular matrix, such as Matrigel™ Matrigel™ contains numerous digested matrix components, and thus is difficult to determine whether particular components are required for vessel formation or their interaction with organoid cellular components. Screening through numerous combinations of vascular extracellular matrix, it has been determined herein that a precise stoichiometry of matrix components laminin, entactin and collagen IV (L.E.C) allows for the self-assembly of the stable 3D blood vessels of the present disclosure. Notably, as shown in FIG. 1K, control naïve human endothelial cells did not form vessel networks, when using L.E.C. as a matrix. Further, as shown in FIG. 1L vessels formed on L.E.C and Matrigel™ exhibited similar vessel density and branching beyond 8 weeks. Electron microscopy confirmed the presence of a lumen in vessels formed on L.E.C. See FIG. 1M. Taken together, the exogenous expression of ETV2 in differentiated endothelial cells forms stable, three-dimensional artificial blood vessels on a matrix that includes at least laminin, entactin and collagen IV.

To test the perfusion and capacity of R-VEC vessels to sustain laminar flow, fluorescently labeled control-EC (CTRL-EC) or endothelial cells comprising an exogenous nucleic acid encoding an ETV2 (R-VEC) were seeded in parallel in a microfluidic device. As shown in FIG. 2A, after seeding endothelial cells expressing exogenous ETV2 organized and self-assembled into lumenized vessels, while control cells failed to generate blood vessels. Once a vascular network of artificial blood vessels was established, mCherry-labeled beads (4 µM) were cycled through one channel of the device to determine whether or not the stable, three-dimensional artificial blood vessels of the present disclosure can sustain laminar flow. As shown, in FIG. 2A, the stable, three-dimensional artificial blood vessels formed from endothelial cells expressing exogenous ETV2 tolerated the flow of beads across the channel. In contrast, beads did not flow across the channel including control non-ETV2 transduced endothelial cells (CTRL-EC). Further and as shown in FIG. 2B, vessel density was significantly higher in artificial blood vessels formed from endothelial cells expressing exogenous ETV2 as compared to those containing CTRL-ECs. Thus, the stable, three-dimensional lumenized blood vessel tubules formed from endothelial cells expressing exogenous ETV2 sustain perfusion without requirement for perivascular support or limiting confines of scaffolds.

Example 3. Endothelial Cells Expressing Exogenous ETV2 Form Stable, Three-Dimensional, Functional Vessels In Vivo The potential of endothelial cells expressing exogenous ETV2 to sustain functional patterned vessels was assessed using in vivo murine models. Here, SCID-beige mice were implanted subcutaneously with plugs containing mCherry or GFP labeled control human endothelial cells or reprogrammed endothelial cells expressing exogenous ETV2 mixed with laminin, entactin and collagen IV (L.E.C.). One to five months post implantation, the degree of vascularization (vessel persistence and anastomosis to the pre-existing murine vasculature) was assessed by intravital staining as shown in FIGS. 3A-M. FIG. 3A shows that mice administered plugs having reprogrammed endothelial cells expressing exogenous ETV2 (R-VEC) were visibly more vascularized than those administered control non-ETV2 transduced control endothelial cells. Both whole mount confocal pictures, as well as post sectioning of the plugs, revealed much higher vessel density, organization and patterning in mice that were administered reprogrammed endothelial cells expressing exogenous ETV2 as compared to control non-ETV2 expressing endothelial cell plugs.

Vascular function was further assessed in vivo by examining the ability of the stable 3D artificial blood vessels ability to perfuse liquid and anastomose to the mouse vasculature. See FIGS. 3B-C. Further, as shown in FIG. 3D, vessel density was significantly higher in animals injected with reprogrammed endothelial cells expressing exogenous ETV2 than control ECs at both 1-month and 2-month time-points. Similar results were obtained when analyzing the functionality of artificial blood vessels formed using Matrigel™ as a matrix instead of L.E.C at 1 week, 1-month and 2-month points. See FIGS. 3E-F. Histological analyses showed that functional perfused vessels were formed at a much higher rate with reprogrammed endothelial cells expressing exogenous ETV2 as compared to control endothelial cells. FIG. 3G. Furthermore, FIG. 3H, shows that the stable 3D blood vessels of the present disclosure contained mouse pericytes, which further stabilize the lumen geometry. Notably, myrAKT1, or ETS1 transduced endothelial cells formed non-functional artificial vessels. For example, these vessels were non-perfused and failed to vascularize in the mouse, as shown in FIGS. 3I-3K. In view of the foregoing, reprogrammed endothelial cells expressing exogenous ETV2 of the present disclosure vascularize in vivo forming a functional vascular network when injected as single cell populations in a defined matrix.

Similarly, when stable three-dimensional blood vessels formed from endothelial cells expressing exogenous ETV2 are implanted instead of administered as single cell suspensions, vascular functionality and vessel density was maintained over time. This indicates that the stable 3D blood vessels of the present disclosure could be transplanted along with organoids to regenerate organ specific tissue. Endothelial cells expressing exogenous ETV2 were cultured for 8 weeks to form stable vascular networks in vitro and then subcutaneously injected as fully formed blood vessel explants into the SCID-beige mice. Mice were then injected with VEcad antibody to identify perfused vessels. As shown in FIGS. 3L and 3M, the implanted vessels functionally anastomosed with the endogenous mouse blood vessels, as murine PFGFRβ+ pericytes were recruited around the transplanted vessels to stabilize and form vascular networks of capillary like vessels and small arterioles. Thus, the three-dimensional blood vessels of the present disclosure are stable, functional and sustain the stress of transplantation without requiring a scaffold or perivascular support. This indicates that the stable 3D blood vessels of the present disclosure are a viable vehicle for promoting vascularization in a subject.

Example 4. Transient ETV2 Expression Forms Functional Artificial Blood Vessels

Figure 4A:
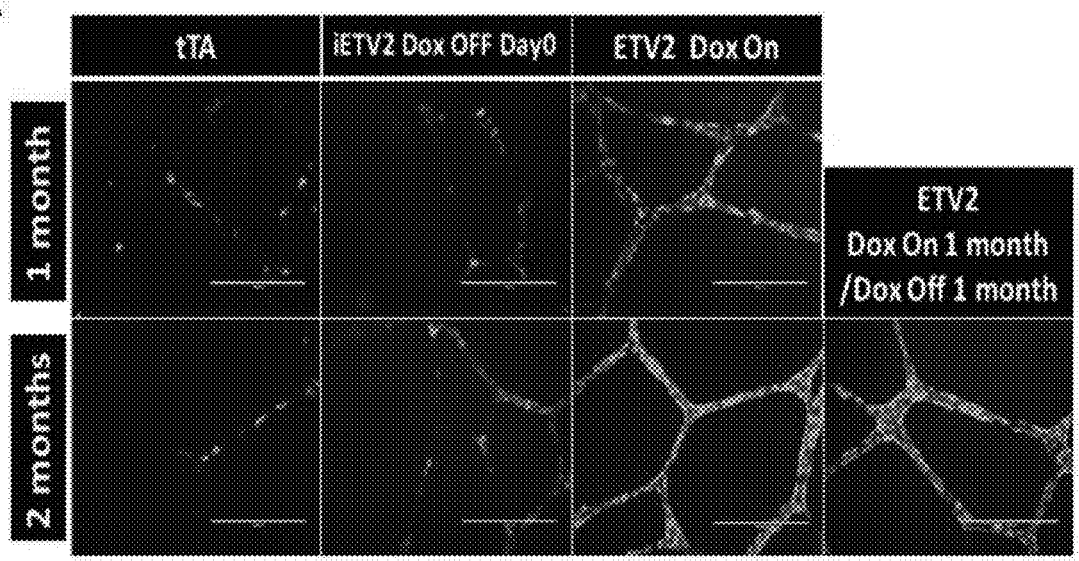
FIGS. 4A-4H. Transient ETV2 expression is sufficient for the formation and maintenance of stable and functional long-lasting human vessels. Artificial vessel formation was accomplished using an inducible ETV2 system where ETV2 expression is driven by the presence of doxycycline. Doxycycline (Dox) was either removed at day 0 of the assay, 1 month post start of the assay, or was always present. A. Fluorescence images depicting vessel formation for samples where only rtTa was present, inducible ETV2 where Dox was removed at day 0, Dox was removed after 1 month, or continuously added to the 2D or 3D cultures. B. In vivo plug assay where mice were never exposed to a Dox diet, were on a Dox diet for 1 month and then moved to regular diet for 1 month, and were continuously kept on a Dox diet. Red represents the injected human endothelial cells. White provides VECAD that was intravenously (intravitaly) injected before sacrificing the mice to identify perfused anastomosed vessels. C. Quantification of vessel density at 1 month and 2 months of development during transient ETV2 expression. D. Electron microscopy images of a lumen present in vessels where Doxycycline was continuously present and in vessels where Doxycycline was removed after 1 month. E. Venn diagram displaying number of overlapping differentially expressed genes in vessels formed by reprogrammed endothelial cells expressing ETV2 (R-VEC) after 4 weeks and a cultured control HUVECs. F. Heatmaps showing the top 20 upregulated and downregulated genes (ranked by fold change) shared between R-VEC vessels after 4 weeks in culture compared to control HUVECs. G. Heatmaps showing the top 25 upregulated and downregulated genes (ranked by fold change) in R-VEC vessels and an R-VEC monolayer after 4 weeks in culture. H. ETV2 is turned off upon Dox removal at 1 week and 4 weeks as shown by qPCR analysis relative to GAPDH expression. ns=not significant, *P<0.05, P<0.01, *P<0.001.
Figure 4B:
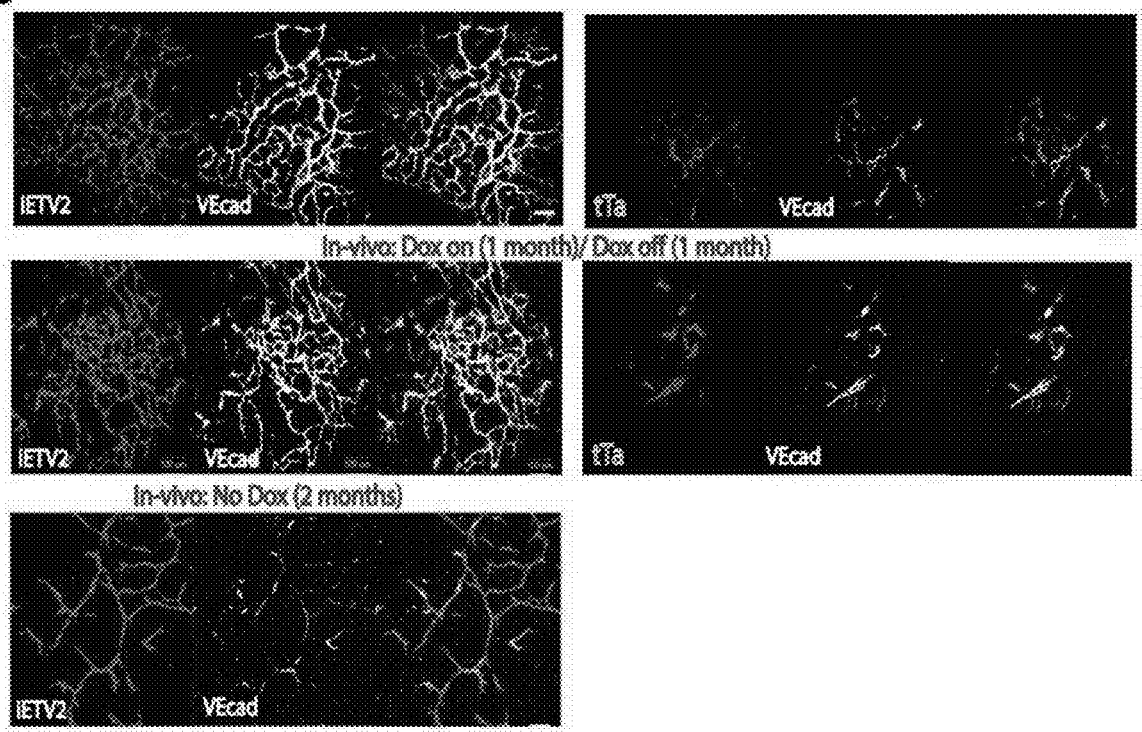
Figure 4C:
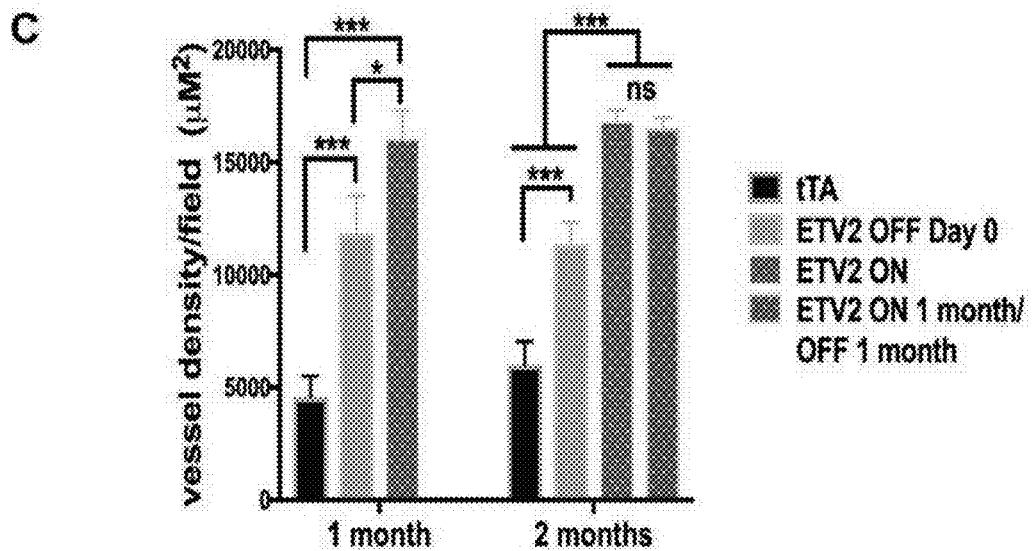
Figure 4D:
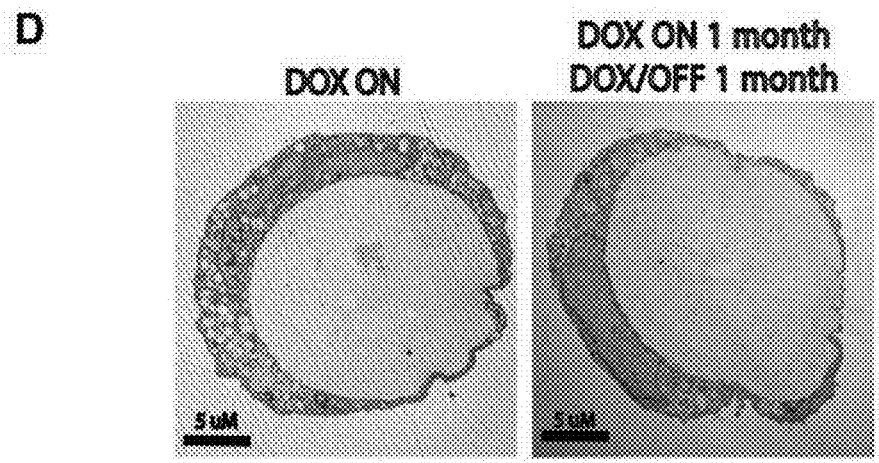

To determine whether transient expression of ETV2 is sufficient to sustain stable 3D blood vessel formation, a reverse tet-transactivator (rtTA)-doxycycline inducible expression system was used. Quantitative PCR analysis confirmed the rapid downregulation of ETV2 upon doxycycline removal. FIG. 4H. The in vitro vessel formation assay and in vivo plug assay described above show that ETV2 expression was only required until vessels could properly form at 4 weeks (i.e., 1 month), and was dispensable thereafter. FIGS. 4A-B. Indeed, artificial vessels formed by endothelial cells that expressed ETV2 during the first 4 weeks of culture sustain their ETV2-endowed vascular adaptability, as exhibited shown in FIGS. 4C-D.

Figure 4E:
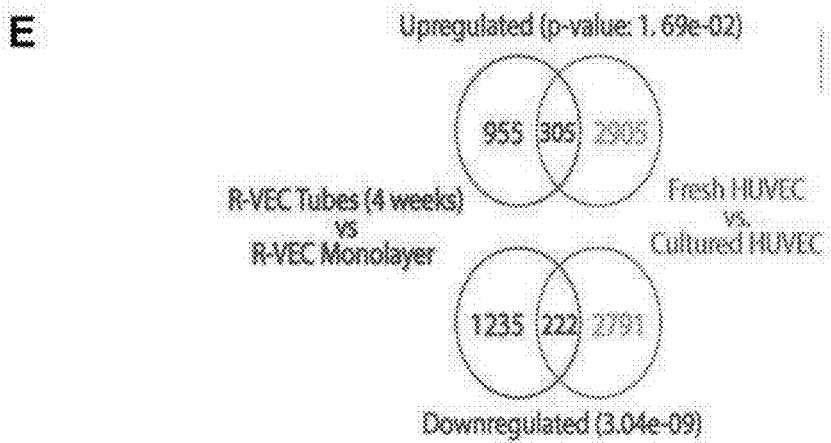
Figure 4F:
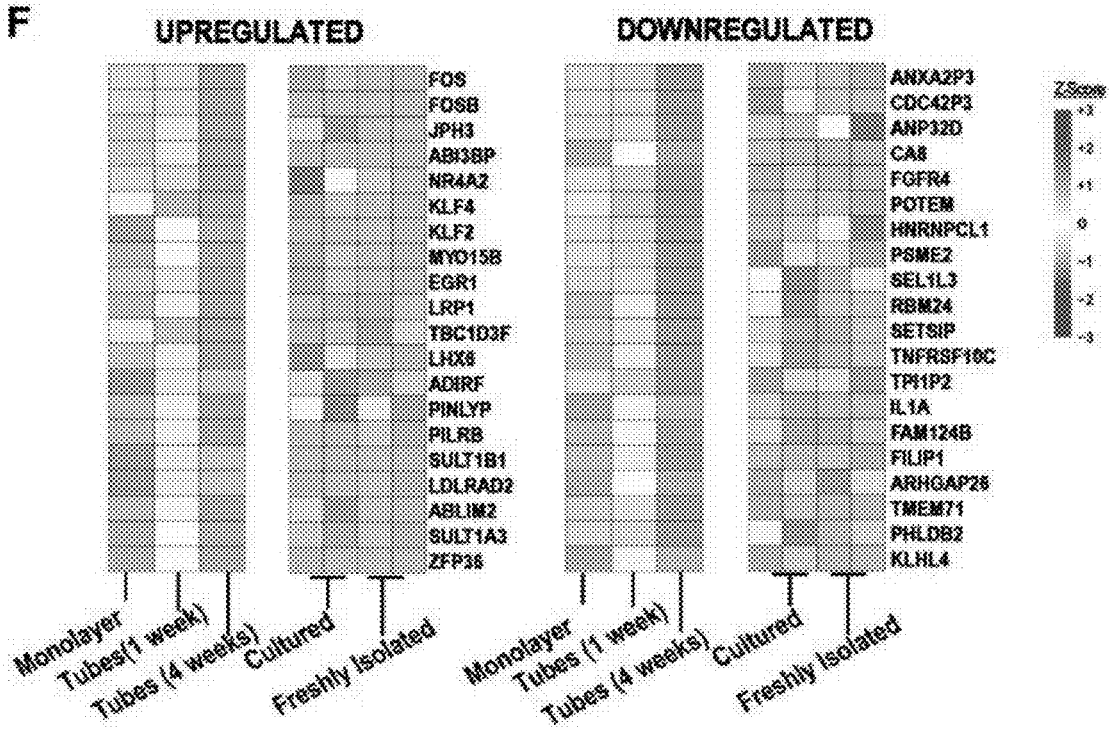
Figure 4G:
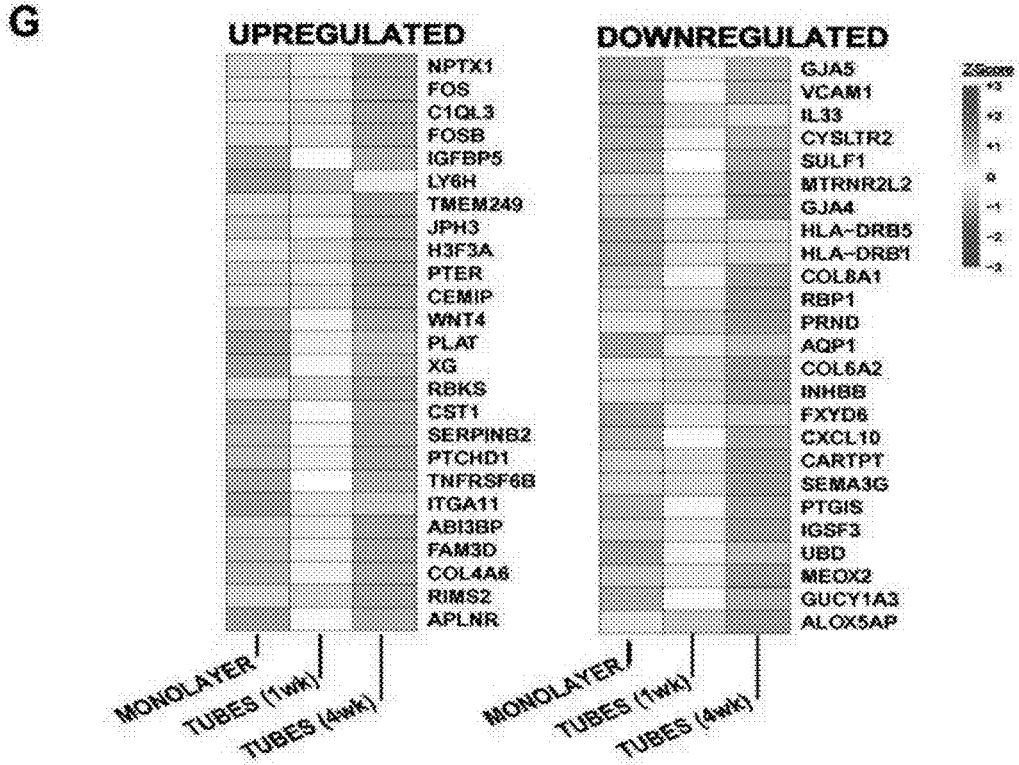
Figure 4H:
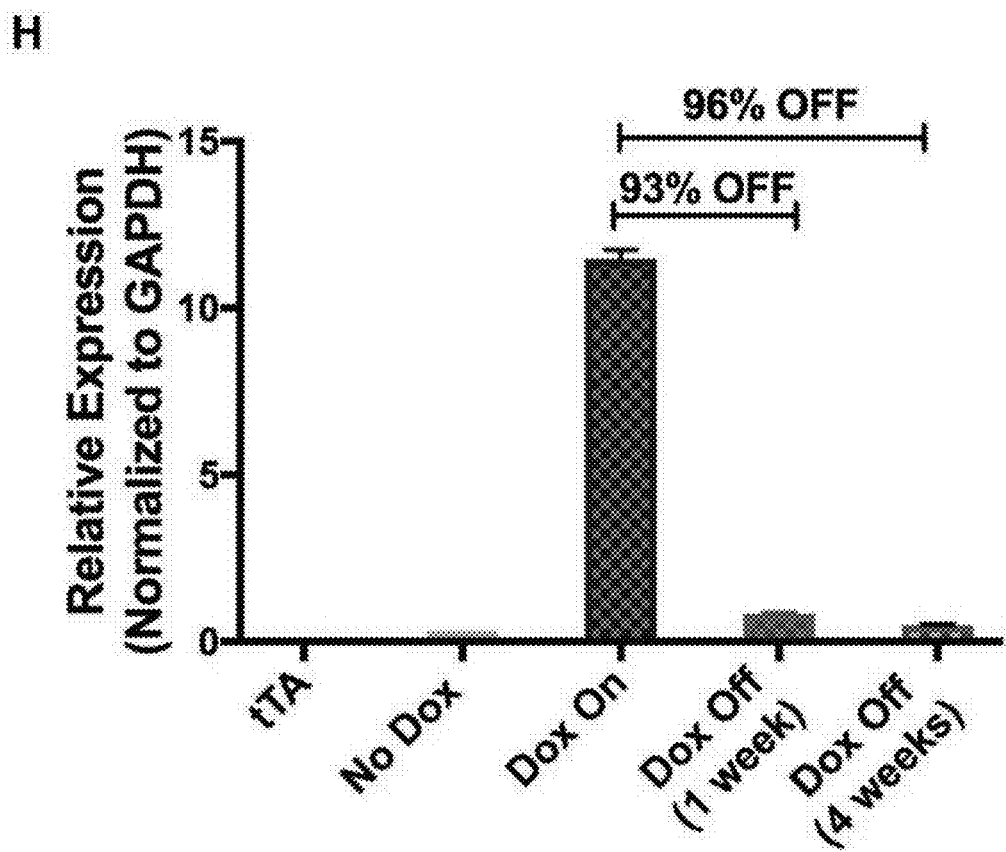

Moreover, artificial vessels formed by endothelial cells that expressed ETV2 acquire transcriptional similarities to freshly isolated endothelial cells, when compared to in vitro cultured endothelial cells as shown in FIGS. 4E and 4F. Notably, as the 3D artificial blood vessels become stable at 4 weeks, expression of upregulated genes become downregulated and the cells adapt to the overall microenvironmental milieu. See FIG. 4G.

Example 5. Reprogrammed Endothelial Cells Expressing ETV2 Vascularize Organoids

Figure 5A:
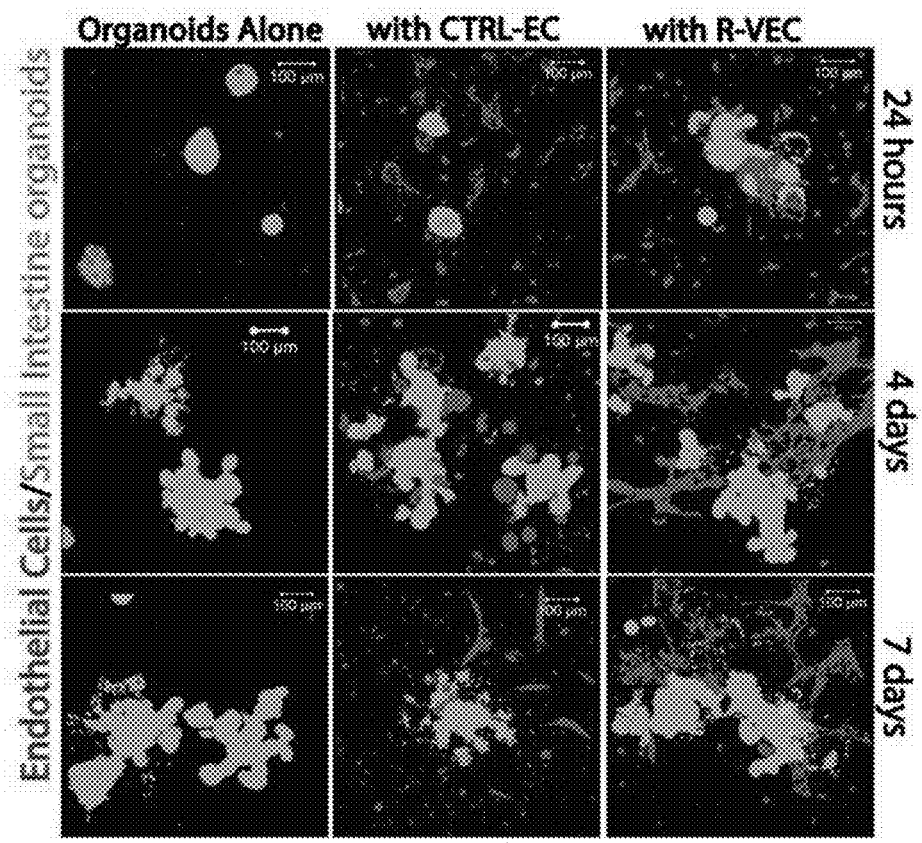
FIGS. 5A-5L. Reprogrammed endothelial cells expressing exogenous ETV2 vascularize organoids. Human or mouse derived organoids were cultured either alone, or with human CTRL-EC (control) or reprogrammed endothelial cells containing exogenous ETV2 (R-VECs). A. Representative confocal microscopy images of time course at 24 hours, 4 days and 7 days of culturing mouse small intestinal organoids (green) alone, and co-cultured with CTRL-ECs or R-VECs (red fluorescence). B. Vessel density time course in CTRL-EC versus R-VEC organoid co-cultures over a 7 day period. C. Vessel arborization (vascularization) quantified as sprouts/organoid in organoids cultured with CTRL-EC versus R-VEC. D. Confocal representation images for co-culture experiments of human normal colon organoids alone, with CTRL-EC or R-VEC. Images were taken at day 8. E. Quantification of colon organoids/field at day 8. F. Vessel density/field in CTRL-EC versus R-VEC organoid co-cultures at day 8. G. Representative confocal images of colon tumor organoids alone, or co-cultured with CTRL-EC or R-VECs. The organoids were post-stained for keratin 20 (KRT20) and EdU at day 8 of co-culturing of the R-VECs with tumor organoids. H. Quantification of vessel density in CTRL-EC or R-VEC organoid co-cultures at day 8. I. Immunofluorescence analysis of tumor colon organoids stained with EpCam, EDU and DAPI at day 8. J. Schematic representation of the R-VEC morphological education achieved post arborization of various normal and tumor organoids. Intimate cellular interaction of the intestinal organoids with R-VECs results in formation of organized geometrically patterned properly adaptable vessels. By contrast, co-mingling of the R-VECs with tumor organoids results in generation of disorganized and disrupted vessels typically seen in abnormal tumor vasculature in vivo. Thus, ETV2-transduced endothelial cells acquire unique plastic attributes to adapt to normal organoids and maladapt to tumor organoids thereby phenocopying in vivo behavior of adult vasculature. K. Representative confocal images of triple negative human breast tumor organoids alone, or co-cultured with CTRL-EC or R-VEC at 24 hours. L. Confocal images of R-VEC vascularization of breast tumor organoids at day 8. Reprogrammed endothelial cells form disorganized and poorly patterned vessels reminiscent of in vivo abnormalized tumor vessels. P<0.01, *P<0.001.

The potential for endothelial cells that express ETV2 to arborize, i.e., form a branched three-dimensional vascular network, in mouse, human or malignant epithelial organoid cultures was elucidated. GFP-labeled human or mouse small intestinal organoids were admixed with either reprogrammed endothelial cells that expressed ETV2 (R-VECs)

or naïve endothelial cells (CTRL-ECs). As shown in FIG. 5A, R-VECs were able to form highly organized 3D vessels and associate with both the stem-cell containing crypt buds and the differentiated villus-like central domain within 24 hours. The vascularization of intestinal organoids by reprogrammed endothelial cells that expressed ETV2 became more organized with formation of patterned vessels arborizing virtually every expanding organoid unit by day 4 and day 7. By contrast, naïve non-ETV2 transduced endothelial cells (CTRL-ECs) were unable to form vessels in the presence of the organoids, thereby lacking the capacity to vascularize organoids. FIG. 5A.

Figure 5B:
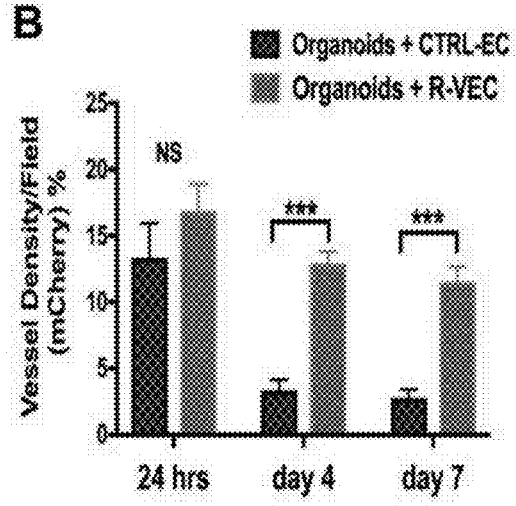
Figure 5C:
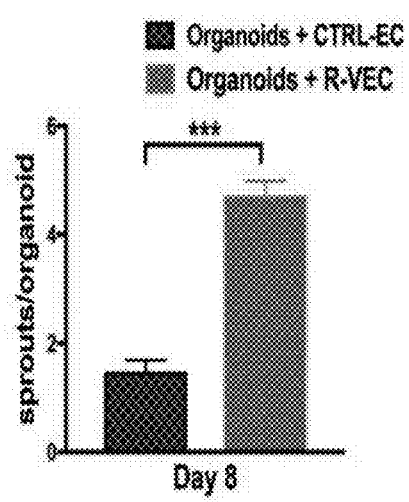

As shown in FIGS. 5B and 5C, vessel density and the number of capillaries formed per organoid were found to be significantly higher in the organoids cultured with reprogrammed endothelial cells.

Figure 5D:
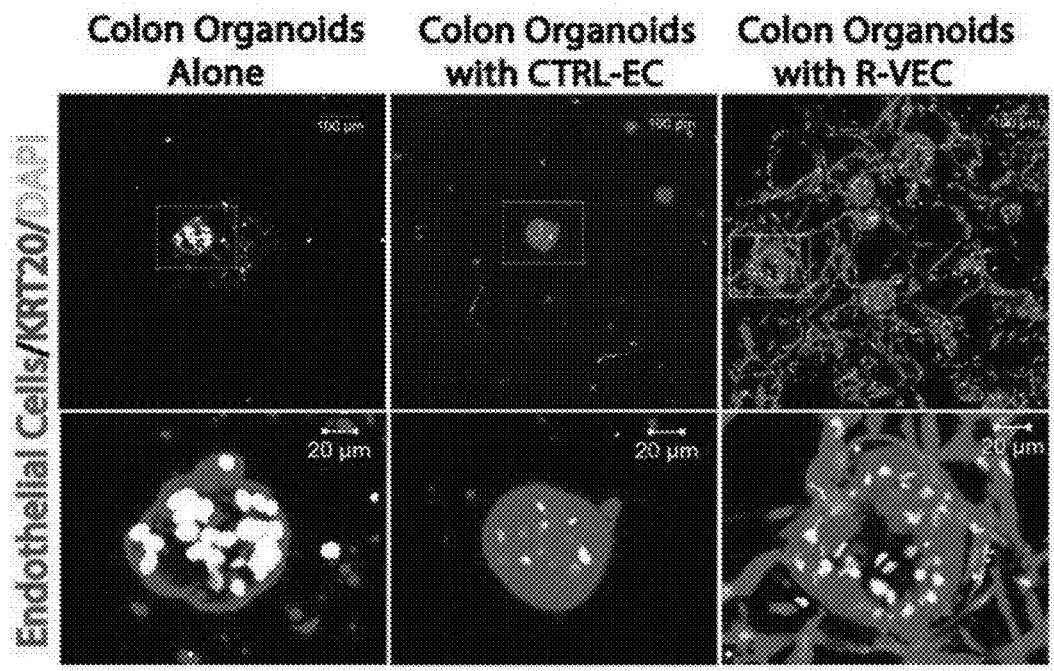
Figure 5E:
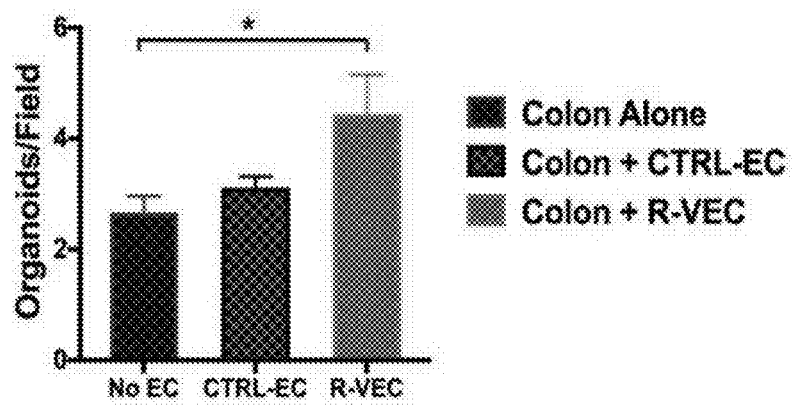
Figure 5F:
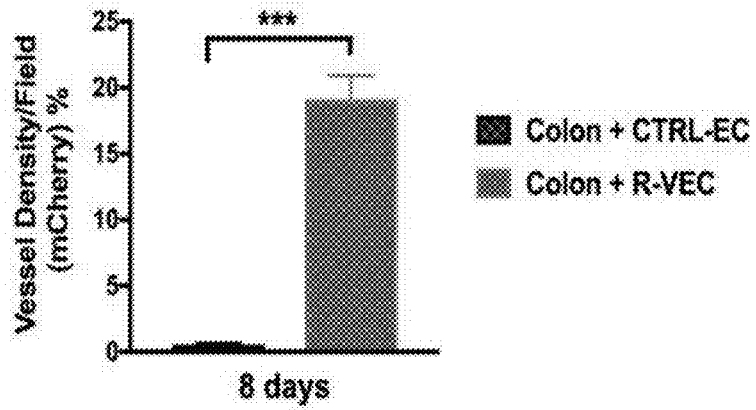

As shown in FIGS. 5D-5F, reprogrammed endothelial cells that expressed ETV2 arborized and formed a vascular network with human-derived normal colon organoids. Furthermore, vessel density, numbers of colon organoids, as well as organoid size was found to be higher when co-cultured with reprogrammed endothelial cells that expressed ETV2. Thus, reprogrammed endothelial cells enable differentiated endothelial cells to engage endogenous epithelial cells and form a functional vascular network.

Figure 5G:
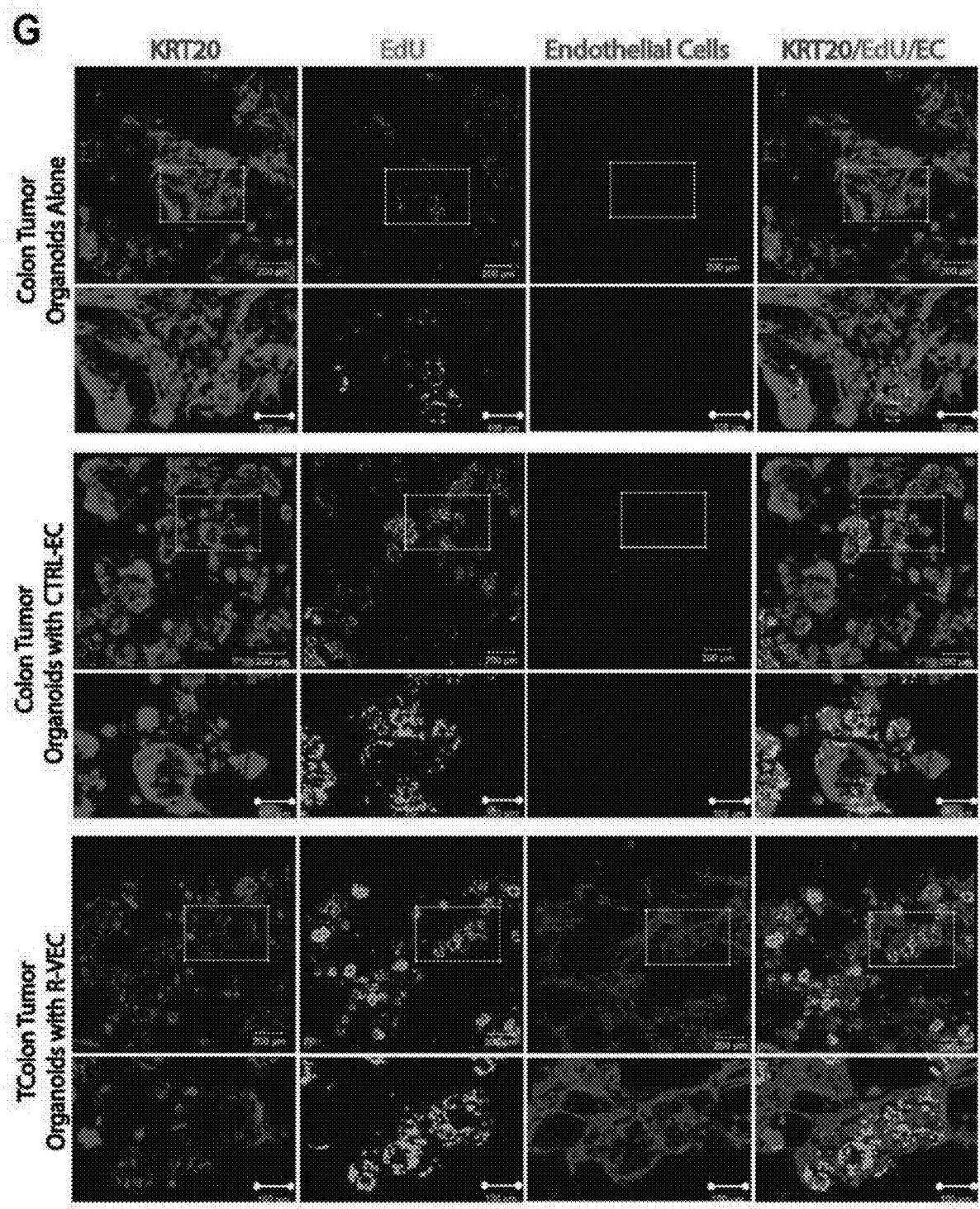
Figures 5H, 5I, 5J:
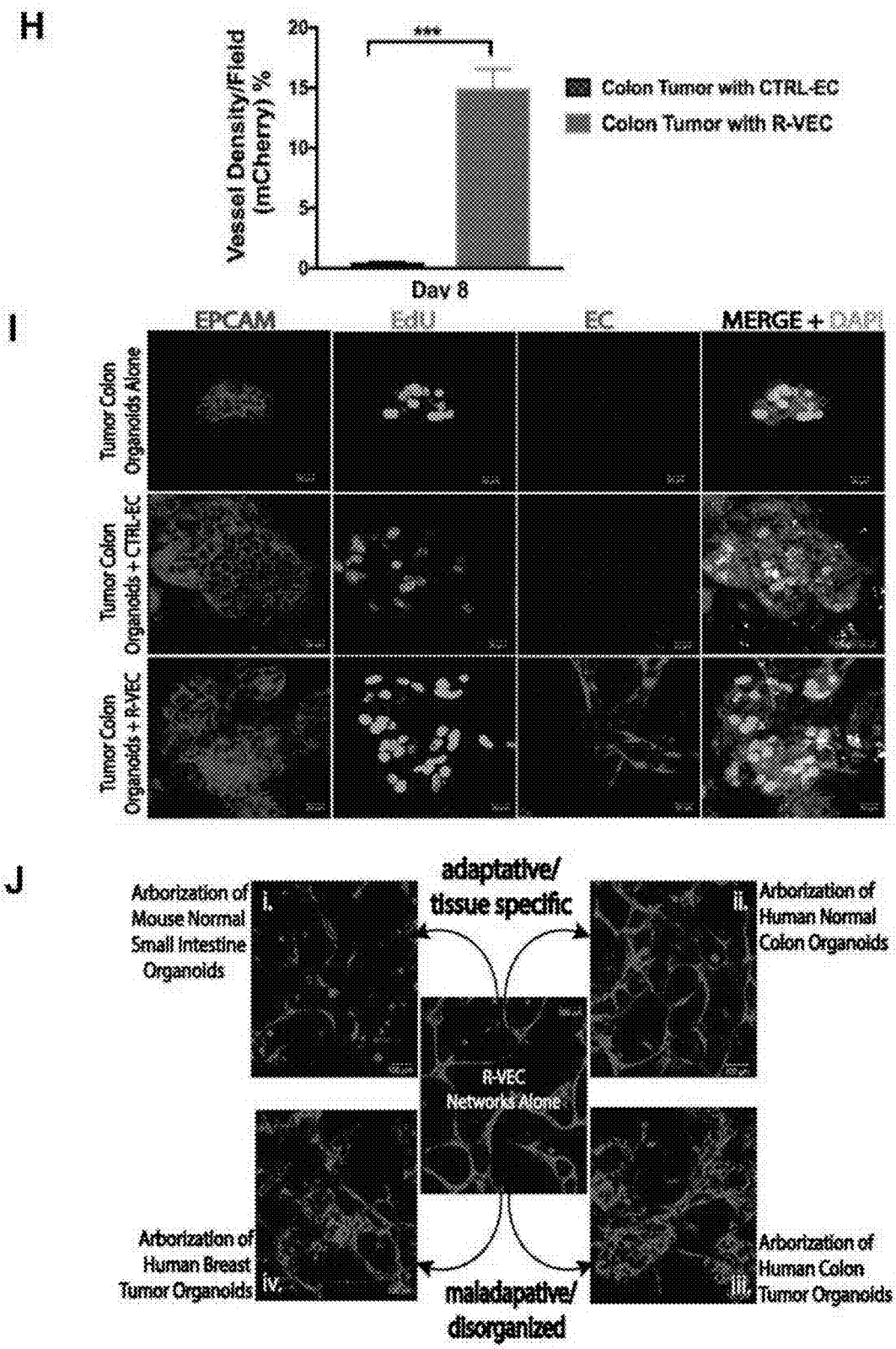

As shown in FIGS. 5G-5J, within 24 hours reprogrammed endothelial cells that express ETV2 (R-VEC) migrated toward tumor organoids and aggressively and profusely vascularize tumor organoids, while naïve endothelial cells (CTRL-EC) were unable to do so. For example, FIG. 5G shows that in seven days, all the tumor organoids were arborized with disorganized highly dense populations of vessels. Vessel density was also found to be much higher in the R-VEC co-cultures as compared to control non-ETV2 transduced endothelial cells, as shown in FIG. 5H. Staining for epithelial marker EpCam, revealed the intimate cell-cell interaction between the tumor colon organoid cells and the reprogrammed endothelial cells. See FIG. 5I. Notably, unlike the normal intestinal and colon organoid co-cultures in which reprogrammed endothelial cells formed organized vascular plexus, the vessels within the tumor organoids were disorganized and abnormal in shape and size mimicking tumor vasculature. See FIGS. 5G and 5J.

Figure 5K:
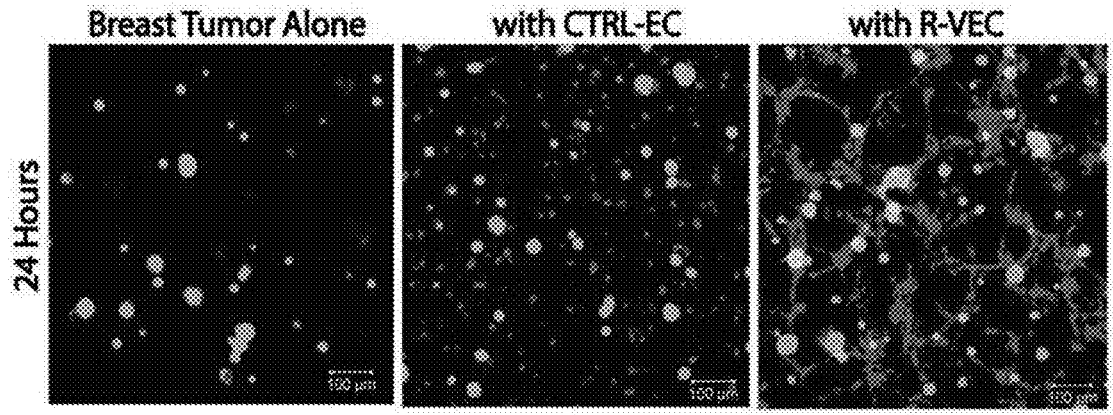
Figure 5L:
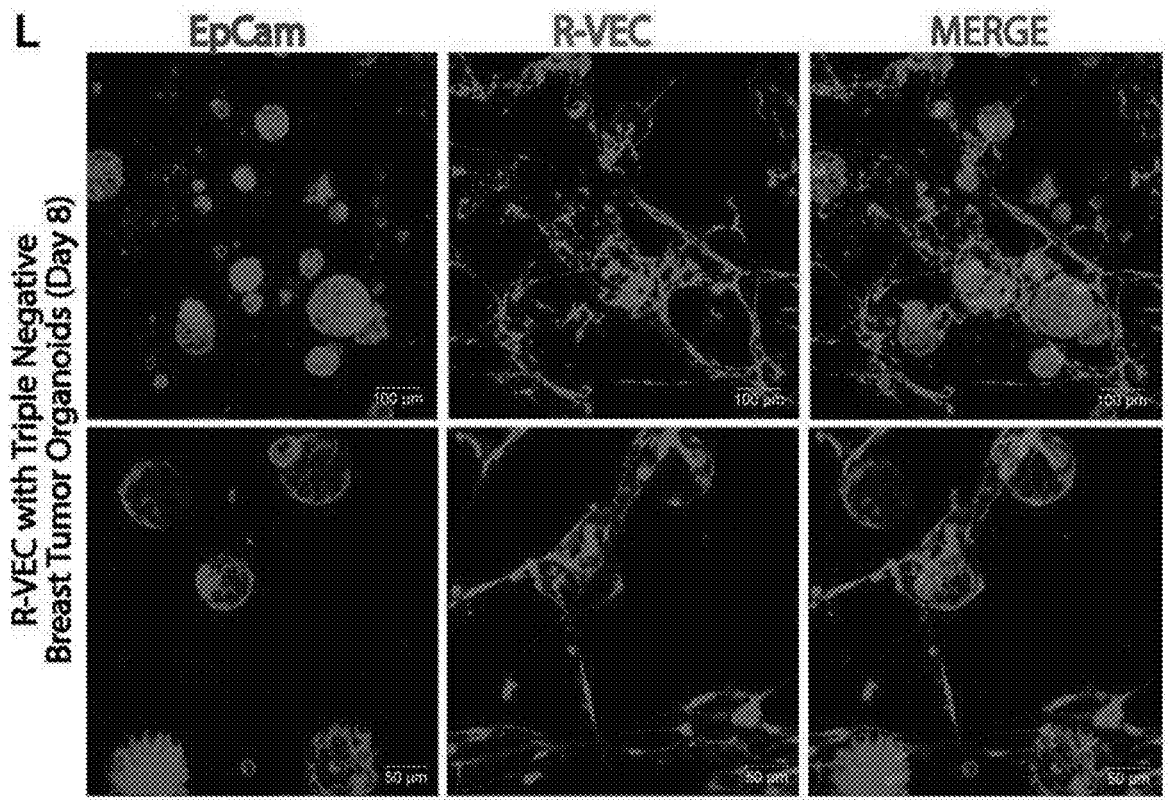

Other patient derived tumor organoids, including triple negative breast cancer organoids also yielded similar results, as exemplified in FIGS. 5K-5L.

In view of the foregoing, the reprogrammed endothelial cells and stable 3D artificial blood vessels of the present disclosure are capable of vascularizing organoids of many different tissue types, and adapt to the environment they are introduced into, behaving with altered remodeling and morphology in settings of normal and tumorigenic organoids. See, for example, FIG. 5J.

Example 6. Reprogrammed Endothelial Cells Vascularize Decellularized Organs

Figures 6A, 6B, 6C, 6D, 6E:
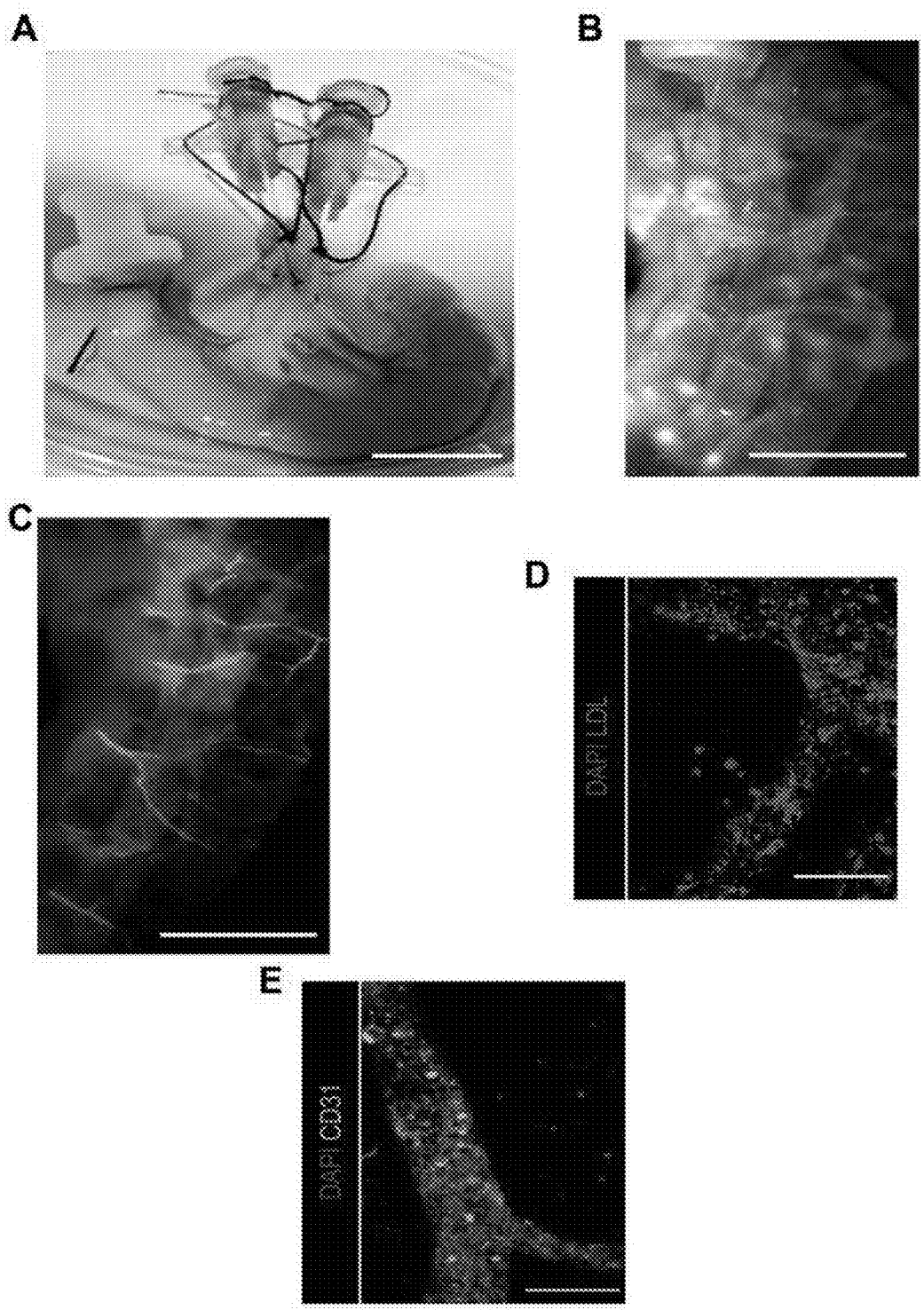
FIGS. 6A-6J. Endothelial cells that include exogenous ETV2 engraft and proliferate in a decellularized rat intestine and engraft within host vasculature upon heterotopical implantation of the re-endothelialized intestine. A. Harvested rat intestines were cannulated through lumen, mesenteric artery and mesenteric vein. Scale bar 1 cm. B. Decellularized intestine macroscopically preserves the native vasculature scaffold structures, scale bar 5 mm. C. Seeded R-VECs migrate to and cover distal capillaries. Scale bar 5 mm. D. After 7 days of culture in a bioreactor, perfusion with fluorescent low density lipoprotein (LDL) reveals patent endothelialized vessels. Scale bar 50 µm. E. R-VECs repopulate the vasculature. Scale bar 100 µm. F. R-VECs spread evenly in the whole vasculature forming distal capillaries and blood vessels, while CTRL-ECs are unable to vascularize the organ. Scale bar 500 µm. G. Quantification of the area vascularized by R-VECs compared to control ECs shows an increased re-endothelialization by R-VECs. H.-K. Heterotopic implantation of re-endothelialized intestines shows engraftment after 1 and 4 weeks of the cells and anastomosis to the host vasculature by intravital intravenous injection of fluorescent isolectin and anti-human VE-Cadherin antibody (scale bars 50 µm and 20 µm). *P<0.05, **P<0.01.
Figure 6F:
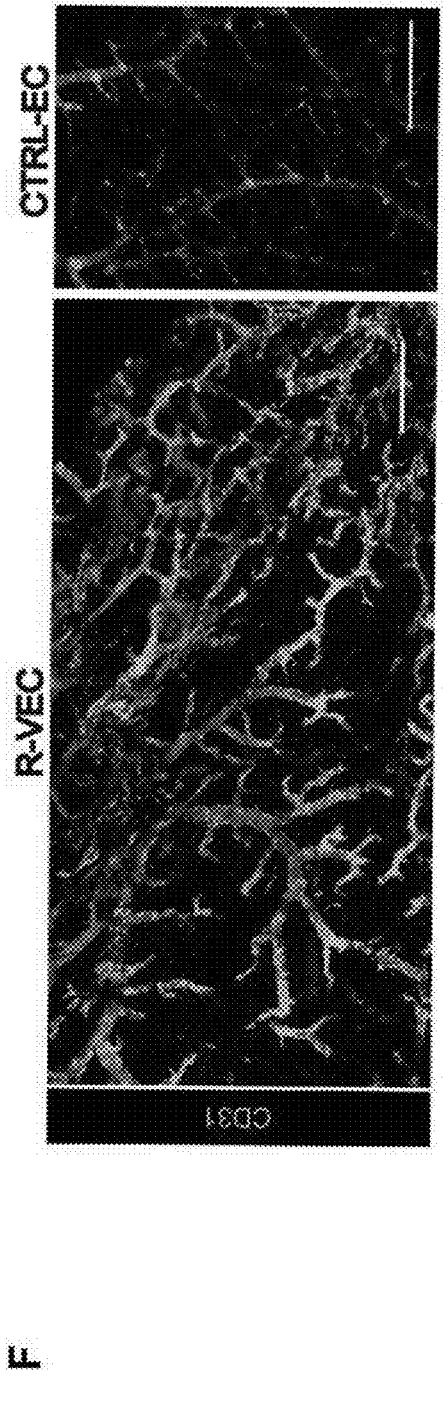
Figure 6G:
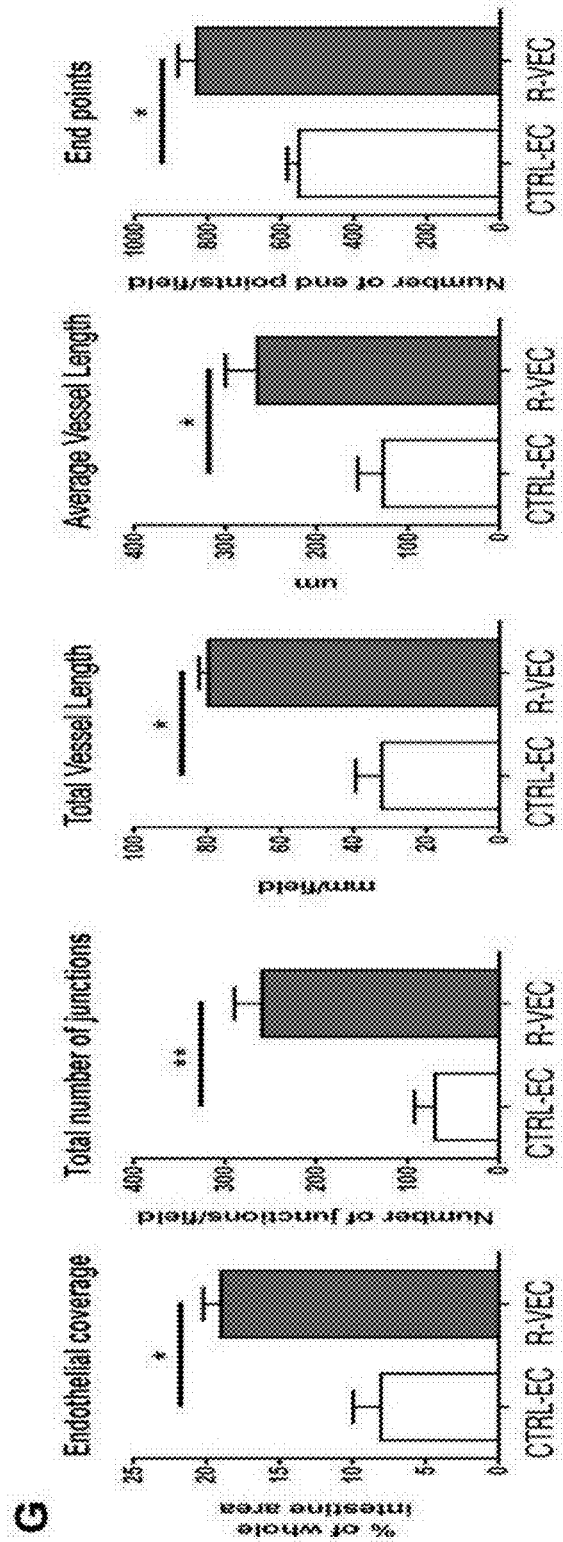
Figure 6H:
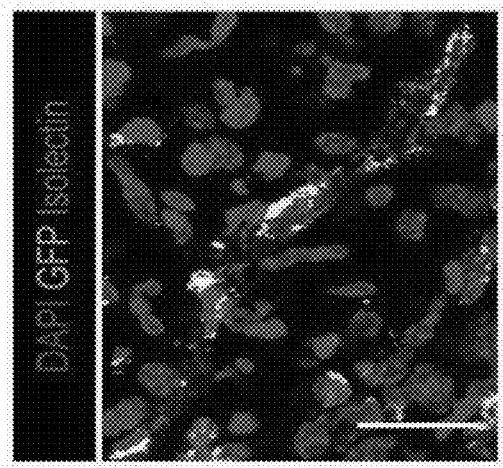
Figure 6I:
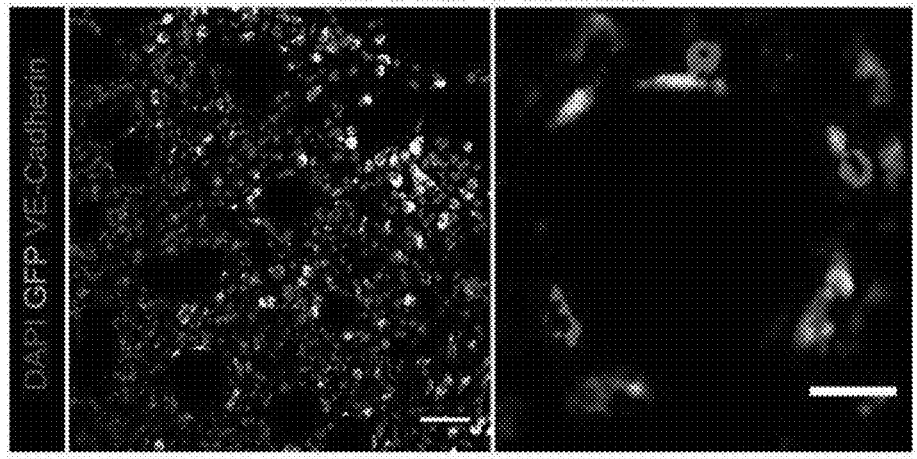
Figure 6J:
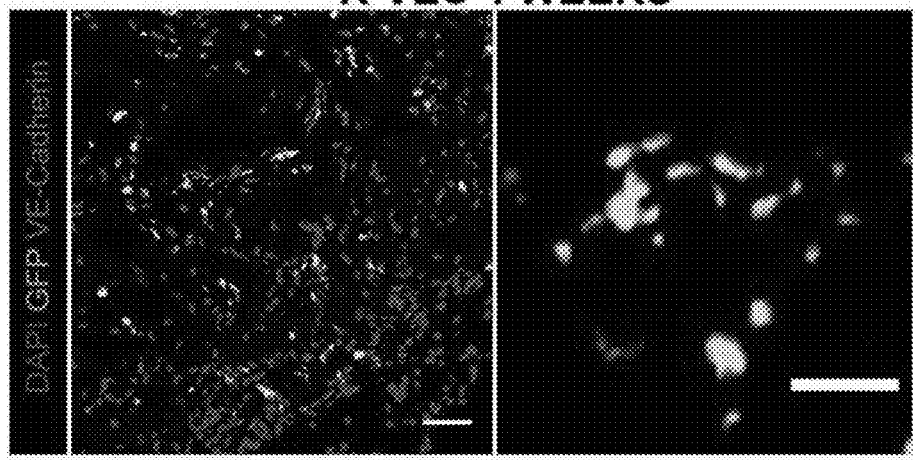

In regenerative medicine, the generation of long-lasting functional vascular structures that include capillaries and arterioles has not yet been accomplished. Specifically, while large caliber vessels could be colonized with endothelial cells it is difficult to form smaller capillary size vessels that could provide a long-lasting and distributed blood supply to an organ or model organ. Here, reprogrammed endothelial cells expressing exogenous ETV2 were introduced to a decellularized intestinal organ model, where they were able to establish vascularized structures in vitro inside a bioreactor. See FIGS. 6A-B. Results show that reprogrammed endothelial cells expressing exogenous ETV2 (R-VECs) profusely populated the capillaries of a decellularized intestine achieving an even distribution throughout the whole area of the intestine wall. See FIG. 6C. As shown in FIGS. 6D-6E, intravital staining with a CD31 antibody and acetylated-LDL uptake revealed a much higher vascular coating when using R-VECs compared to using control non-ETV2 transduced endothelial cells (CTRL-ECs). Quantification of re-endothelialized area and vascular network parameters corroborated the higher vascularization potential of reprogrammed endothelial cells expressing exogenous ETV2, as shown in FIGS. 6F and 6G. After 1 week of culturing in vitro, the revascularized intestines were implanted in the omentum of the immunocompromised NOD-SCID-γ mice. Reprogrammed endothelial cells expressing exogenous ETV2 vascularized decellularized intestines retained the continuity of the large (arteries and veins) and small caliber vessels (capillaries) and anastomosed to the mouse vasculature as shown by intravital isolectin and human VEcad injection at both 1 and 4 weeks. See FIGS. 6H-6J.

What is claimed is:

1. A method for producing a three-dimensional blood vessel comprising:
   a) culturing an endothelial cell comprising an exogenous nucleic acid encoding an ETV2 transcription factor on a matrix under conditions wherein the endothelial cell expresses the ETV2 transcription factor for at least 3-4 weeks to induce formation of a three-dimensional blood vessel; and
   b) isolating said three-dimensional blood vessel.

2. The method of claim 1, further comprising culturing the cells of step a) for an additional period of time, wherein said further culturing occurs under conditions wherein the cells do not express the ETV2 transcription factor.

3. The method of claim 2, wherein said further culturing occurs for at least one week.

4. The method of claim 1, wherein said matrix comprises laminin, entactin, collagen, or a combination thereof.

5. The method of claim 4, wherein said matrix comprises:
   laminin and entactin at a combined concentration of 5.25 mg/mL; and
   0.2 mg/mL collagen IV.

6. The method of claim 1, wherein said endothelial cell comprises a human umbilical vein endothelial cell (HUVEC), an adipose derived endothelial cell or an organ-specific endothelial cell.

7. The method of claim 6, wherein said organ-specific endothelial cell is selected from the group consisting of heart, muscle, kidney, testis, ovary, lymphoid, liver, pancreas, brain, lungs, bone marrow, spleen, large intestine, and small intestine.

8. The method of claim 1, wherein said 3-4 week culturing step comprises culturing said endothelial cells in serum free media for at least 7 days.

9. The method of claim 8, wherein said culturing in serum free media is carried out at less than atmospheric (20%) oxygen tension.

10. The method of claim 9, wherein said oxygen tension is 5%.

11. The method of claim 1, wherein said culturing step a) occurs in the absence of a perivascular support scaffold.

12. A three-dimensional blood vessel produced by the method of claim 1.

13. A method for promoting vascularization in a subject comprising administering to the subject the three-dimensional blood vessel of claim 12.

14. The method of claim 13, wherein said administration comprises implanting said three-dimensional blood vessel in said subject to form a functional three-dimensional vascular network in said subject.

15. The method of claim 14, wherein said functional three-dimensional vascular network comprises a capillary, an arteriole, a venule or a lymphatic vessel.

16. A method for vascularizing an organoid comprising culturing said organoid with an endothelial cell comprising an exogenous nucleic acid encoding an ETV2 transcription factor on a matrix under conditions wherein the endothelial cell expresses the ETV2 transcription factor.

17. The method of claim 16, wherein the matrix comprises laminin, entactin, collagen, or a combination thereof.

18. The method of claim 16, wherein the organoid is selected from the group consisting of a small intestine organoid, colon organoid, kidney organoid, heart organoid and a tumor organoid.

19. The method of claim 16, wherein said culturing comprises culturing in media comprising basic FGF (FGF-2) and heparin for at least 7 days.

20. The method of claim 16, further comprising isolating said vascularized organoid.

21. The method of claim 20, wherein said isolated vascularized organoid is administered to a subject.

22. The method of claim 20, wherein said isolated vascularized organoid is administered to the subject by surgical implantation.

* * * * *